US012766034B2

(12) United States Patent
Roeber et al.

(10) Patent No.: US 12,766,034 B2
(45) Date of Patent: Oct. 20, 2026

(54) GLAUCOMA TREATMENT SYSTEMS AND METHODS

(71) Applicant: W. L. Gore & Associates, Inc., Newark, DE (US)

(72) Inventors: Peter J. Roeber, Oxford, PA (US); Jeffrey C. Towler, Wilmington, DE (US)

(73) Assignee: W.L. Gore & Associates, Inc., Newark, DE (US)

( * ) Notice: Subject to any disclaimer, the term of this patent is extended or adjusted under 35 U.S.C. 154(b) by 348 days.

(21) Appl. No.: 17/740,010

(22) Filed: May 9, 2022

(65) Prior Publication Data

US 2022/0331162 A1 Oct. 20, 2022

Related U.S. Application Data

(63) Continuation of application No. 15/922,701, filed on Mar. 15, 2018, now Pat. No. 11,351,058.
(Continued)

(51) Int. Cl.
*A61F 9/007* (2006.01)
*A61F 9/00* (2006.01)
(Continued)

(52) U.S. Cl.
CPC ........ *A61F 9/00781* (2013.01); *A61L 31/048* (2013.01); *A61L 31/146* (2013.01);
(Continued)

(58) Field of Classification Search
CPC ... A61F 9/00781; A61F 9/0017; A61M 27/00; A61M 27/002; A61M 2205/3334; A61L 2430/16
See application file for complete search history.

(56) References Cited

U.S. PATENT DOCUMENTS 3,618,604 A 11/1971 Ness
3,683,928 A 8/1972 Kuntz
(Continued)

FOREIGN PATENT DOCUMENTS

AU 06600/12 B2 6/1995
AU 2014280907 A1 1/2015
(Continued)

OTHER PUBLICATIONS

Ando et al., Ten-year experience with handmade trileaflet polytetrafluoroethylene valved conduit used for pulmonary reconstruction. The Journal of Thoracic and Cardiovascular Surgery, Jan. 2009, vol. 137, No. 1, pp. 124-131.
(Continued)

*Primary Examiner* — Philip R Wiest
*Assistant Examiner* — Meagan Ngo
(74) *Attorney, Agent, or Firm* — Nelson Mullins Riley & Scarborough LLP

(57) ABSTRACT

Glaucoma treatment devices are disclosed. In various example, the glaucoma treatment devices include a body and a fluid conduit that are configured to help facilitate evacuation of fluid from a fluid-filled body cavity, and reabsorption of the evacuated aqueous humor by the body through tissue surrounding the glaucoma treatment device. In some examples, the glaucoma treatment device is configured such that a flow resistance through the fluid conduit can be modified post-operatively one or more times.

24 Claims, 14 Drawing Sheets

Related U.S. Application Data

(60) Provisional application No. 62/473,090, filed on Mar. 17, 2017.

(51) Int. Cl.
*A61L 31/04* (2006.01)
*A61L 31/14* (2006.01)
*A61M 27/00* (2006.01)

(52) U.S. Cl.
CPC ........... *A61M 27/00* (2013.01); *A61F 9/0017* (2013.01); *A61F 2210/0076* (2013.01); *A61F 2230/0091* (2013.01); *A61F 2240/001* (2013.01); *A61F 2250/0003* (2013.01); *A61F 2250/0023* (2013.01); *A61F 2250/0051* (2013.01); *A61F 2250/0059* (2013.01); *A61L 2430/16* (2013.01); *A61M 27/002* (2013.01); *A61M 2205/04* (2013.01); *A61M 2205/3334* (2013.01); *A61M 2205/3341* (2013.01); *A61M 2210/0612* (2013.01)

(56) References Cited

U.S. PATENT DOCUMENTS 3,828,777 A 8/1974 Ness
3,960,150 A 6/1976 Hussain et al.
3,962,414 A 6/1976 Michaels
4,014,335 A 3/1977 Arnold
4,182,342 A 1/1980 Smith
4,186,184 A 1/1980 Zaffaroni
4,554,918 A 11/1985 White
4,579,221 A 4/1986 Corella
4,729,761 A 3/1988 White
4,759,759 A 7/1988 Walker et al.
5,026,395 A 6/1991 Nakajima et al.
5,037,434 A 8/1991 Lane
5,147,647 A 9/1992 Darougar
5,163,955 A 11/1992 Love et al.
5,282,851 A 2/1994 Jacob-LaBarre
5,378,475 A 1/1995 Smith et al.
5,423,777 A 6/1995 Tajiri et al.
5,476,445 A 12/1995 Baerveldt et al.
5,676,679 A 10/1997 Simon et al.
5,681,275 A 10/1997 Ahmed
5,702,414 A 12/1997 Richter et al.
5,708,044 A 1/1998 Branca
5,713,953 A 2/1998 Vallana et al.
5,752,928 A 5/1998 De et al.
5,773,019 A 6/1998 Ashton et al.
5,861,028 A 1/1999 Angell
5,882,327 A 3/1999 Jacob
5,928,281 A 7/1999 Huynh et al.
5,935,163 A 8/1999 Gabbay
6,050,970 A 4/2000 Baerveldt
6,074,419 A 6/2000 Healy et al.
6,086,612 A 7/2000 Jansen
6,142,969 A 11/2000 Nigam
6,171,335 B1 1/2001 Wheatley et al.
6,174,331 B1 1/2001 Moe et al.
6,186,974 B1 2/2001 Allan et al.
6,197,143 B1 3/2001 Bodnar
6,254,636 B1 7/2001 Peredo
6,261,256 B1 7/2001 Ahmed
6,283,995 B1 9/2001 Moe et al.
6,287,338 B1 9/2001 Sarnowski et al.
6,364,905 B1 4/2002 Simpson et al.
6,432,542 B1 8/2002 Tsai
6,450,984 B1 9/2002 Lynch et al.
6,471,689 B1 10/2002 Joseph et al.
6,541,589 B1 4/2003 Baillie
6,562,069 B2 5/2003 Cai et al.
6,562,446 B1 5/2003 Totsuka
6,613,086 B1 9/2003 Moe et al.
6,613,087 B1 9/2003 Healy et al.
6,696,526 B1 2/2004 Kaulbach et al.
6,699,210 B2 * 3/2004 Williams .............. A61L 31/044 623/905
6,699,211 B2 3/2004 Savage
6,713,081 B2 3/2004 Robinson et al.
6,881,197 B1 4/2005 Nigam
6,994,666 B2 2/2006 Shannon et al.
7,018,404 B2 3/2006 Holmberg et al.
7,261,732 B2 8/2007 Justino
7,306,729 B2 12/2007 Bacino et al.
7,320,705 B2 1/2008 Quintessenza
7,331,993 B2 2/2008 White
7,361,189 B2 4/2008 Case et al.
7,462,675 B2 12/2008 Chang et al.
7,531,611 B2 5/2009 Sabol et al.
7,604,663 B1 10/2009 Reimink et al.
7,833,565 B2 11/2010 O'Connor et al.
7,862,610 B2 1/2011 Quintessenza
7,883,717 B2 2/2011 Varner et al.
8,216,631 B2 7/2012 O'Connor et al.
8,219,229 B2 7/2012 Cao et al.
8,246,676 B2 8/2012 Acosta et al.
8,267,994 B2 9/2012 Lei
8,273,101 B2 9/2012 Garcia et al.
8,303,647 B2 11/2012 Case
8,399,006 B2 3/2013 De Juan, Jr. et al.
8,545,430 B2 10/2013 Silvestrini
8,556,960 B2 10/2013 Agnew et al.
8,623,395 B2 1/2014 De et al.
8,632,489 B1 1/2014 Ahmed
8,637,144 B2 1/2014 Ford
8,690,939 B2 4/2014 Miller
8,834,406 B2 9/2014 Snyder et al.
8,834,911 B2 9/2014 Glezer et al.
8,888,734 B2 11/2014 Nissan et al.
8,961,593 B2 2/2015 Bonhoeffer et al.
8,961,599 B2 2/2015 Bruchman et al.
8,961,600 B2 2/2015 Nissan et al.
9,139,669 B2 9/2015 Xu et al.
9,155,610 B2 10/2015 Soletti et al.
9,155,618 B2 10/2015 Kalmann et al.
9,216,108 B2 12/2015 Jain et al.
9,259,313 B2 2/2016 Wheatley
9,301,835 B2 4/2016 Campbell et al.
9,301,837 B2 4/2016 Beith
9,326,891 B2 5/2016 Horvath et al.
9,364,322 B2 6/2016 Conklin et al.
9,370,444 B2 6/2016 Cunningham, Jr.
9,375,347 B2 6/2016 Stergiopulos
9,539,089 B2 1/2017 Beith
9,572,713 B2 2/2017 Lind et al.
9,636,219 B2 5/2017 Keidar et al.
9,636,254 B2 5/2017 Yu et al.
9,655,720 B2 5/2017 Bluestein et al.
9,675,453 B2 6/2017 Guttenberg et al.
9,833,314 B2 12/2017 Corbett
9,849,629 B2 12/2017 Zagl et al.
9,987,120 B2 6/2018 Soletti et al.
9,999,500 B2 6/2018 Greenslet et al.
10,052,200 B2 8/2018 Chung et al.
10,195,023 B2 2/2019 Wrobel
10,299,915 B2 5/2019 Edelman et al.
10,307,292 B2 6/2019 Litvin
10,398,593 B2 9/2019 Erickson et al.
10,398,707 B2 9/2019 Hughes
10,413,402 B2 9/2019 Squara
10,413,403 B2 9/2019 Boden et al.
10,426,609 B2 10/2019 Edelman et al.
10,433,955 B2 10/2019 Edelman et al.
10,512,537 B2 12/2019 Corbett et al.
10,588,746 B2 3/2020 Bernstein et al.
10,603,164 B2 3/2020 Girard et al.
10,849,731 B2 12/2020 Cully et al.
10,959,941 B2 3/2021 Haffner
11,351,058 B2 6/2022 Roeber et al.
11,406,533 B2 8/2022 Roeber et al.
11,523,940 B2 12/2022 Roeber et al.
2002/0106395 A1 8/2002 Brubaker
2002/0110635 A1 8/2002 Brubaker et al.

(56) References Cited

U.S. PATENT DOCUMENTS

2002/0156413 A1 10/2002 Williams et al.
2002/0165478 A1 11/2002 Gharib et al.
2002/0198594 A1 12/2002 Schreck
2003/0014036 A1 1/2003 Varner et al.
2003/0027332 A1 2/2003 Afrance et al.
2003/0088260 A1 5/2003 Smedley et al.
2003/0094731 A1 5/2003 Simpson
2003/0109923 A1 6/2003 Chinn et al.
2003/0229303 A1 12/2003 Haffner et al.
2004/0024345 A1 2/2004 Gharib et al.
2004/0215333 A1 10/2004 Duran et al.
2005/0085892 A1 4/2005 Goto et al.
2005/0106211 A1 5/2005 Nelson et al.
2005/0137538 A1 6/2005 Kunzler et al.
2005/0171507 A1 8/2005 Christian et al.
2005/0182350 A1 8/2005 Nigam
2005/0228487 A1 10/2005 Kujawski
2005/0234546 A1 10/2005 Nugent et al.
2005/0244465 A1 11/2005 Nivaggioli et al.
2005/0250788 A1 11/2005 Tu et al.
2005/0261759 A1 11/2005 Lambrecht et al.
2005/0266047 A1 12/2005 Tu et al.
2005/0267398 A1 12/2005 Protopsaltis et al.
2005/0273033 A1 12/2005 Grahn et al.
2006/0036207 A1* 2/2006 Koonmen .............. B82Y 30/00 604/8
2006/0109923 A1 5/2006 Cai et al.
2006/0110429 A1 5/2006 Reiff et al.
2006/0189917 A1 8/2006 Mayr et al.
2006/0195187 A1 8/2006 Stegmann et al.
2006/0258994 A1 11/2006 Avery
2007/0077270 A1 4/2007 Wen
2007/0078371 A1 4/2007 Brown et al.
2007/0083184 A1 4/2007 Simpson
2007/0088432 A1 4/2007 Solovay et al.
2007/0118147 A1 5/2007 Smedley et al.
2007/0207186 A1 9/2007 Scanlon et al.
2007/0293872 A1 12/2007 Peyman
2008/0071361 A1 3/2008 Tuval et al.
2008/0082161 A1 4/2008 Woo
2008/0091261 A1 4/2008 Long et al.
2008/0133005 A1 6/2008 Andrieu et al.
2008/0147021 A1 6/2008 Jani
2008/0200977 A1 8/2008 Paul et al.
2008/0264993 A1 10/2008 Schulte et al.
2008/0268314 A1 10/2008 Han et al.
2008/0277332 A1 11/2008 Liu
2008/0312737 A1 12/2008 Jin
2009/0043321 A1 2/2009 Conston et al.
2009/0155326 A1 6/2009 Mack et al.
2009/0157175 A1 6/2009 Benichou
2009/0226731 A1 9/2009 Wittmann et al.
2009/0227933 A1 9/2009 Karageozian
2009/0240215 A1 9/2009 Humayun et al.
2009/0240320 A1 9/2009 Tuval et al.
2009/0299469 A1 12/2009 Kollar
2009/0325030 A1 12/2009 Hamrock et al.
2010/0015200 A1 1/2010 Mcclain et al.
2010/0082094 A1 4/2010 Quadri et al.
2010/0114006 A1 5/2010 Baerveldt
2010/0114307 A1 5/2010 Agnew et al.
2010/0114309 A1 5/2010 De et al.
2010/0119580 A1 5/2010 Guo et al.
2010/0137981 A1 6/2010 Silvestrini et al.
2010/0161040 A1 6/2010 Braido et al.
2010/0168644 A1 7/2010 Brown
2010/0168839 A1 7/2010 Braido et al.
2010/0185138 A1 7/2010 Yaron et al.
2010/0185277 A1 7/2010 Braido et al.
2010/0234793 A1 9/2010 Dacey et al.
2010/0241046 A1 9/2010 Pinchuk et al.
2010/0241241 A1 9/2010 McKnight et al.
2010/0259748 A1 10/2010 Suzuki
2011/0027579 A1 2/2011 Tate
2011/0028918 A1 2/2011 Hartwell et al.
2011/0066098 A1 3/2011 Stergiopulos
2011/0098640 A1 4/2011 Horne et al.
2011/0112620 A1 5/2011 Du
2011/0118835 A1* 5/2011 Silvestrini ........... A61F 9/00781 623/6.14
2011/0196487 A1 8/2011 Badawi et al.
2011/0244014 A1 10/2011 Williams et al.
2011/0257738 A1 10/2011 Corbett et al.
2011/0270388 A9 11/2011 Stevens
2011/0275912 A1 11/2011 Boyden et al.
2011/0276128 A1 11/2011 Cao et al.
2011/0282440 A1 11/2011 Cao et al.
2011/0288635 A1 11/2011 Miller et al.
2012/0035525 A1 2/2012 Silvestrini
2012/0089073 A1 4/2012 Cunningham, Jr.
2012/0123315 A1 5/2012 Horvath et al.
2012/0123317 A1 5/2012 Horvath et al.
2012/0141914 A1 6/2012 Namba et al.
2012/0165720 A1 6/2012 Horvath et al.
2012/0197175 A1 8/2012 Horvath et al.
2012/0253453 A1 10/2012 Bruchman et al.
2012/0310137 A1 12/2012 Silvestrini
2012/0323315 A1 12/2012 Bruchman et al.
2013/0046379 A1 2/2013 Paolitto et al.
2013/0131577 A1 5/2013 Bronstein et al.
2013/0158381 A1 6/2013 Rickard
2013/0184810 A1 7/2013 Hall et al.
2013/0190868 A1 7/2013 Kahook et al.
2013/0211314 A1 8/2013 Venkatraman et al.
2013/0218081 A1 8/2013 Roth
2013/0226330 A1 8/2013 Sopori et al.
2013/0274691 A1 10/2013 De Juan, Jr. et al.
2013/0317413 A1* 11/2013 Field ................ A61M 5/14276 604/9
2013/0325024 A1 12/2013 Nissan et al.
2013/0325111 A1 12/2013 Campbell et al.
2014/0012371 A1 1/2014 Li
2014/0031927 A1 1/2014 Bruchman et al.
2014/0039468 A1 2/2014 Dunn
2014/0107776 A1 4/2014 Williamson et al.
2014/0114226 A1 4/2014 Snyder et al.
2014/0128960 A1 5/2014 Greenslet et al.
2014/0154321 A1 6/2014 Ashton
2014/0170204 A1 6/2014 Desai et al.
2014/0186420 A1 7/2014 Utkhede et al.
2014/0214158 A1 7/2014 Board et al.
2014/0236067 A1* 8/2014 Horvath .............. A61F 9/00781 604/9
2014/0236068 A1 8/2014 Van et al.
2014/0243729 A1 8/2014 Rynerson
2014/0343475 A1 11/2014 Smedley et al.
2014/0343476 A1 11/2014 Penhasi
2014/0358224 A1 12/2014 Tegels et al.
2015/0005689 A1 1/2015 Horvath et al.
2015/0057595 A1 2/2015 Gunn et al.
2015/0119980 A1 4/2015 Beith et al.
2015/0224200 A1 8/2015 De Juan, Jr. et al.
2015/0224231 A1 8/2015 Bruchman et al.
2015/0320975 A1 11/2015 Simpson et al.
2015/0342875 A1 12/2015 Haffner
2015/0374545 A1 12/2015 Horvath et al.
2016/0000602 A1 1/2016 Meng et al.
2016/0015516 A1 1/2016 Bernstein et al.
2016/0038412 A1 2/2016 Guo et al.
2016/0058615 A1 3/2016 Camras et al.
2016/0058616 A1 3/2016 Camras et al.
2016/0067032 A1 3/2016 Soletti et al.
2016/0067093 A1 3/2016 Johnson et al.
2016/0100939 A1 4/2016 Armstrong et al.
2016/0153591 A1 6/2016 Fonfara et al.
2016/0242962 A1 8/2016 Torello et al.
2016/0245432 A1 8/2016 Fonfara et al.
2016/0256321 A1* 9/2016 Horvath .............. A61F 9/00781
2016/0256382 A1 9/2016 Shi et al.
2016/0270958 A1 9/2016 De et al.
2016/0287513 A1 10/2016 Rakic et al.
2016/0296322 A1 10/2016 Edelman et al.
2016/0302965 A1 10/2016 Erickson et al.
2016/0302967 A1 10/2016 Ahn

(56) References Cited

U.S. PATENT DOCUMENTS

| | | | |
|---|---|---|---|
| 2016/0331528 | A1 | 11/2016 | Parker et al. |
| 2016/0374856 | A1 | 12/2016 | Pinchuk et al. |
| 2017/0000610 | A1 | 1/2017 | Eppihimer et al. |
| 2017/0014227 | A1 | 1/2017 | Boden et al. |
| 2017/0020731 | A1 | 1/2017 | Baerveldt |
| 2017/0071729 | A1 | 3/2017 | Wrobel |
| 2017/0079779 | A1 | 3/2017 | Tabor |
| 2017/0079782 | A1 | 3/2017 | Beith |
| 2017/0092974 | A1 | 3/2017 | Macphee |
| 2017/0141423 | A1 | 5/2017 | Okada et al. |
| 2017/0156854 | A1 | 6/2017 | Hammer |
| 2017/0172794 | A1 | 6/2017 | Varner et al. |
| 2017/0189175 | A1 | 7/2017 | Justino et al. |
| 2017/0245989 | A1 | 8/2017 | Bluestein et al. |
| 2017/0252156 | A1 | 9/2017 | Bernstein et al. |
| 2017/0296783 | A1 | 10/2017 | Connolly et al. |
| 2017/0367888 | A1 | 12/2017 | Brown |
| 2018/0028361 | A1 | 2/2018 | Haffner et al. |
| 2018/0049872 | A1 | 2/2018 | Bennett |
| 2018/0071143 | A1 | 3/2018 | Silvestrini et al. |
| 2018/0110650 | A1 | 4/2018 | Da Silva Curiel et al. |
| 2018/0125632 | A1 | 5/2018 | Cully et al. |
| 2018/0126134 | A1 | 5/2018 | Cully et al. |
| 2018/0133002 | A1 | 5/2018 | Yi et al. |
| 2018/0133149 | A1 | 5/2018 | Zilberman |
| 2018/0177592 | A1 | 6/2018 | Benichou et al. |
| 2018/0185151 | A1 | 7/2018 | Bishop |
| 2018/0263718 | A1 | 9/2018 | Griffiths et al. |
| 2018/0263775 | A1 | 9/2018 | Shah |
| 2018/0263817 | A1 | 9/2018 | Roeber et al. |
| 2018/0263818 | A1 | 9/2018 | Roeber et al. |
| 2018/0263819 | A1 | 9/2018 | Roeber et al. |
| 2018/0303752 | A1 | 10/2018 | Haffner |
| 2018/0325732 | A1 | 11/2018 | Burns et al. |
| 2018/0344457 | A1 | 12/2018 | Gross et al. |
| 2018/0344526 | A1 | 12/2018 | Pinchuk |
| 2019/0000673 | A1 | 1/2019 | Fjield et al. |
| 2019/0015191 | A1 | 1/2019 | Berdajs |
| 2019/0046696 | A1 | 2/2019 | Parikh et al. |
| 2019/0091014 | A1 | 3/2019 | Arcaro et al. |
| 2019/0091015 | A1 | 3/2019 | Dienno et al. |
| 2019/0105199 | A1 | 4/2019 | Ahmed et al. |
| 2019/0125529 | A1 | 5/2019 | Colavito et al. |
| 2019/0125530 | A1 | 5/2019 | Arcaro et al. |
| 2019/0125531 | A1 | 5/2019 | Bennett et al. |
| 2019/0133826 | A1 | 5/2019 | Horvath et al. |
| 2019/0167475 | A1 | 6/2019 | Horvath et al. |
| 2019/0224047 | A1 | 7/2019 | Kao et al. |
| 2019/0282360 | A1 | 9/2019 | Colavito et al. |
| 2019/0298572 | A1 | 10/2019 | Chu |
| 2019/0343617 | A1 | 11/2019 | Sobrino-Serrano et al. |
| 2019/0365531 | A1 | 12/2019 | Beith |
| 2020/0113681 | A1 | 4/2020 | Armstrong et al. |
| 2020/0121454 | A1 | 4/2020 | Spence |
| 2020/0188114 | A1 | 6/2020 | Radspinner et al. |
| 2020/0188147 | A1 | 6/2020 | Throckmorton et al. |
| 2020/0214886 | A1 | 7/2020 | Gutierrez |
| 2020/0214887 | A1 | 7/2020 | Gutierrez |
| 2020/0229977 | A1 | 7/2020 | Mixter et al. |
| 2020/0330377 | A1 | 10/2020 | Banerjee et al. |
| 2020/0337897 | A1 | 10/2020 | Sacherman et al. |
| 2021/0205130 | A1 | 7/2021 | Campbell et al. |
| 2021/0315806 | A1 | 10/2021 | Haffner |
| 2021/0322217 | A1 | 10/2021 | Roeber et al. |
| 2021/0346197 | A1 | 11/2021 | Roeber et al. |
| 2022/0080049 | A1 | 3/2022 | Garcia et al. |
| 2022/0354996 | A1 | 11/2022 | Engman et al. |
| 2022/0378611 | A1 | 12/2022 | Conia et al. |
| 2022/0395397 | A1 | 12/2022 | Chu |
| 2023/0054622 | A1 | 2/2023 | Roeber et al. |
| 2023/0117758 | A1 | 4/2023 | Roeber et al. |
| 2023/0142430 | A1 | 5/2023 | Towler et al. |
| 2023/0142433 | A1 | 5/2023 | Towler et al. |
| 2023/0218286 | A1 | 7/2023 | McAlister et al. |
| 2024/0041645 | A1 | 2/2024 | Conia et al. |

FOREIGN PATENT DOCUMENTS

| | | | |
|---|---|---|---|
| AU | 2015266850 | A1 | 12/2016 |
| AU | 2020201236 | A1 | 3/2020 |
| AU | 2017439185 | A1 | 5/2020 |
| AU | 2021218010 | A1 | 9/2021 |
| CA | 2502761 | A1 | 4/1997 |
| CA | 2974600 | A1 | 10/2015 |
| CA | 2950187 | A1 | 12/2015 |
| CN | 1208602 | A | 2/1999 |
| CN | 2414757 | Y | 1/2001 |
| CN | 1285724 | A | 2/2001 |
| CN | 1425826 | A | 6/2003 |
| CN | 1592640 | A | 3/2005 |
| CN | 1976732 | A | 6/2007 |
| CN | 101965211 | A | 2/2011 |
| CN | 202619978 | U | 12/2012 |
| CN | 103179927 | A | 6/2013 |
| CN | 103619366 | A | 3/2014 |
| CN | 104000684 | A | 8/2014 |
| CN | 104114201 | A | 10/2014 |
| CN | 104168863 | A | 11/2014 |
| CN | 105377202 | A | 3/2016 |
| CN | 105579001 | A | 5/2016 |
| CN | 205198254 | U | 5/2016 |
| CN | 107613917 | A | 1/2018 |
| EP | 2226624 | A1 | 9/2010 |
| EP | 2472297 | A1 | 7/2012 |
| EP | 2349147 | B1 | 3/2015 |
| EP | 2958530 | A1 | 12/2015 |
| EP | 3148491 | A1 | 4/2017 |
| EP | 3677229 | A1 | 7/2020 |
| EP | 3773377 | A1 | 2/2021 |
| GB | 2513194 | A | 10/2014 |
| JP | 08-117267 | A | 5/1996 |
| JP | 11-505159 | A | 5/1999 |
| JP | 2000-513248 | A | 10/2000 |
| JP | 2002-521145 | A | 7/2002 |
| JP | 2003-301948 | A | 10/2003 |
| JP | 2005-500101 | A | 1/2005 |
| JP | 2005-121438 | A | 5/2005 |
| JP | 2005-294016 | A | 10/2005 |
| JP | 2007-521125 | | 8/2007 |
| JP | 2008-101926 | A | 5/2008 |
| JP | 2010-540079 | A | 12/2010 |
| JP | 2011-504127 | A | 2/2011 |
| JP | 2011-507631 | A | 3/2011 |
| JP | 2012-504031 | A | 2/2012 |
| JP | 2012-164647 | A | 8/2012 |
| JP | 2013-009982 | A | 1/2013 |
| JP | 2014-517720 | A | 7/2014 |
| JP | 2014-199348 | A | 10/2014 |
| JP | 2014-239034 | A | 12/2014 |
| JP | 2015-039515 | A | 3/2015 |
| JP | 2015-175815 | A | 10/2015 |
| JP | 2016-137278 | A | 8/2016 |
| JP | 2017-517363 | A | 6/2017 |
| JP | 6655610 | B2 | 2/2020 |
| JP | 2020-075162 | A | 5/2020 |
| JP | 6872650 | B2 | 5/2021 |
| JP | 2021-112598 | A | 8/2021 |
| KR | 10-2008-0020259 | A | 3/2008 |
| KR | 10-2016-0026107 | A | 3/2016 |
| WO | 2001/066037 | A2 | 9/2001 |
| WO | 02/00318 | A1 | 1/2002 |
| WO | 2002/100318 | A2 | 12/2002 |
| WO | 2003/007795 | A2 | 1/2003 |
| WO | 03/15659 | A2 | 2/2003 |
| WO | 2005/076973 | A2 | 8/2005 |
| WO | 2007/100408 | A2 | 9/2007 |
| WO | 2008/030246 | A2 | 3/2008 |
| WO | 2008/030951 | A2 | 3/2008 |
| WO | 2008/133852 | A1 | 11/2008 |
| WO | 2009/042196 | A2 | 4/2009 |
| WO | 2009/137785 | A2 | 11/2009 |
| WO | 2010/037141 | A1 | 4/2010 |
| WO | 2011/147849 | A1 | 12/2011 |
| WO | 2012/018779 | A2 | 2/2012 |
| WO | 2012/135603 | A2 | 10/2012 |

(56) References Cited

FOREIGN PATENT DOCUMENTS

| | | | |
|---|---|---|---|
| WO | 2012/142318 | A1 | 10/2012 |
| WO | 2013/090006 | A1 | 6/2013 |
| WO | 2013/096854 | A3 | 8/2013 |
| WO | 2014/028725 | A1 | 2/2014 |
| WO | 2014/130574 | A1 | 8/2014 |
| WO | 2014/145811 | A1 | 9/2014 |
| WO | 2015/064312 | A1 | 5/2015 |
| WO | 2015/065646 | A1 | 5/2015 |
| WO | 2015/085234 | A1 | 6/2015 |
| WO | 2015/126332 | A1 | 8/2015 |
| WO | 2015/184173 | A1 | 12/2015 |
| WO | 2016/033270 | A1 | 3/2016 |
| WO | 2016/168686 | A1 | 10/2016 |
| WO | 2016/196841 | A1 | 12/2016 |
| WO | 2017/156293 | A1 | 9/2017 |
| WO | 2017/176886 | A1 | 10/2017 |
| WO | 2018/150392 | A1 | 8/2018 |
| WO | 2018/170429 | A1 | 9/2018 |
| WO | 2018/170433 | A1 | 9/2018 |
| WO | 2018/187714 | A1 | 10/2018 |
| WO | 2019/018807 | A1 | 1/2019 |
| WO | 2019/094004 | A1 | 5/2019 |
| WO | 2019/154927 | A1 | 8/2019 |
| WO | 2020/047221 | A1 | 3/2020 |
| WO | 2020/047222 | A1 | 3/2020 |
| WO | 2020/223525 | A1 | 11/2020 |

OTHER PUBLICATIONS

Gedde et al., "Treatment Outcomes in the Tube Versus Trabeculectomy (TVT) Study After Five Years of Follow-up", Am J Ophthalmol., vol. 153, No. 5, 2012, pp. 789-803.

Han, et al. "Membrane-tube-type glaucoma shunt device for refractory glaucoma surgery", Glaucoma, Graefes Arch Clin Exp Opthalmol, DOI 10, 1007/s00417-016-3510-z. Springer-Verlag Berlin Heidelberg 2016.

International Preliminary Report on Patenlability received for PCT Patent Application No. PCT/US2018/022929, mailed on Sep. 26, 2019, 9 pages.

International Preliminary Report on Patentability received for PCT Patent Application No. PCT/US2018/022922, mailed on Sep. 26, 2019, 9 pages.

International Preliminary Report on Patentability received for PCT Patent Application No. PCT/US2018/022933, mailed on Sep. 26, 2019, 9 pages.

International Search Report dated Jul. 23, 2018 for PCT/US2018/022922.

International Search Report of PCT/2018/022933 dated Jul. 3, 2018.

International Search Report of PCT/US2018/022929 dated Jun. 28, 2018.

Karthikeyan et al., "The concept of ocular inserts as drug delivery systems: An overview", Asian Journal Of Pharmaceutics, vol. 2, No. 4, 2008, pp. 192-200.

Lee et al., "Aqueous-Venous Shunt for Glaucoma a Further Report", Arch Opthalmol, vol. 99, 1981, pp. 2007-2012.

Lee et al., "Aqueous-Venous Shunt in The Rabbit Eye: A Long-Term Follow-Up", Trans. Soc. Ophthal. Sin., vol. 8, 1969, pp. 7-24.

Lee et al., "Aqueous-Venus Shunt for Glaucoma: Report on 15 cases", AnnalOphthal, Oct. 1974, pp. 1083-1088.

Lee et al., "Effect of an Aqueous-Venous Shunt in the Monkey Eye", Canad. J. Ophthal., 3:22, 1968, pp. 22-27.

Lee et al., "Effect of aqueous-venous shunt on rabbit eyes", Inivestigative Ophthalmology, vol. 5, No. 3, 1996, pp. 304-311.

Lee et al., "Glaucoma Microsurgery Aqueous-Venous Shunt Procedure", International Surgery, vol. 57, No. 1, Jan. 1972, pp. 37-41.

Miyazaki, et al., Expanded polytetrafluoroethylene conduits and patches with bulging sinuses and fan-shaped valves in right ventricular outflow tract reconstruction: Multicneter study in Japan. The Journal of Thoracic and Cardiovascular Surgery, Nov. 2011, vol. 142, No. 5, pp. 1122-1129.

Ootaki et al., Medium-term outcomes after implantation of expanded polytetrafluoroethylene valved conduit. The Annals of Thoracic Surgery, 2018; 105 (3), pp. 843-850.

Rese et al., "Sustained drug delivery in glaucoma", Current Opinion in Ophthalmology, vol. 25, No. 2, 2014, pp. 112-117.

Shinkawa et al., Valved polytetrafluoroethylene conduits for right ventricular outflow tract reconstruction. The Annals of Thoracic Surgery. Jul. 2015; 100(1), pp. 129-137.

Stevenson et al., "Reservoir-Based Drug Delivery Systems Utilizing Microtechnology", Advanced Drug Delivery Reviews, vol. 64, No. 14, 2012, pp. 1590-1602.

Understanding Your Heart Valve. Medtronic USA, Inc., 2006. Pamphlet.

Yamagishi et al. Outflow reconstruction of tetralogy of fallot using a Gore-Tex valve. The Anais of Thoracic Surgery, Dec. 1993; 56(6), pp. 1414-1417.

"Ahmed(Registered) ClearPath Glaucoma Drainage Device Model CP250 and CP350," New World Medical, Inc., Part # 50-0109, pp. 28. Downloaded Mar. 6, 2020.

"The Ahmed Giaucoma Valve Model FP7," New World Medical, Inc., Part #50-0088 Rev C, URL: https://www.newworldmedical.com/wp-content/uploads/2020/07/AGV-FP7-IFU-50-0088-Rev-C.pdf, Nov. 2019, pp. 1-28.

International Search Report and Written Opinion received for PCT Patent Application No. PCT/US2023/010660, mailed on May 24, 2023, 17 pages.

International Search Report and Written Opinion received for PCT Patent Application No. PCT/US2022/031305, mailed on Nov. 7, 2022, 26 pages.

Kahook et al., "Location of glaucoma drainage devices relative to the optic nerve," British Journal of Ophthalmol, vol. 90, No. 8, Aug. 2006, pp. 1010-1013.

McMenamin et al., "Normal anatomy of the aqueous humour outflow system in the domestic pig eye," Journal of Anatomy, vol. 178, Oct. 1991, pp. 65-77.

Molteno, Anthony C.B., "Molteno3 Glaucoma Drainage Device," Surgical Guide, 0817-SG/GDD, Molteno, 2006, p. 44.

Palioura S. et al., "Role of steroids in the treatment of bacterial keratitis," Clinical Ophthalmology. vol. 10, Jan. 27, 2016, pp. 179-186.

Plemel et al., "Tube shunt surgery in pig eyes: a wet lab teaching model," Canadian Journal of Ophthalmology, vol. 54, Issue 5, Oct. 2019, pp. 585-589.

Mohammadi et al., "Sheep practice eye for ophthalmic surgery training in skills Laboratory," Journal of Cataract and Refractive Surgery, vol. 37, No. 6, Jun. 2011, pp. 987-991.

Shastri, V et. al. Non-Degradable Biocompatible Polymers in Medicine: Past, Present, and Future. Current Pharmaceutical Biotechnology, vol. 4, No. 5, 2003, pp. 331-337 [online], [retrieved on Nov. 8, 2023], Retrieved from the Internet <URL: https://pubmed.ncbi.nlm.nih.gov/14529423/> (Year: 2003).

Wadhawan, A et. al. Gore-tex® versus resolut adapt® GTR membranes with perioglas® in periodontal regeneration. Contemp. Clin. Dent., vol. 3, No. 4, Oct.-Dec. 2012, pp. 406-411 [online], [retrieved on Nov. 8, 2023], Retrieved from the Internet <URL: https://www.ncbi.nlm.nih.gov/pmc/articles/PMC3636825/> (Year: 2012).

Doble, M., Makadia, N., Pavithran, S., & Kumar, R. S. (2008). Analysis of explanted ePTFE cardiovascular grafts (modified BT shunt). Biomedical Materials, 3(3), 034118. (Year: 2008).

International Preliminary Report on Patentability received for PCT Patent Application No. PCT/US19/48759, mailed on Mar. 11, 2021, 12 pages.

International Preliminary Report on Patentability received for PCT Patent Application No. PCT/US19/48760, mailed on Mar. 11, 2021, 9 pages.

International Preliminary Report on Patentability received for PCT Patent Application No. PCT/US2015/055348, dated Apr. 27, 2017, 18 pages.

International Preliminary Report on Patentability received for PCT Patent Application No. PCT/US2019/065890, mailed on Jun. 24, 2021, 8 pages.

(56) References Cited

OTHER PUBLICATIONS

International Preliminary Report on Patentability received for PCT Patent Application No. PCT/US2022/031305, mailed on Dec. 7, 2023, 18 pages.
International Preliminary Report on Patentability received for PCT Patent Application No. PCT/US2023/010660, mailed on Jul. 25, 2024, 10 pages.
International Preliminary Report on Patentability received for PCT Patent Application No. PCT/US22/48960, mailed on May 16, 2024, 10 pages.
International Search Report and Written Opinion received for PCT Patent Application No. PCT/US19/48759, mailed on Feb. 12, 2020, 16 pages.
International Search Report and Written Opinion received for PCT Patent Application No. PCT/US19/48760, mailed on Dec. 3, 2019, 11 pages.
International Search Report and Written Opinion received for PCT Patent Application No. PCT/US2015/055348, mailed on Apr. 11, 2016, 23 pages.
International Search Report and Written Opinion received for PCT Patent Application No. PCT/US2018/050771, mailed on Feb. 25, 2019, 16 pages.
International Search Report and Written Opinion received for PCT Patent Application No. PCT/US2019/065890, dated Mar. 18, 2020, 9 pages.
International Search Report and Written Opinion received for PCT Patent Application No. PCT/US2022/048960, mailed on Mar. 2, 2023, 17 pages.
International Search Report and Written Opinion received for PCT Patent Application No. PCT/US2022/048971, mailed on Apr. 24, 2023, 19 pages.
International Search Report and Written Opinion received for PCT Patent Application No. PCT/US2023/029614, mailed on Nov. 10, 2023, 13 pages.
Invitation to pay additional fees received for PCT Patent Application No. PCT/US19/48759, mailed on Dec. 11, 2019, 10 pages.
Invitation to pay additional fees received for PCT Patent Application No. PCT/US22/31305, mailed on Sep. 15, 2022, 23 pages.
Lee et al., "Pig eye trabeculectomy-a wet-lab teaching model," Eye, vol. 20, Jan. 28, 2005, pp. 32-37.
Miyazaki, et al., Expanded polytetrafluoroethylene valved conduit and patch with bulging sinuses in right ventricular outflow tract reconstruction. The Journal of Thoracic and Cardiovascular Surgery, Aug. 2007, vol. 134, No. 2, pp. 327-332.
Office Action received for Chinese Patent Application No. 202110966241.1, mailed on May 15, 2024, 11 pages (5 pages of English Translation and 6 pages of Original Document).
Tang, H., Zhang, Y., Wang, F., Zhang, H., & Guo, Y. (2016). Long-term stability of polytetrafluoroethylene (PTFE) hollow fiber membranes for CO2 capture. Energy & Fuels, 30(1), 492-503. (Year: 2019).

* cited by examiner

GLAUCOMA TREATMENT SYSTEMS AND METHODS

CROSS-REFERENCE TO RELATED APPLICATION

This application is a continuation of U.S. application Ser. No. 15/922,701, filed Mar. 15, 2018, which claims the benefit of Provisional Application No. 62/473,090, filed Mar. 17, 2017, which is incorporated herein by reference in its entirety. This application also relates to an application titled "DELIVERY AIDS FOR GLAUCOMA SHUNTS," filed on the same day as this application, Mar. 15, 2018, which is incorporated herein by reference in its entirety. This application also relates to an application titled "INTEGRATED AQUEOUS SHUNT FOR GLAUCOMA TREATMENT," filed on the same day as this application, Mar. 15, 2018, which is incorporated herein by reference in its entirety.

BACKGROUND

Aqueous humor is a fluid that fills the anterior chambers of the eye and contributes to the intraocular pressure or fluid pressure inside the eye. Glaucoma is a progressive disease of the eye characterized by an increase of the eye's intraocular pressure. This increase in intraocular pressure is commonly caused by an insufficient amount of aqueous humor being reabsorbed by the body. In some cases, the aqueous humor is not absorbed fast enough or even at all, while in other cases, the aqueous humor is additionally or alternatively being produced too quickly. An increase in intraocular pressure is associated with a gradual and sometimes permanent loss of vision in the afflicted eye.

A number of attempts have been made to treat glaucoma. However, some of the conventional devices lack the flexibility, conformity, and device/tissue attachment that is required to avoid relative movement between the device and the surrounding tissue. Such movement can lead to persistent irritation of the surrounding tissue. Irritation, in turn, can lead to an augmented chronic inflammatory tissue response, excessive scar formation at the device site, and a heightened risk of device erosion through the conjunctiva and endophthalmitis. In instances where erosion does not occur, the scar tissue effectively prevents reabsorption of the aqueous humor. These complications can serve to prevent proper functioning of the device. The resulting effect is a gradual increase in intraocular pressure and progression of glaucoma.

SUMMARY

According to one example, ("Example 1"), a biological fluid drainage system includes a compliant fluid conduit including a lumen, the fluid conduit being reconfigurable from a first post-operative configuration to a second post-operative configuration, the fluid conduit being implantable to facilitate evacuation of a fluid from within a fluid reservoir of a biological tissue to a region exterior to the fluid reservoir of the biological tissue, wherein in the first post-operative configuration the fluid conduit has a first length and is operable to regulate flow through the lumen to a first flow rate, and wherein in the second post-operative configuration the fluid conduit has a second length different from the first length and is operable regulate flow through the lumen to a second flow rate different from the first flow rate.

According to another example, ("Example 2") further to Example 1, a pressure drop across the fluid conduit in the second post-operative configuration is less than a pressure drop across the fluid conduit in the first post-operative configuration.

According to another example, ("Example 3") further to any of Examples 1 and 2, the fluid conduit is configured to be modified by cutting away a third length of the fluid conduit, wherein the cut away third length corresponds in length to the difference in length between the first length of the fluid conduit in the first post-operative configuration and the second length of the fluid conduit in the second post-operative configuration.

According to another example, ("Example 4") further to any of the preceding Examples, a first section of the first length of the fluid conduit is coiled within the fluid reservoir of the biological tissue.

According to another example, ("Example 5") further to any of the preceding Examples a second section of the first length of the fluid conduit is coiled within an interior of a microporous body coupled to the fluid conduit.

According to another example, ("Example 6") further to Example 5, the second section of the first length of the fluid conduit is helically coiled within the interior of the microporous body.

According to another example, ("Example 7") further to any of Examples 5 to 6, the fluid conduit is configured to slide relative to the microporous body.

According to another example, ("Example 8") further to any of the preceding Examples, the fluid conduit extends within an interior of the sleeve and is configured to slide relative to the sleeve.

According to another example, ("Example 9") further to Example 8, the sleeve is coupled to the microporous body.

According to another example, ("Example 10") further to any of the preceding Examples, the lumen of the fluid conduit is tapered such that an average diameter of the fluid conduit along the first length of the fluid conduit in the first post-operative configuration is greater than an average diameter of the fluid conduit along the second length of the fluid conduit in the second post-operative configuration.

According to another example, ("Example 11") further to any of the preceding Examples, the fluid conduit includes a plurality of lumens including a first lumen having a first lumen length and a second lumen having a second lumen length, and wherein in the first post-operative configuration the fluid conduit is configured to allow fluid to flow through the first lumen and not the second lumen, and wherein in the second post-operative configuration the fluid conduit is configured to allow fluid to flow through the second lumen.

According to another example, ("Example 12") further to Example 11, in the first post-operative configuration a second flow adjuster is associated with the second lumen, wherein the second flow adjuster operates to restrict fluid flow through the second lumen.

According to another example, ("Example 13") further to Example 11, in the second post-operative configuration a first flow adjuster is associated with the first lumen, wherein the first flow adjuster operates to restrict fluid flow through the first lumen.

According to another example, ("Example 14") further to 13, in the second post-operative configuration the first flow adjuster operates to prohibit fluid flow through the first lumen.

According to another example, ("Example 15") further to Examples 11 to 13, in the second post-operative configuration the fluid conduit is configured to allow fluid to flow through both the first lumen and the second lumen.

According to another example, ("Example 16") further to any of Examples 13 to 15, the first flow adjuster and the second flow adjuster operate according to different mechanisms to resist fluid flow through the first and second lumens, respectively.

According to another example, ("Example 17") further to any of Examples 13 to 16, the first and second flow adjusters are independently post-operatively modifiable.

According to another example, ("Example 18") further to any of Examples 11 to 17, the fluid conduit includes a plurality of individual tubes, the plurality of individual tubes including the plurality of lumens.

According to another example, ("Example 19") further to Example 18, the plurality of individual tubes are bundled together to collectively define the fluid conduit.

According to another example, ("Example 20") further to any of the preceding Examples, biological fluid drainage system operates to regulate an intraocular pressure of a patient's eye.

According to another example, ("Example 21") further to Example 20, the fluid conduit is configured to facilitate aqueous humor evacuation from within an anterior chamber of a patient's eye when implanted.

According to another example, ("Example 22") further to any of the preceding Examples, the fluid conduit is post operatively modifiable through a clear corneal approach.

According to another example, ("Example 23") further to any of Examples 5 to 22, one of the fluid conduit and the microporous body comprises a fluoropolymer.

According to another example, ("Example 24") further to Example 23, the fluoropolymer is expanded polytetrafluoroethylene.

According to another example, ("Example 25") further to any of Examples 12 to 24, the second flow adjuster is a porous element that is permeable to fluid.

According to another example, ("Example 26") further to any of Examples 12 to 24, the second flow adjuster is a non-porous insert that is configured to obstruct flow through the second lumen.

According to another example, ("Example 27") further to any of Examples 12 to 26, the second flow adjuster is removable.

According to another example, ("Example 28") further to any of Examples 12 to 27, the second flow adjuster is ablatable.

According to another example, ("Example 29") further to any of Examples 12 to 28, the second flow adjuster is replaceable with a third flow adjuster.

According to another example, ("Example 30") further to Example 29, the third flow adjuster is configured to decrease a flow rate through the second lumen relative to a flow rate through the lumen associated with the second flow adjuster.

According to another example, ("Example 31") further to Example 29, the third flow adjuster is configured to increase a flow rate through the second lumen relative to a flow rate through the lumen associated with the second flow adjuster.

According to another example, ("Example 32") further to any of Examples 12 to 31, the second flow adjuster is positioned interior to the second lumen of the fluid conduit.

According to another example, ("Example 33") further to any of Examples 12 to 31, the second flow adjuster is positioned exterior to the second lumen of the fluid conduit.

According to another example, ("Example 34") further to any of Examples 12 to 33, the second flow adjuster operates to constrict a diameter of the lumen of the fluid conduit.

According to another example, ("Example 35") further to any of Examples 12 to 34, the second flow adjuster extends along a portion of less than all of a length of the second lumen.

According to another example, ("Example 36") a fluid drainage system for controlling fluid pressure in an eye of a patient, the system includes a compliant fluid conduit suitable for implantation in the eye of a patient, the compliant fluid conduit configured to permit fluid evacuation from a fluid reservoir of the eye of the patient, a flow adjuster associated with the fluid conduit, the flow adjuster being modifiable to increase and decrease fluid flow through the fluid conduit.

According to another example, ("Example 37") further to Example 36, the flow adjuster includes a plurality of resistive elements, the flow adjuster being modifiable by replacing a first one of the plurality of resistive elements with a second one of the plurality of resistive elements wherein the second resistive element operates to increase fluid flow through the fluid conduit relative to the first resistive element.

According to another example, ("Example 38") further to Example 37, the flow adjuster is modifiable by replacing the second resistive element with a third one of the plurality of resistive elements wherein the third resistive element operates to increase fluid flow through the fluid conduit relative to the second resistive element.

According to another example, ("Example 39") further to Example 37, the flow adjuster is modifiable by replacing the second resistive element with a third one of the plurality of resistive elements wherein the third resistive element operates to decrease fluid flow through the fluid conduit relative to the second resistive element.

According to another example, ("Example 40") further to Example 36, the flow adjuster is modifiable by replacing the first resistive element with a second one of the plurality of resistive elements wherein the second resistive element operates to decrease fluid flow through the fluid conduit relative to the first resistive element.

According to another example, ("Example 41") further to any of Examples 36 to 40, the flow adjuster is selectively modifiable between at least three flow restriction configurations including a first restriction configuration restricting flow through the fluid conduit to a first flow rate, a second restriction configuration restricting flow through the fluid conduit to a second flow rate that is greater than the first flow rate, and a third restriction configuration restricting flow through the fluid conduit to a third flow rate that is less than the first flow rate.

According to another example, ("Example 42") further to any of Examples 37 to 41, the first resistive element is a porous resistive element that is permeable to fluid.

According to another example, ("Example 43") further to any of Examples 37 to 41, the first resistive element is a non-porous resistive element that is impermeable to fluid.

According to another example, ("Example 44") further to any of Examples 37 to 43, the second resistive element is a porous resistive element that is permeable to fluid.

According to another example, ("Example 45") further to any of Examples 37 to 43, the second resistive element is a non-porous resistive element that is impermeable to fluid.

According to another example, ("Example 46") further to any of Examples 37 to 45, the first resistive element is removable.

According to another example, ("Example 47") further to any of Examples 37 to 46, the first resistive element is ablatable.

According to another example, ("Example 48") further to any of Examples 37 to 47, at least one of the first and second resistive elements is positioned interior to a lumen of the fluid conduit.

According to another example, ("Example 49") further to any of Examples 37 to 48, at least one of the first and second resistive elements is positioned exterior to a lumen of the fluid conduit.

According to another example, ("Example 50") further to any of Examples 37 to 49, at least one of the first and second resistive elements operates to constrict a diameter of a lumen of the fluid conduit.

According to another example, ("Example 51") further to any of Examples 37 to 50, at least one of the first and second resistive elements extends along a portion of less than all of a length of the second lumen.

According to another example, ("Example 52") further to any of Examples 36 to 51, the system further includes a microporous body coupled to the fluid conduit.

According to another example, ("Example 53") further to Example 52, one of the fluid conduit and the microporous body comprises a fluoropolymer.

According to another example, ("Example 54") further to Example 53, the fluoropolymer is expanded polytetrafluoroethylene.

According to another example, ("Example 55") further to any of the preceding Examples, biological fluid drainage system operates to regulate an intraocular pressure of a patient's eye.

According to another example, ("Example 56") further to Example 55, the fluid conduit is configured to facilitate aqueous humor evacuation from within an anterior chamber of a patient's eye when implanted.

According to another example, ("Example 57") further to any of the preceding Examples, the fluid conduit is post operatively modifiable through a clear corneal approach.

According to another example, ("Example 58") a method includes providing a compliant fluid conduit; implanting the fluid conduit such that the fluid conduit is operable to facilitate evacuation of a fluid from within a fluid reservoir of a biological tissue to a region exterior to the fluid reservoir of the biological tissue, wherein the fluid conduit is operable to regulate a flow of fluid through the conduit to a first flow rate; and post-operatively modifying the fluid conduit by varying a length of the fluid conduit such that the fluid within the fluid reservoir of the biological tissue is operable to flow through the lumen of the fluid conduit at a second flow rate different from the first flow rate.

According to another example, ("Example 59") further to Example 58, post-operatively modifying the fluid conduit includes varying the length of the fluid conduit from a first length to a second length that is shorter than the first length.

According to another example, ("Example 60") further to any of Example 59, post-operatively modifying the element includes cutting away a section of the length of the fluid conduit.

According to another example, ("Example 61") further to Example 60, wherein a first portion of the length of the fluid conduit is coiled within the fluid reservoir of the biological tissue, and post-operatively modifying the fluid conduit includes cutting away a section of the length of the fluid conduit that is coiled within the fluid reservoir such that the first portion of the length of the fluid conduit that is coiled within the fluid reservoir is reduced.

According to another example, ("Example 62") further to any of Examples 58 to 61, a second portion of the length of the fluid conduit is coiled within an interior of a microporous body coupled to the fluid conduit, the fluid conduit being configured to slide relative to the microporous body, and wherein post-operatively modifying the fluid conduit includes: tensioning the fluid conduit to extend a length of the fluid conduit exterior to the microporous body from a first length to a second longer length; and cutting away a section of the fluid conduit exterior to the microporous body such that the length of the fluid conduit exterior to the microporous body has the first length and such that the second portion of the length of the fluid conduit coiled within the interior of the microporous body is reduced.

According to another example, ("Example 63") further to any of Examples 58 to 61, the fluid conduit includes a plurality of lumens including a first lumen having a first lumen length and a second lumen having a second lumen length, and wherein in a first post-operative configuration the fluid conduit is configured to allow fluid to flow through the first lumen and not the second lumen, and wherein post-operatively modifying the fluid conduit includes modifying the fluid conduit such that the fluid conduit is configured to allow fluid to flow through the second lumen.

According to another example, ("Example 64") further to Example 63, a flow adjuster operates to restrict fluid flow through the second lumen, and wherein post-operatively modifying the fluid conduit includes modifying the flow adjuster.

According to another example, ("Example 65") further to any of Examples 63 to 64, a flow adjuster operates to restrict fluid flow through the second lumen, and wherein post-operatively modifying the fluid conduit includes removing the flow adjuster.

According to another example, ("Example 66") further to any of Examples 63 to 65, post-operatively modifying the fluid conduit includes modifying the fluid conduit such that the fluid conduit is configured to allow fluid to flow through both the first lumen and the second lumen.

According to another example, ("Example 67") further to any of Examples 58 to 66, implanting the fluid conduit operates to regulate an intraocular pressure of a patient's eye and wherein post-operatively modifying the element operates to further regulate the intraocular pressure of the patient's eye.

According to another example, ("Example 68") further to Example 67, post-operatively modifying the element to further regulate the intraocular pressure of the patient's eye includes increasing the flow rate of fluid through the fluid conduit from the first flow rate to the second flow rate.

According to another example, ("Example 69") further to Example 67, post-operatively modifying the element to further regulate the intraocular pressure of the patient's eye includes reducing the flow rate of fluid through the fluid conduit from the first flow rate to the second flow rate.

According to another example, ("Example 70") further to any of Examples 58 to 69, the fluid conduit is configured to facilitate aqueous humor evacuation from within an anterior chamber of a patient's eye when implanted.

According to another example, ("Example 71") further to any of Examples 58 to 70, the element is post operatively modifiable through a clear corneal approach.

According to another example, ("Example 72") further to any of Examples 58 to 70, the element is post operatively ablatable using a laser.

According to another example, ("Example 73") further to any of Examples 58 to 72, a pressure drop across the fluid conduit after post-operatively modifying the element is less than a pressure drop across the fluid conduit prior to post-operatively modifying the element.

According to another example, ("Example 74") a method includes providing a compliant fluid conduit suitable for implantation in the eye of a patient, the compliant fluid conduit including a first flow adjuster associated with the fluid conduit and configured to permit fluid evacuation from a fluid reservoir of the eye of the patient at a first flow rate; removing the first flow adjuster; and replacing the first flow adjuster with a second different flow adjuster configured to permit fluid evacuation from the fluid reservoir of the eye of the patient at second flow rate.

According to another example, ("Example 75") further to Example 74, the second flow rate is greater than the first flow rate.

According to another example, ("Example 76") further to Example 74, the second flow rate is less than the first flow rate.

According to another example, ("Example 77") a method of treating glaucoma includes providing the system according to any of Examples 1 to 31; implanting the system to control an intraocular pressure of a patient's eye; and post-operatively modifying the element of the system according to any of Examples 1 to 31.

BRIEF DESCRIPTION OF THE DRAWINGS

The accompanying drawings are included to provide a further understanding of embodiments of the disclosure and are incorporated in and constitute a part of this specification, illustrate examples, and together with the description serve to explain the principles of the disclosure.

Figure 1:
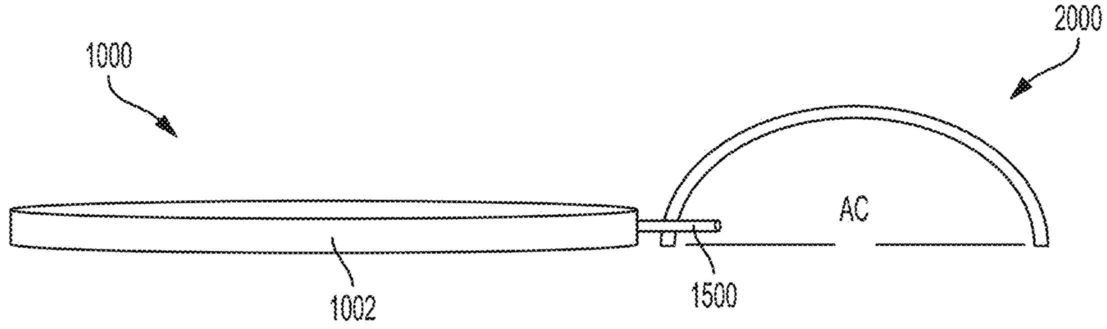
FIG. 1 is an illustration of a glaucoma drainage system consistent with various aspects of the present disclosure.

While multiple embodiments are disclosed, still other embodiments will become apparent to those skilled in the art from the following detailed description, which shows and describes illustrative examples. Accordingly, the drawings and detailed description are to be regarded as illustrative in nature and not restrictive.

DETAILED DESCRIPTION

Persons skilled in the art will readily appreciate that the various embodiments of the inventive concepts provided in the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting. As used herein, the term "diffusion membranes" is meant to encompass one or more proliferation diffusion membrane and/or one or more constriction diffusion membrane.

Various aspects of the present disclosure are directed toward glaucoma drainage devices, drainage systems, and drainage methods. More specifically, the present disclosure relates to devices, systems, and methods for draining aqueous humor from the anterior chamber of a patient's eye such that it may be reabsorbed by the body. Providing a mechanism for reabsorption of the aqueous humor that has been evacuated from the anterior chamber of the eye operates to lower or otherwise stabilize the intraocular pressure.

A glaucoma drainage system 1000 according to some embodiments is illustrated in FIG. 1. The glaucoma drainage system 1000 is an implantable medical system that operates to facilitate the drainage of a fluid, such as aqueous humor, from a fluid filled body cavity, such as the anterior chamber of the eye. The glaucoma drainage system 1000 includes a fluid conduit 1500 and a body, such as an aqueous humor diffusion member 1002. While the following disclosure refers to a glaucoma drainage system 1000 for use in draining aqueous humor from the anterior chamber of the eye, it is to be understood and appreciated by one of skill in the art that the glaucoma drainage system 1000 depicted can be configured and utilized to evacuate other fluids from other fluid filled body chambers. In some examples, as explained in greater detail below, the glaucoma drainage system 1000 additionally helps facilitate reabsorption of the evacuated fluid by the body. For instance, in some embodiments, the glaucoma drainage system 1000 provides an interface between the evacuated aqueous humor and tissues, vessels and/or cells that have the ability to absorb aqueous humor and are sufficiently proximate the glaucoma drainage system 1000 to interact with the evacuated aqueous humor. Thus, in some examples, aqueous humor evacuated from the anterior chamber of the eye travels through the glaucoma drainage system 1000 before being reabsorbed by the body.

In some embodiments, when the glaucoma drainage system 1000 is implanted, aqueous humor is evacuated from the anterior chamber through the fluid conduit 1500. The evacuated aqueous humor then enters a reservoir of the aqueous humor diffusion member 1002 and percolates through one or more porous membranes of the aqueous humor diffusion member 1002, where the aqueous humor can then be reabsorbed by the body. In various embodiments, in addition to aqueous humor permeability, tissue ingrowth is permitted or promoted along one or more regions of the glaucoma drainage system 1000. For instance, the exterior of the aqueous humor diffusion member 1002 may include or be defined by one or more membranes that are porous or otherwise permeable to the fluid of the fluid filled body cavity (referred to hereinafter as diffusion membranes), and that are configured to permit or promote tissue ingrowth. Permitting tissue ingrowth along surfaces or within regions of the glaucoma drainage system 1000 helps facilitate biointegration of the glaucoma drainage system 1000 into the surrounding tissue (e.g., eye tissue), and helps facilitate reabsorption of the evacuated aqueous humor by the surrounding tissue. Moreover, biointegration including tissue ingrowth and attachment helps minimize relative movement between the glaucoma drainage system 1000 and the tissue surrounding the glaucoma drainage system 1000, which helps avoid irritation of the eye tissue that can lead to foreign body tissue response, scar formation, and/or erosion and site infection of the glaucoma drainage system 1000.

In some embodiments, the fluid conduit of the glaucoma drainage system 1000 is a soft and compliant biocompatible tubular structure. In some embodiments, as discussed in greater detail below, the fluid conduit of the glaucoma drainage system 1000 includes one or more lumens and one or more resistive elements that can be selectively post-operatively removed or ablated through one or more minimally invasive procedures. That is, in some embodiments, the glaucoma drainage system 1000 includes a fluid conduit that comprises one or more lumens that are initially configured to resist fluid flow therethrough (e.g., such as due to the presence of a resistive element therein), but that are post-operatively modifiable such that fluid is allowed to flow through the one or more lumens previously resistant to flow. In various embodiments, these post-operative modifications to adjust a flow rate through the glaucoma drainage system 1000 can be performed minimally invasively without requiring removal and/or replacement of the glaucoma drainage system 1000. Thus, in some embodiments, these post-operative modifications can be performed outside of traditional operating rooms, such as in physician examination rooms.

In various embodiments, the aqueous humor diffusion member 1002 includes an interior region that defines a reservoir for the aqueous humor that is evacuated from the anterior chamber through the fluid conduit 1500. The interior region of the aqueous humor diffusion member 1002 may include one or more membranes that are porous or otherwise permeable to the fluid of the fluid filled body cavity (referred to hereinafter as diffusion membranes). For example, as discussed in greater detail below, one or more of the diffusion membranes may be formed of a porous media, such as a polymeric material, that has a microstructure that is suitable for transporting fluid through a pore space of the porous media. Thus, in some embodiments, the reservoir may be defined by the pore space of one or more of the diffusion membranes that form the aqueous humor diffusion member 1002. In some embodiments, the aqueous humor diffusion member 1002 may be configured such that the reservoir is additionally or alternatively defined between two or more of the diffusion membranes that form the aqueous humor diffusion member 1002. For instance, in some embodiments, at least a portion of the surface areas between adjacently situated diffusion membranes forming the aqueous humor diffusion member 1002 remains unbonded or unadhered such that the adjacently situated diffusion membranes are operable to separate from one another along at least a portion of their surface areas to form and define the reservoir. In some embodiments, as discussed further below, the reservoir defined between adjacently situated diffusion membranes is operable to inflate or dilate in a controlled manner (e.g., to a predetermined profile when inflated) so that the glaucoma drainage system 1000 does not interfere with normal eye function (e.g., regular eye movement, including pivoting and blinking).

In various embodiments, the aqueous humor diffusion member 1002 is sized and shaped such that it is implantable within the patient's anatomy. For instance, in some embodiments, the aqueous humor diffusion member 1002 is sized and shaped such that it is implantable within a dissected subconjunctival space (e.g., between a sclera and a conjunctiva of the patient's eye). In some embodiments, the aqueous humor diffusion member 1002 is a thin, circular-shaped member. In some embodiments, the aqueous humor diffusion member 1002 has a thickness (e.g., a distance measured between the first exterior surface 1004 and the second exterior surface 1006) of less than or equal to half of a millimeter (0.5 mm), such as between one-tenth of a millimeter (0.1 mm) and half of a millimeter (0.5 mm). However, given differing anatomies of the human body, an aqueous humor diffusion member 1002 may exceed of half of a millimeter (0.5 mm) provided that the thickness does not substantially interfere with normal eye functioning (e.g., pivoting and blinking) or substantially reduce the flexibility of the aqueous humor diffusion member 1002 to the extent that undesirable relative movement occurs between the glaucoma drainage system 1000 and the surrounding tissue when implanted, resulting with a likely consequence of tissue irritation, foreign body tissue response, and/or excessive scar formation.

In some embodiments, the aqueous humor diffusion member 1002 may have a diameter in the range of five (5) millimeters to fifteen (15) millimeters, such as ten (10) millimeters for example. In some embodiments, the aqueous humor diffusion member 1002 may be ovular and include a major dimension (e.g., along a major axis of the ellipse) of up to about thirty (30) millimeters and corresponding minor dimension (e.g., along a major axis of the ellipse) of up to about ten (10) millimeters. As discussed above, given differing anatomies of the human body, an aqueous humor diffusion member 1002 may exceed such dimensions (e.g., fifteen (15), and ten (10) and thirty (30) millimeters) provided that the size does not substantially interfere with normal eye functioning (e.g., pivoting and blinking) or substantially reduce the flexibility of the aqueous humor diffusion member undesirable relative movement occurs between the glaucoma drainage system 1000 and the surrounding tissue when implanted, resulting with a likely consequence of tissue irritation, foreign body tissue response, and/or excessive scar formation. Likewise, the aqueous humor diffusion member 1002 may have a diameter of less than five (5) millimeters, three (3) millimeters, or even less than three (3) millimeters provided that the aqueous humor diffusion member 1002 is operable to accommodate a sufficient degree of evacuated aqueous humor and is operable to facilitate the reabsorption of aqueous humor to constitute an effective treatment for the patient.

In various embodiments, the fluid conduit 1500 operates to fluidly couple the reservoir with the fluid filled body cavity (e.g., the anterior chamber of the eye) when implanted in the body such that a differential pressure is achievable between the reservoir and the environment exterior to the glaucoma drainage system 1000 (e.g., atmosphere). Thus, when implanted, it is to be appreciated that a pressure within the reservoir is based, at least in part, on the pressure within the fluid filled body cavity (e.g., the Intraocular Pressure of the Anterior Chamber of the eye). In some embodiments, such a differential pressure causes the reservoir to inflate or dilate. Moreover, in some embodiments, such a differential pressure causes the aqueous humor to percolate through the diffusion membranes of the aqueous humor diffusion member 1002. That is, in some embodiments, the evacuated aqueous humor enters the reservoir and percolates through the diffusion membranes of the aqueous humor diffusion member 1002, where the aqueous humor can then be reabsorbed by the body.

Figure 2A:
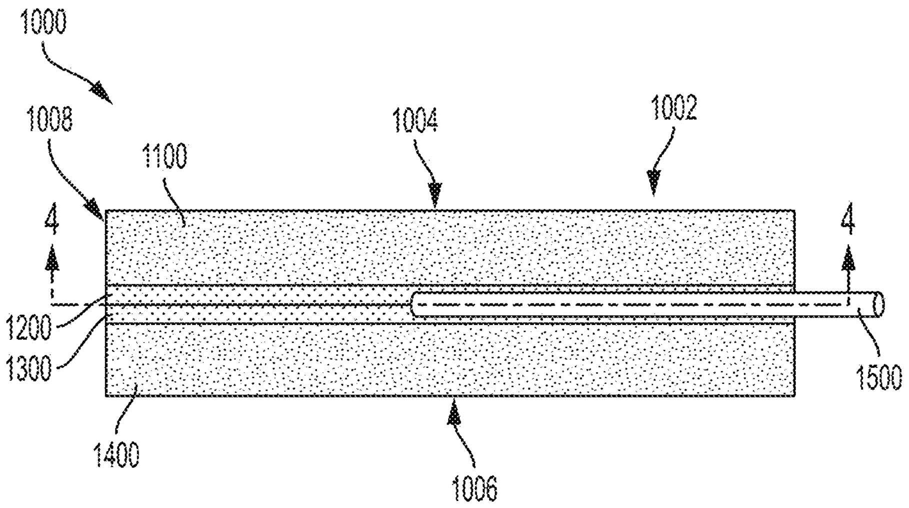
FIG. 2A is an illustration of a glaucoma drainage system in a deflated state consistent with various aspects of the present disclosure.
Figure 2B:
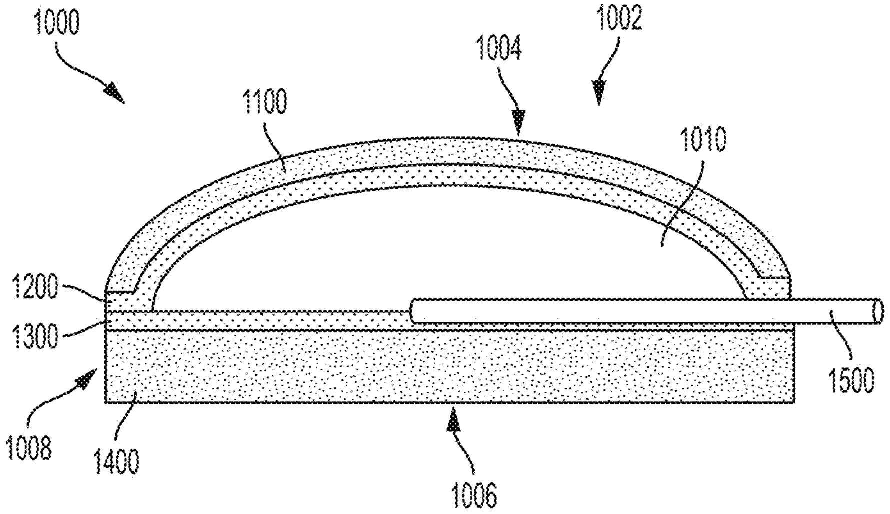
FIG. 2B is an illustration of a glaucoma drainage system in an inflated state consistent with various aspects of the present disclosure

Turning now to FIGS. 2A and 2B, a glaucoma drainage system 1000 including an aqueous humor diffusion member 1002 comprised of a plurality of diffusion membranes is shown. The aqueous humor diffusion member 1002 includes a first exterior surface 1004, a second, exterior surface 1006 opposing the first exterior surface 1004, and a periphery 1008. FIG. 2A shows the glaucoma drainage system 1000 in a deflated state. FIG. 2B shows the glaucoma drainage system 1000 in an inflated state, where aqueous humor is present within an inflatable or dilatable reservoir 1010. While the glaucoma drainage system 1000 is shown in FIG. 2B in an inflated state where the glaucoma drainage system 1000 is not uniformly inflated (e.g., the first proliferation and constriction diffusion membranes 1100 and 1200 are shown adopting a generally nonlinear configuration while the second proliferation and constriction diffusion membranes 1300 and 1400 are shown in a generally linear configuration), it is to be appreciated that the glaucoma drainage system 1000 may deform uniformly (e.g., the second proliferation and constriction diffusion membranes 1300 and 1400 may deform in a manner that mirrors the deformation of the first proliferation and constriction diffusion membranes 1100 and 1200). The aqueous humor diffusion member 1002 includes a body defined by a plurality of diffusion membranes including first and second proliferation diffusion membranes 1100 and 1400 and first and second constriction diffusion membranes 1200 and 1300. In some examples, the first and second proliferation diffusion membranes 1100 and 1400 and the first and second constriction diffusion membranes 1200 and 1300 are stacked upon one another as shown to form the aqueous humor diffusion member 1002. As discussed further below, the first and second proliferation diffusion membranes 1100 and 1400 are configured to permit tissue ingrowth and attachment, while the first and second constriction diffusion membranes 1200 and 1300 are configured to minimize, resist, or prevent tissue ingrowth and attachment.

In some embodiments, the first and second proliferation diffusion membranes 1100 and 1400 form or otherwise define an exterior of the aqueous humor diffusion member 1002, while the first and second constriction diffusion membranes 1200 and 1300 are situated between the first and second proliferation diffusion membranes 1100 and 1400 and define an interior region of the aqueous humor diffusion member 1002. In various embodiments, the first and second proliferation diffusion membranes 1100 and 1400 and the first and second constriction diffusion membranes 1200 and 1300 are each permeable to aqueous humor in that each is configured to allow evacuated aqueous humor (e.g., aqueous humor disposed within the sealed reservoir) to percolate therethrough and/or diffuse thereacross. However, the first and second proliferation diffusion membranes 1100 and 1400 are configured to permit tissue ingrowth and attachment, while the first and second constriction diffusion membranes 1200 and 1300 are configured to minimize, resist, or prevent tissue ingrowth and attachment. A configuration of constriction diffusion membranes sandwiched or otherwise situated between proliferation diffusion membranes as shown in FIGS. 2A and 2B helps to minimize, for instance, an ingress of bacteria in excess of the size of perforations or small holes present in the constriction diffusion membranes and/or migration thereof to the anterior chamber of the eye.

In various examples, the first and second proliferation diffusion membranes 1100 and 1400 of the aqueous humor diffusion member 1002 are microporous, permeable to aqueous humor, and are configured to permit the ingrowth and/or attachment of vessels and tissue. In various embodiments, the first and second constriction diffusion membranes 1200 and 1300 are also microporous and permeable to aqueous humor, but are configured resist or otherwise minimize the ingrowth and attachment of vessels and tissue structures. Thus, in various embodiments, the aqueous humor diffusion member 1002 is formed of a plurality of distinct diffusion membranes including at least a first proliferation diffusion membrane 1100 and at least a first constriction diffusion membrane 1200.

While the glaucoma drainage system 1000 shown in FIGS. 2A and 2B includes separate and distinct first and second proliferation diffusion membranes 1100 and 1400, it is to be appreciated that the aqueous humor diffusion member 1002 may include the first proliferation diffusion membrane 1100 without also requiring a separate and distinct second proliferation diffusion membrane 1400. For instance, the first proliferation diffusion membrane 1100 may be folded such that the first proliferation diffusion membrane 1100 surrounds the constriction diffusion membrane portion (e.g., the first and/or second constriction diffusion membranes 1200 and 1300) of the aqueous humor diffusion member 1002. In some such embodiments, one or more portions of the folded portion of the proliferation diffusion membrane 1100 is bonded or welded to adjacent portions of the non-folded portion of the proliferation diffusion membrane 1200 and/or one or more portions of the constriction diffusion membrane portion of the aqueous humor diffusion member 1002. Additionally or alternatively, while the glaucoma drainage system 1000 shown in FIGS. 2A and 2B includes separate and distinct first and second constriction diffusion membranes 1200 and 1300, it is to be appreciated that the aqueous humor diffusion member 1002 may include the first constriction diffusion membrane 1200 without also requiring a separate and distinct second constriction diffusion membrane 1300. For instance, the first constriction diffusion membrane 1200 may be folded over upon itself to form a multilayered constriction diffusion membrane, wherein one or more portions of the folded portion of the constriction diffusion membrane 1200 is bonded or welded to adjacent portions of the non-folded portion of the constriction diffusion membrane 1200. Moreover, a proliferation diffusion membrane 1100 may additionally be folded about the folded constriction diffusion membrane 1200, where the constriction diffusion membrane 1200 is folded over upon itself with a fluid conduit 1500 situated between the folded and unfolded portions of the constriction diffusion membrane 1200. In some such embodiments, a reservoir may be defined between at least the folded and unfolded portions of the constriction diffusion membrane 1200.

Figure 3:
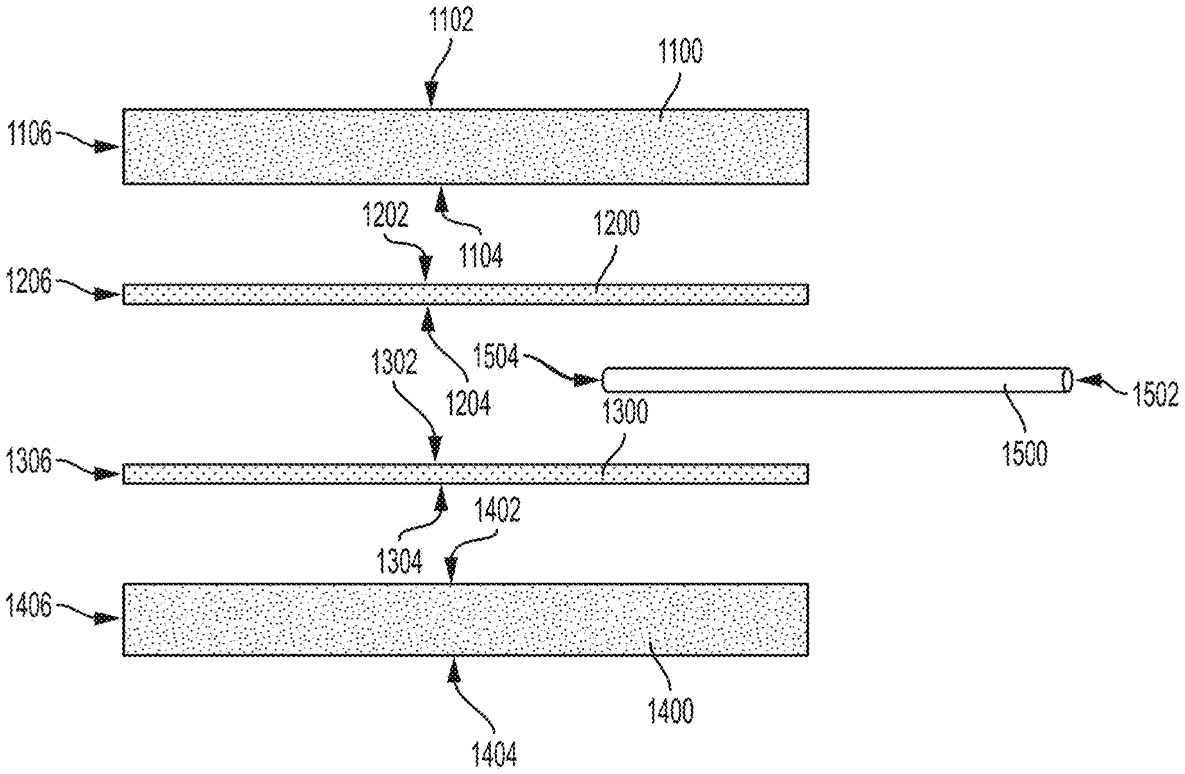
FIG. 3 is an exploded view of the glaucoma drainage system illustrated in FIG. 2.

FIG. 3 is an exploded view of the glaucoma drainage system 1000 shown in FIGS. 2A and 2B. As shown in FIG. 3, the aqueous humor diffusion member 1002 includes a body defined by a first proliferation diffusion membrane 1100, a first constriction diffusion membrane 1200, a second constriction diffusion membrane 1300, and a second proliferation diffusion membrane 1400. As shown, the various proliferation and constriction diffusion membranes each include interface surfaces and a periphery. For example, the first proliferation diffusion membrane 1100 includes a first interface surface 1102, a second interface surface 1104, and a periphery 1106. In some examples, the first interface surface 1102 of the first proliferation diffusion membrane 1100 corresponds with or otherwise defines the first exterior surface 1004 of the glaucoma drainage system 1000. Additionally, as shown in FIG. 3, first constriction diffusion membrane 1200 includes a first interface surface 1202, a second interface surface 1204, and a periphery 1206. Likewise, as shown in FIG. 3, second constriction diffusion membrane 1300 includes a first interface surface 1302, a second interface surface 1304, and a periphery 1306. As shown, the second proliferation diffusion membrane 1400 includes a first interface surface 1402, a second interface surface 1404, and a periphery 1406. In some examples, the second interface surface 1404 of the second proliferation diffusion membrane 1400 corresponds with or otherwise defines the second exterior surface 1006 of the glaucoma drainage system 1000.

In various embodiments, the diffusion membranes (i.e., the proliferation diffusion membranes and the constriction diffusion membranes) forming the aqueous humor diffusion member 1002 are situated adjacent to one another in a stacked configuration. For example, as illustrated in FIGS. 2A, 2B, and 3, the first and second proliferation diffusion membranes 1100 and 1400 and first and second constriction diffusion membranes 1200 and 1300 are situated adjacent to one another in a stacked configuration, with the first and second proliferation diffusion membranes 1100 and 1400 forming or otherwise defining an exterior of the aqueous humor diffusion member 1002, and with the first and second constriction diffusion membranes 1200 and 1300 sandwiched or otherwise situated between the first and second proliferation diffusion membranes 1100 and 1400. Thus, the proliferation diffusion membranes forming the exterior region of the aqueous humor diffusion member 1002 are configured to support or permit tissue ingrowth and attachment, while the constriction diffusion membranes forming the interior region of the aqueous humor diffusion member 1002 are configured to minimize, resist, or prevent tissue ingrowth and attachment beyond or interior to a boundary or interface between the proliferation and constriction diffusion membranes.

By minimizing, resisting, or preventing tissue ingrowth and attachment beyond or interior to the constriction diffusion membranes, the glaucoma drainage system 1000 minimizes, resists, or prevents tissue ingrowth into the reservoir 1010, which helps maintain performance of the glaucoma drainage system 1000 during and after biointegration thereof. For example, it is to be appreciated that minimizing, resisting, or preventing tissue ingrowth into the constriction diffusion membranes, and thus the reservoir 1010 operates to maintain a flexibility of the glaucoma drainage system 1000, which as discussed herein helps minimize relative movement between the glaucoma drainage system 1000 and the surrounding tissue and thus helps minimize irritation of the surrounding tissue. In particular, minimizing, resisting, or preventing tissue ingrowth into the constriction diffusion membranes helps avoid tissue from proliferating across the interface between adjacent constriction diffusion membranes an thus helps avoid such tissue ingrowth from interlocking the constriction diffusion membranes together. Avoiding the interlocking the constriction diffusion membranes helps maintain the ability of the constriction diffusion membranes to slide and move relative to one another, which helps maintain flexibility of the glaucoma drainage system 1000.

In some examples, as discussed further below, the aqueous humor diffusion membrane 1002 is configured such that the interface surfaces of adjacently situated diffusion membranes face one another. In some examples, the first and second proliferation diffusion membranes 1100 and 1400 and the first and second constriction diffusion membranes 1200 and 1300 are oriented such that their peripheries align with and/or are coaxial with one another. In some embodiments, one or more of the peripheries of the diffusion members forming the body of the aqueous humor diffusion member 1002 form the periphery 1008 of the aqueous humor diffusion member 1002. For example, as shown in FIGS. 2A and 2B, the peripheries 1106, 1206, 1306, and 1406, collectively, form or define the periphery 1008 of the aqueous humor diffusion member 1002. It is to be appreciated, however, that the periphery of the aqueous humor diffusion member 1002 may be formed from less than all of the peripheries of the diffusion membranes forming the body of the aqueous humor diffusion member 1002. For instance, in some examples, the periphery 1008 of the aqueous humor diffusion member 1002 may be formed or defined by the peripheries 1106 and 1406 of the first and second proliferation diffusion membranes 1100 and 1400.

As mentioned above, in various embodiments, adjacently situated diffusion membranes are generally oriented such that one or more of their interface surfaces is situated adjacent to or otherwise faces an interface surface of an adjacently situated diffusion membrane. That is, in various embodiments, the interface surfaces of adjacently situated diffusion membranes face each other. In the embodiment depicted in FIGS. 2A, 2B, and 3, the first proliferation diffusion membrane 1100 and the first constriction diffusion membrane 1200 are adjacently situated such that the second interface surface 1104 of first proliferation diffusion membrane 1100 faces the first interface surface 1202 of first constriction diffusion membrane 1200. Similarly, as shown in FIGS. 2A, 2B, and 3, first constriction diffusion membrane 1200 and second constriction diffusion membrane 1300 are adjacently situated such that the second interface surface 1204 of first constriction diffusion membrane 1200 faces the first interface surface 1302 of second constriction diffusion membrane 1300. Similarly, as shown in FIGS. 2A, 2B, and 3, second constriction diffusion membrane 1300 and second proliferation diffusion membrane 1400 are adjacently situated such that the second interface surface 1304 of second constriction diffusion membrane 1300 faces the first interface surface 1402 of second proliferation diffusion membrane 1400.

Thus, in some embodiments, stacked configurations like those described above provide for a first diffusion membrane having first and second interface surfaces and a second diffusion membrane having first and second interface surfaces where the first and second diffusion membranes are adjacently situated such that the second interface surface of the first diffusion membrane faces the first interface surface of the second diffusion membrane.

In various embodiments, the first and second proliferation diffusion membranes 1100 and 1400 and the first and second constriction diffusion membranes 1200 and 1300 may include or be formed of one or more layers or sheets of expanded polytetrafluoroethylene (ePTFE), or other polymers, such as, but not limited, to polyurethane, polysulfone, polyvinylidene fluoride or polyvinylidene difluoride (PVDF), polyhexafluoropropylene (PHFP), perfluoroalkoxy polymer (PFA), polyolefin, fluorinated ethylene propylene (FEP), acrylic copolymers and other suitable fluoro-copolymers. These polymers can be in sheet, knitted or woven (including individual or multi-fiber strands), or non-woven porous forms. In some examples, one or more of the first and second proliferation diffusion membranes 1100 and 1400 and/or the first and second constriction diffusion membranes 1200 and 1300 may be formed from a plurality of layers or sheets of polymer material. In some such examples, the layers or sheets of polymer material may be laminated or otherwise mechanically coupled together, such as by way of heat treatment and/or high pressure compression and/or adhesives and/or other lamination methods known by those of skill in the art. In some embodiments, as explained in greater detail below, the layers of polymer material may be coupled together at discrete locations to form stabilizing structures that extend through the resulting proliferation and/or constriction diffusion membranes. Similarly, in some embodiments, as explained in greater detail below, proliferation and/or constriction diffusion membranes may be coupled together at discrete locations to form stabilizing structures that extend through the resulting aqueous humor diffusion member 1002. It is to be appreciated that such stabilizing structures are operable to constrain a shape or profile of the aqueous humor diffusion member 1002 upon inflation or dilation of the reservoir 1010, as mentioned above.

In some embodiments, the layers or sheets of polymer material forming the first and/or second proliferation diffusion membranes 1100 and 1400 and/or the first and/or second constriction diffusion membranes 1200 and 1300 may be subjected to one or more processes prior to or after their formation to modify their microstructure (and thus their material properties) to increase or decrease a natural permeability (e.g., a permeability to aqueous humor) of the polymeric material(s). In some examples, such processes include, but are not limited to, material coating processes, surface preconditioning processes, and/or perforation processes. Material coating processes may be utilized to at least partially fill the porous space of the polymeric material(s), to thereby reduce permeability, as those of skill will appreciate. Additionally or alternatively, material coating processes may be utilized to apply one or more drug or antimicrobial coatings to the surface of the polymer material (such as metallic salts, including silver carbonate), and organic compounds (e.g. chlorhexidine diacetate), to the polymer material.

In some embodiments, one or both of the first and second proliferation diffusion membranes 1100 and 1400 and/or one or both of the first and second constriction diffusion membranes 1200 and 1300 may be hydrophilic. In some embodiments, one or both of the first and second proliferation diffusion membranes 1100 and 1400 and/or one or both of the first and second constriction diffusion membranes 1200 and 1300 is hydrophobic. Thus, in some examples, the aqueous humor diffusion member 1002 may include one or more hydrophilic membranes, and one or more hydrophobic membranes.

Accordingly, hydrophilic coatings to enable wet out of the polymer matrix may also be applied as if the polymer surfaces are hydrophobic in nature. Surface coatings comprising antioxidant components can be applied to mitigate the body's inflammatory response that naturally occurs during wound healing after surgery. Surfaces can be modified with anti-proliferative compounds (e.g. Mitomycin C, 5-fluoracil), to moderate the surrounding tissue response in the eye. In some examples, one or more surface preconditioning processes may additionally or alternatively be utilized to form layers exhibiting a preferred microstructure (e.g., wrinkles, folds, or other geometric out-of-plane structures), as explained in U.S. Pat. No. 9,849,629 to Zagl, et al. Such surface preconditioning could facilitate a bolder early inflammatory phase after surgery, providing an early stable interface between porous device and tissue. In some examples, a heparin coating (e.g., thromboresistant) may additionally or alternatively be applied to help minimize or reduce cell formation including fibrinogen buildup following a surgical implantation procedure.

In some embodiments, one or more perforation processes may additionally or alternatively be utilized to form a plurality of perforations or small holes in the polymeric material(s) in addition to any perforations or small holes naturally occurring in the polymeric material(s), which operates to increase a natural permeability (e.g., a permeability to aqueous humor) of the polymeric material(s). Such perforation processes may increase a number of perforations or small holes present in the polymeric material(s) and/or may increase an average size of the perforations or small holes present in the polymeric material(s), and may be performed before and/or after the formation of the proliferation and/or constriction diffusion membranes. In some embodiments, the permeability of the first and/or second proliferation diffusion membranes 1100 and 1400 and/or the first and second constriction diffusion membranes 1200 and 1300 may be altered to tune or otherwise modify flux and/or flow resistance of aqueous humor to a desired amount.

In various embodiments, the first and/or second proliferation diffusion membranes 1100 and 1400 may include perforations or small holes that range in size (or average size) from between twenty (20) microns and one-hundred (100) microns. In other examples, the size (or average size) of the perforations or small holes in the first and/or second proliferation diffusion membranes 1100 and 1400 may exceed one-hundred-fifty (150) microns. In various embodiments, the first and/or second proliferation diffusion membranes 1100 and 1400 may include perforations or small holes less than twenty (20) microns, but larger than one (1) or two (2) microns, as perforations or small holes less than one (1) or two (2) microns generally inhibit, resist, or otherwise prevent ingrowth of vessels and other tissues.

Accordingly, in various embodiments, the first and second constriction diffusion membranes 1200 and 1300 are configured or selected such that the perforations or small holes therein are generally sized at less than (or have an average size of less than) one (1) micron or two (2) microns to minimize, resist, or prevent the ingrowth and attachment of tissue, while maintaining aqueous humor permeability.

It is to be appreciated that the first and second proliferation diffusion membranes 1100 and 1400 may be configured to have the same or different permeabilities. Similarly, it is to be appreciated that the first and second constriction diffusion membranes 1200 and 1300 may be configured to have the same or different permeabilities. In some examples, the various proliferation and constriction diffusion membranes discussed herein may possess the same inherent permeabilities, but undergo one or more of the material modification processes discussed herein to achieve different relative permeabilities. In some embodiments, one or more of the material modification processes discussed herein operates to change or otherwise modify the naturally occurring permeability of the polymeric material(s). Thus, in some embodiments, the permeabilities of the proliferation and/or constriction diffusion membranes may be based on the naturally occurring microstructure of the polymeric material(s) and/or one or more of the material modification processes discussed herein. Those of skill in the art will appreciate that a permeability is generally related to the resistance of a fluid transporting through the pore space of porous media, and that materials associated with low permeabilities exhibit greater resistance to flow than do those materials with higher permeability.

In some embodiments, the perforations or small holes in the proliferation and constriction diffusion membranes may be formed through one or more salt inclusion processes, or through the use of one or more drilling, die-punching, needle-puncturing, or laser cutting processes, which may be performed before and/or after the formation of the proliferation and/or constriction diffusion membranes.

Generally, the processes described above may be utilized to form proliferation diffusion membranes having a microstructure that permits the ingrowth of surrounding vessels and other tissues and that is permeable to aqueous humor. Similarly, the processes described above may be utilized to form constriction diffusion membranes having a microstructure that minimizes, resists, or otherwise prevents the ingrowth of surrounding vessels and other tissues, but that is permeable to aqueous humor. The aqueous humor that percolates and/or diffuses across the constriction and proliferation diffusion membranes may be absorbed by the vessels that have grown into the proliferation diffusion membranes and/or the vessels exterior to the aqueous humor diffusion member 1002, and/or may percolate through the surrounding tissues and into the tear film.

As mentioned above, in some embodiments, the differential pressure observed between the reservoir 1010 of the glaucoma drainage system 1000 and the environment exterior to the glaucoma drainage system 1000 (e.g., atmospheric pressure) is a mechanism that facilitates the flow of aqueous humor through the aqueous humor diffusion member 1002 of the glaucoma drainage system 1000. In some embodiments, the mechanism of reabsorption and the carrying away of the evacuated aqueous humor by the vessels grown into and surrounding the glaucoma drainage system 1000 helps facilitate the evacuation of aqueous humor from the anterior chamber.

However, it is to be appreciated that in addition to facilitating the reabsorption and carrying away of evacuated aqueous humor, the ingrowth of tissues, vessels, and cells into the proliferation diffusion membrane(s) of the aqueous humor diffusion member 1002 also helps prevent, reduce, minimize, or limit the onset of foreign body tissue responses. Specifically, as mentioned above tissue ingrowth and attachment helps minimize relative movement between the glaucoma drainage system 1000 and the tissue of the eye. By helping minimize such relative movement, the glaucoma drainage system 1000 helps avoid irritation of the eye tissue that can occur and that can lead to foreign body tissue response, which can lead to excessive scar formation and/or erosion and site infection of the glaucoma drainage system 1000.

In some embodiments, one or more of the adjacently situated diffusion membranes forming the body of the aqueous humor diffusion member 1002 are connected or otherwise coupled to together. In some embodiments, adjacently situated diffusion membranes are coupled at one or more discrete portions or regions along their adjacently facing interface surfaces. In some embodiments, adjacently situated diffusion membranes may be coupled along at least a portion of an adjoining edge (or edges). In other embodiments, adjacently situated diffusion membranes may be additionally or alternatively coupled at one or more discrete location along the adjoining surfaces interior to the edge (or edges). In yet other embodiments, adjacently situated diffusion membranes may be coupled along an entirety of their adjacently facing interface surfaces (e.g., applying an adhesive across an entirety of a surface area of adjacently facing interface surfaces). Thus, in some embodiments, one or more of the adjacently situated diffusion membranes may be coupled at less than all of their adjacently facing interface surfaces (e.g., at discrete locations or a portion thereof) or they may be coupled along an entirety of the facing interface surfaces.

In those embodiments where adjacently situated diffusion membranes are coupled along a portion of less than all of their adjacently facing interface surfaces, one or more discrete locations along adjacently facing interface surfaces are connected or otherwise coupled together while one or more other discrete locations along adjacently facing interface surfaces are not coupled together. That is, in some embodiments, at least one region or area of adjacently facing interface surfaces remains intentionally unadhered, unbonded, or otherwise uncoupled.

In some such embodiments, these uncoupled regions or areas may include regions or areas central to a peripheral edge. Generally, these uncoupled regions or areas are free to move or slide relative to one another, and may separate from one another to serve as a reservoir for the accumulation of evacuated aqueous humor. In various examples, providing such a degree of freedom (e.g., in shear) provides for considerable flexibility because diffusion membranes can move relative to one another to conform to changes in curvature as the aqueous humor diffusion member 1002 is bent and moves, such as with natural movement of the eye. Thus, the discontinuity of coupling of the diffusion membranes provides for a glaucoma drainage system 1000 exhibiting better eye conformity and that is better suited to dynamically respond to changes in curvature of the eye 2000 as the patient blinks, focuses, and moves the eye within the eye socket. Unlike the more rigid conventional designs, the increased flexibility also minimizes movement of the glaucoma drainage system 1000 relative to the surrounding tissue.

Figure 4A:
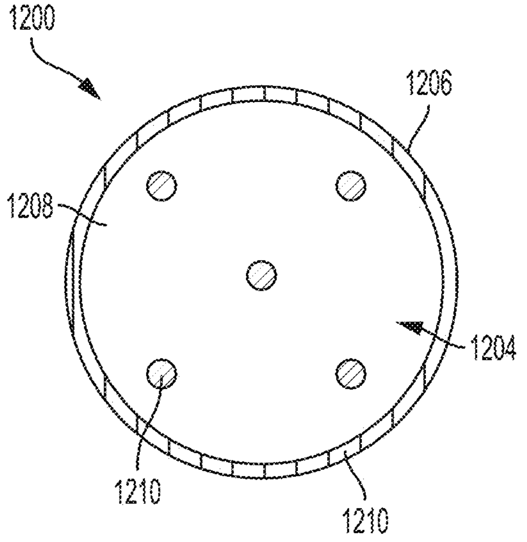
FIGS. 4A-4D are illustrations of constriction diffusion membrane interface surfaces consistent with various aspects of the present disclosure.

Turning now to FIGS. 4A to 4D, examples of interface surfaces including coupled and uncoupled (e.g., bonded and unbonded) regions are illustrated. FIG. 4A is a cross sectional view of second interface surface 1204 taken along the boundary (4-4, FIG. 2) situated between adjacently facing first and second interface surfaces 1204 and 1302, and with fluid conduit 1500 removed for clarity. As mentioned above, in some embodiments, adjacently facing interface surfaces may be coupled together at a plurality of discrete locations such that adjacently facing interface surfaces include coupled regions and uncoupled regions. FIG. 4A shows second interface surface 1204 of first constriction diffusion membrane 1200, which includes coupled regions 1210 (illustrated as cross-hatched regions) where the second interface surface 1204 is coupled to adjacently facing first interface surface 1302 of second constriction diffusion membrane 1300 in addition to a coupling along the peripheral edge 1206. As shown in FIG. 4A, second interface surface 1204 of first constriction diffusion membrane 1200 also includes uncoupled regions 1208 (illustrated as regions between and around the cross-hatched regions) where the second interface surface 1204 is situated adjacent to but otherwise uncoupled from adjacently facing first interface surface 1302 of second constriction diffusion membrane 1300. In this illustrated example of FIG. 4A, adjacently facing first and second interface surfaces 1204 and 1302 are free to slide and move relative to one another along uncoupled regions 1208. Moreover, these uncoupled regions 1208 are free to separate from one another to form the reservoir 1010 for the accumulation of aqueous humor.

It will be appreciated that while the uncoupled regions 1208 between the first and second constriction diffusion membranes 1200 and 1300 shown in FIGS. 4A to 4D are free to separate from one another to form the reservoir 1010, the coupled regions 1210 are configured to remain coupled. In various examples, these coupled regions 1210 operate to control the profile of the glaucoma drainages system 1000 as the reservoir 1010 inflates or dilates.

Figure 4B:
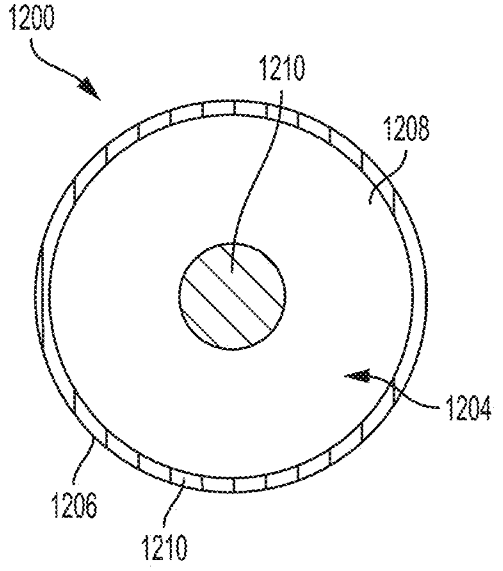

FIG. 4B is a cross sectional view of second interface surface 1204 taken along the boundary (4-4, FIG. 2) situated between adjacently facing first and second interface surfaces 1204 and 1302. FIG. 4B illustrates another configuration where second interface surface 1204 includes a centrally positioned coupled region 1210 (illustrated as cross-hatched regions) and where second interface surface 1204 is coupled to adjacently facing first interface surface 1302 of second constriction diffusion membrane 1300 in addition to being coupled along the peripheral edge 1206. Though not illustrated, it is to be appreciated that the coupling configurations of FIGS. 4B and 4A may be combinable in-whole or in-part.

Figure 4C:
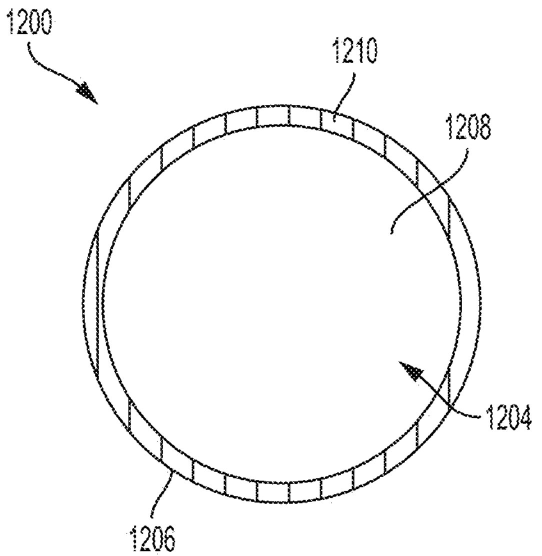

FIG. 4C illustrates another configuration where second interface surface 1204 includes a peripherally positioned coupled region 1210 (illustrated as a cross-hatched region) while second interface surface 1204 is coupled to adjacently facing first interface surface 1302 of second constriction diffusion membrane 1300. Though not illustrated, it should be appreciated that the coupling configurations of FIGS. 4C, 4B, and/or 4A may be combinable in-whole or in-part.

Figure 4D:
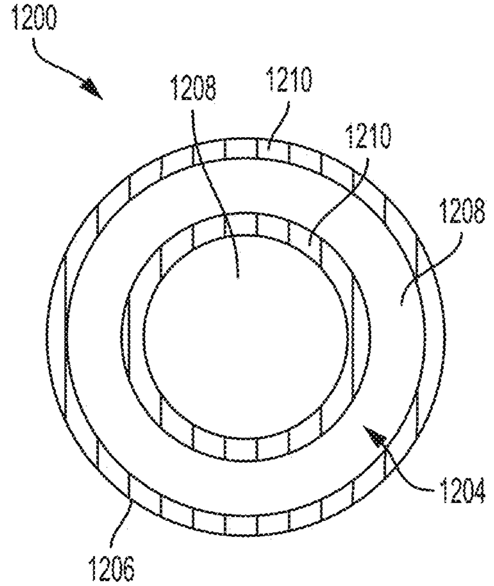

FIG. 4D illustrates another alternative configuration where second interface surface 1204 includes a peripherally positioned coupled region 1210 and a concentric annular inner coupled region 1210 (both illustrated as cross-hatched regions) and where second interface surface 1204 is coupled to adjacently facing first interface surface 1302 of second constriction diffusion membrane 1300. The configuration shown in FIG. 4D is one that includes a possibility of two distinct reservoirs for the accumulation of aqueous humor. The first reservoir corresponds to the uncoupled portion 1208 radially inwardly of the concentric annular inner coupled region 1210 radially inwardly of the peripherally positioned coupled region 1210 about the periphery 1206. The second reservoir corresponds to the uncoupled portion 1208 situated between the concentric annular inner coupled region 1210 and the peripherally positioned coupled region 1210. It is to be appreciated that a first fluid conduit may be fluidly coupled with the first reservoir while a second fluid conduit is coupled with the second reservoir of the configuration shown in FIG. 4D. Alternatively, a single fluid conduit may be fluidly coupled with both of the first and second reservoirs shown in FIG. 4D, such as by way of corresponding apertures in the fluid conduit. In another alternative example, a portion of less than all of the concentric annular inner coupled region 1210 may alternatively be uncoupled such that the first and second reservoir are fluidly coupled. While not illustrated, it should be appreciated that the coupling configurations of FIGS. 4D, 4C, 4B, and/or 4A may be combinable in-whole or in-part.

It should also be appreciated that while FIGS. 4A-4D illustrate exemplary coupled and uncoupled (e.g., bonded and unbonded) regions of second interface surface 1204, adjacently facing first interface surface 1302 includes coupled and uncoupled regions corresponding to those coupled and uncoupled regions, respectively, of second interface surface 1204. Additionally, it should be appreciated that the illustrated embodiments of FIGS. 4A-4D should not be interpreted as limiting the disclosure to the illustrated embodiments. Instead, those of skill in the art will appreciate that virtually any pattern of coupled and uncoupled regions may be utilized without departing from the spirit or scope of the disclosure.

Though the boundary between first proliferation diffusion membrane 1100 and first constriction diffusion membrane 1200 is not illustrated, it should be appreciated that adjacently facing first and second interface surfaces 1202 and 1104 may be uniformly coupled across the entire boundary or alternatively coupled according to the above-discussed embodiments. Likewise, though the boundary between second proliferation diffusion membrane 1400 and second constriction diffusion membrane 1300 is not illustrated, it should be appreciated that adjacently facing first and second interface surfaces 1402 and 1304 may be uniformly coupled across the entire boundary or alternatively coupled according to the above-discussed embodiments.

As previously discussed, adjacent diffusion membranes may be connected or coupled to one another by way of one or more heat treatment processes and/or one or more bonding agents such as one or more adhesives. In some embodiments, adjacently situated diffusion membranes and/or the layers of material forming a diffusion membrane, are partially or completely bonded via thermal methods when each of the materials are brought to or above their melting temperatures. In some embodiments, such thermal processes facilitate adhesive or cohesive bond formation between the polymer materials or layers of polymeric material. In some embodiments, adjacently situated diffusion membranes forming a diffusion membrane, are partially or completely bonded via thermal methods when at least one of the materials is brought to or above its melting temperature. In some embodiments, such thermal processes facilitate adhesive or cohesive bond formation between the materials or layers of material. In some embodiments, one or more suitable adhesives are utilized and provide a sufficiently bonded interface, which can be continuous or discontinuous.

As discussed above, in various embodiments, the glaucoma drainage system 1000 is operable or otherwise configured to evacuate aqueous humor from the anterior chamber (AC) of the eye. In some embodiments, the glaucoma drainage system 1000 includes a fluid conduit 1500, as shown in at least FIG. 1. In various embodiments, fluid conduit 1500 is a compliant tubular structure (e.g., a catheter) that extends into an interior of the aqueous humor diffusion member 1002 and fluidly couples the aqueous humor diffusion member 1002 and the anterior chamber of the eye. The fluid conduit 1500 provides fluid egress from the anterior chamber. As shown in FIG. 3, the fluid conduit 1500 includes a first end 1502 and a second end 1504, and lumen extending from the first end 1502 to the second end 1504. Generally, the fluid conduit 1500 may be formed from silicone, ePTFE, polycarbonate, polyethylene, polyurethane, polysulfone, PVDF, PHFP, PFA, polyolefin, FEP, acrylic copolymers and other suitable fluoro-copolymers, alone or in combination or any other biocompatible polymer suitable for forming a compliant fluid conduit 1500.

In some embodiments, the fluid conduit 1500 is formed via a tubular melt extrusion process. In some embodiments, an extruded fluid conduit 1500 may be drawn down to a final target dimension. In some embodiments, the fluid conduit 1500 is formed via a tube paste-extrusion and expansion process commensurate with producing a desired wall thickness, porosity, stiffness, and/or dimension. In some embodiments, the fluid conduit 1500 is formed via one or more tape wrapping processes where a tape is wrapped around a mandrel of a designated dimension and cross-section. In some embodiments, the wound tape may further be bonded to itself via one or more thermal or adhesive methods before or after removal from the mandrel. In various embodiments, a wrapped tape configuration (e.g., ePTFE or other suitable material as discussed herein) provides for a fluid conduit 1500 construction having different layers with differing porosities. For example, an inner wound layer may be more porous than an outer wound layer. In some embodiments, the fluid conduit 1500 is formed via successive dip-coating of a material onto a properly-sized mandrel followed by solvent removal and mandrel extraction from the formed fluid conduit 1500.

In some embodiments, a diameter of lumen of the fluid conduit 1500 is one that is sufficient to allow flow of aqueous humor through the fluid conduit 1500 from the anterior chamber to the aqueous humor diffusion member 1002, but that does not result in a fluid conduit 1500 having an exterior diameter that significantly interferes with or impairs normal eye functions (e.g., does not interfere with blinking or regular eye movement).

As mentioned above, the fluid conduit 1500 fluidly couples the aqueous humor diffusion member 1002 to the anterior chamber of the eye such that aqueous humor can be evacuated from the anterior chamber and delivered to the aqueous humor diffusion member 1002, and in particular to the reservoir defined within the interior region of the aqueous humor diffusion member 1002. Accordingly, the fluid conduit 1500 is configured to extend between the anterior chamber of the eye and the position on the eye at which the aqueous humor diffusion member 1002 is mounted or otherwise integrated. In some embodiments, a length of the fluid conduit 1500 may be between one (1) millimeter and thirty (30) millimeters, though generally the fluid conduit 1500 length is oversized (or otherwise longer than necessary) such that a physician may trim its length to a specific length required for the unique anatomy of the patient. However, in various embodiments, the length and diameter of the lumen of the fluid conduit 1500 are preselected to control pressure drop across the length to minimize the risk of hypotony (e.g. dangerously low eye pressure), as the pressure drop across the fluid conduit 1500 is a function of the length of the fluid conduit 1500. In some embodiments, the fluid conduit 1500 may be premarked with cutoff length identifiers that correspond to theoretically expected pressure drops when implanted. Such a configuration provides the physician with an option for specifically tailoring the pressure drop to the patient's particular needs. In such embodiments, after trimming the fluid conduit 1500 to the length corresponding to the desired pressure drop, the physician may optionally advance the first end 1502 of the fluid conduit 1500 further into the anterior chamber or alternatively position the aqueous humor diffusion member 1002 further from the point of penetration of the fluid conduit 1500 into the anterior chamber (e.g., further around the eye) to accommodate a desired length.

In various embodiments, the fluid conduit 1500 may be porous or non-porous, or may include a combination of porous portions and non-porous portions. For instance, in some embodiments, the fluid conduit 1500 may have a length defined by a first portion (or region) and a second portion (or region). In some embodiments, the first portion may be a non-porous portion while the second portion is a porous portion. In some embodiments, the non-porous portion is impermeable to aqueous humor while the porous portion is permeable to aqueous humor. Thus, in some embodiments, aqueous humor evacuated from the anterior chamber by the fluid conduit 1500 may percolate through the porous portion of the fluid conduit 1500. For example, the portion of the fluid conduit 1500 in the anterior chamber may have an outer surface that is impermeable to aqueous humor or cellular penetration, while a portion of the fluid conduit 1500 outside the anterior chamber may permit or otherwise allow cellular infiltration and tissue ingrowth and biointegration. In some embodiments, an inner surface of the fluid conduit 1500 may be impermeable to aqueous humor and is configured to minimize the ingress of bacteria and the ingrowth of vessels and tissue structures.

In some embodiments, the porous portion of the fluid conduit 1500 may be formed by subjecting one region (e.g., a portion of the length of the fluid conduit 1500) to one or more of the perforation processes discussed above to form a plurality of perforations in the subjected region. However, the fluid conduit 1500 need not include a portion that is permeable to aqueous humor.

Generally, the flow of aqueous humor through the glaucoma drainage system 1000 is governed by a pressure difference between the intraocular pressure and the pressure within the aqueous humor diffusion member 1002 (e.g., which is a function of the forces acting on the aqueous humor diffusion member 1002, such as atmospheric pressure). A pressure difference between these pressure regions will cause aqueous humor to flow from the anterior chamber to the glaucoma drainage system 1000. In some embodiments, the rate at which the aqueous humor flows through the glaucoma drainage system 1000 is governed by this pressure difference and a resistance to flow. In some embodiments, the resistance to flow is a function of fluid conduit flux resistance (e.g., based on tube geometry, diameter, and length, generally based on the Hagen-Poiseuille Equation) and a flux resistance of the aqueous humor through the aqueous humor diffusion member 1002, as those of skill will appreciate. In some embodiments, as mentioned above, a flux resistance of the aqueous humor through the aqueous humor diffusion member 1002 can be controlled through a permeability of the underlying materials forming the aqueous humor diffusion member 1002.

As mentioned above, the fluid conduit 1500 is a soft and compliant biocompatible tubular structure. In some embodiments, the fluid conduit 1500 is compliant in that it exhibits low column strength and is generally incapable of supporting its own weight. That is, in some embodiments, the fluid conduit 1500 lacks a sufficient amount of structural integrity (e.g. compressive hoop strength) necessary to avoid collapsing (e.g., a collapse of the inner lumen extending through the fluid conduit 1500) under its own weight.

In some embodiments, the intraocular pressure of the anterior chamber inflates or otherwise operates to maintain the generally tubular geometry (e.g., avoid collapse of the inner lumen 1506A) of the fluid conduit 1500. That is, in some embodiments, the aqueous humor flowing through the lumen of the fluid conduit 1500 operates to inflate the lumen. Such a configuration provides for a soft and compliant fluid conduit 1500 that conforms to the curvature of the eye and avoids interfering with normal eye function (e.g., pivoting and blinking). It is to be appreciated that, in some embodiments, the fluid conduit 1500 may alternatively be constructed such that it exhibits a sufficient amount of structural integrity to maintain its generally tubular geometry and/or avoid a collapse of the inner lumen.

Referring again to FIG. 3, in some embodiments, the fluid conduit 1500 includes a first end 1502 and an opposing second end 1504. In some embodiments (not illustrated in FIG. 3), the fluid conduit 1500 includes a lumen extending from the first end 1502 to the second end 1504. In some embodiments, the first end 1502 is insertable into the anterior chamber and the second end 1504 inserted into or otherwise attached to the aqueous humor diffusion member 1002. In some embodiments, the first end 1502 is positionable within the anterior chamber such that the first end 1502 extends into an interior region of the anterior chamber.

In some embodiments, after placing the first end 1502 of the fluid conduit 1500 into the anterior chamber, the fluid conduit 1500 may be secured to avoid dislodgement of the fluid conduit 1500 from within the anterior chamber. In some embodiments, one or more stitches are utilized to couple the fluid conduit 1500 and/or the aqueous humor diffusion member 1002 to the eye tissue. In some embodiments, a biocompatible tissue adhesive is used to bond the fluid conduit 1500 and/or the aqueous humor diffusion member 1002 to surrounding or adjacent tissue. In some embodiments, a needle track that is created through tissue prior to placement of the fluid conduit 1500 can be sized so as to provide a sufficient interface fit with the fluid conduit 1500 over the length of the needle-tract. In some embodiments, the first end 1502 of the fluid conduit 1500 can additionally or alternatively be flared to a greater diameter than other portions (e.g., a central portion) of the fluid conduit 1500 (or a lumen in the tissue through which the fluid conduit 1500 extends) to create an interference attachment that helps to maintain placement of the first end 1502 within the anterior chamber of the eye. In some examples, the flared first end 1502 of the fluid conduit 1500 helps avoid dislodgment of the fluid conduit 1500 from it position within the anterior chamber.

Figure 5:
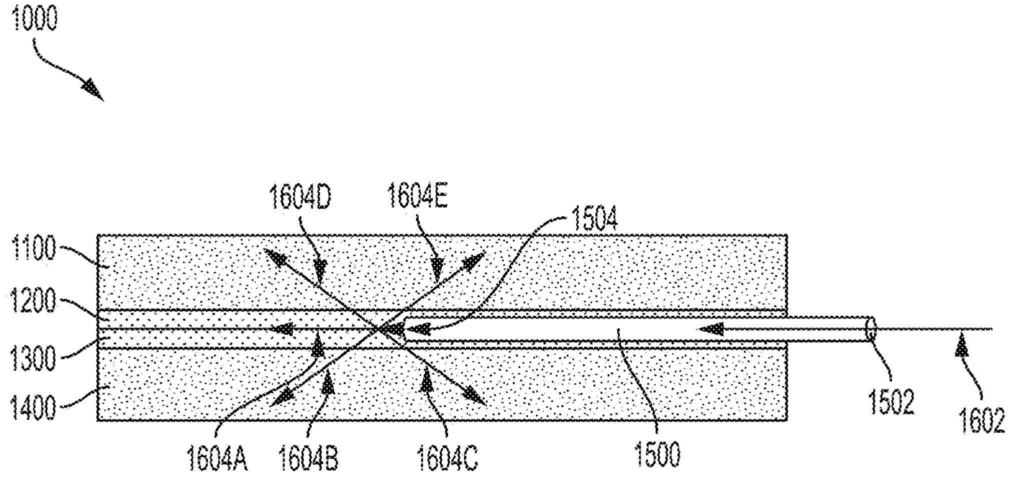
FIG. 5 is an illustration of a glaucoma drainage system consistent with various aspects of the present disclosure.

In some embodiments, the second end 1504 of the fluid conduit 1500 is coupled with the aqueous humor diffusion member 1002 such that the reservoir defined within the aqueous humor diffusion member 1002 is fluidly coupled with the fluid conduit 1500, and thus the fluid filled body cavity (e.g., the anterior chamber of the eye) when the glaucoma drainage system 1000 is implanted within the body. In some embodiments, the second end 1504 of the fluid conduit 1500 extends into or otherwise terminates within the interior of the aqueous humor diffusion member 1002, such as between the first and second constriction diffusion membranes 1200 and 1300 defining the reservoir. For example, as shown in FIG. 5, the fluid conduit 1500 is coupled to the aqueous humor diffusion member 1002 such that the fluid conduit 1500 terminates within an interior of the aqueous humor diffusion member 1002. That is, in some embodiments, the second end 1504 is coupled to the aqueous humor diffusion member 1002 such that evacuated aqueous humor exiting the fluid conduit 1500 at the second end 1504 diffuses or is otherwise injected into the aqueous humor diffusion member 1002 beginning at some position interior to its periphery 1008. Though not shown separated from one another in FIG. 5, it is to be appreciated that the first and second constriction diffusion membranes 1200 and 1300 are operable to separate from one another, as discussed above, such that the reservoir is inflatable or dilatable.

As shown in FIG. 5, aqueous humor traveling through the fluid conduit 1500 along arrow 1602 exits the second end 1504 of the fluid conduit 1500 and diffuses or is otherwise injected into the reservoir 1010. As mentioned above, the reservoir 1010 may include the pore space of the first and second constriction diffusion membranes 1200 and 1300 and/or a region defined between the first and second constriction diffusion membranes 1200 and 1300. As shown in FIG. 5 the aqueous humor is shown exiting the fluid conduit 1500 into the reservoir 1010, which includes at least the region defined between the first and second constriction diffusion membranes 1200 and 1300.

As the evacuated aqueous humor percolates through the constriction and diffusion membranes of the aqueous humor diffusion member 1002, the aqueous humor generally percolates toward an exterior of the aqueous humor diffusion member 1002, as shown by arrows 1604A-1604E. It should be appreciated that arrows 1604A-1604E are not intended to represent actual paths of aqueous humor, but are instead intended to represent that aqueous humor is intended to percolate away from an interior region, such as the reservoir 1010, of the aqueous humor diffusion member 1002 or at least away from the second end 1504 of the fluid conduit 1500.

Figure 6:
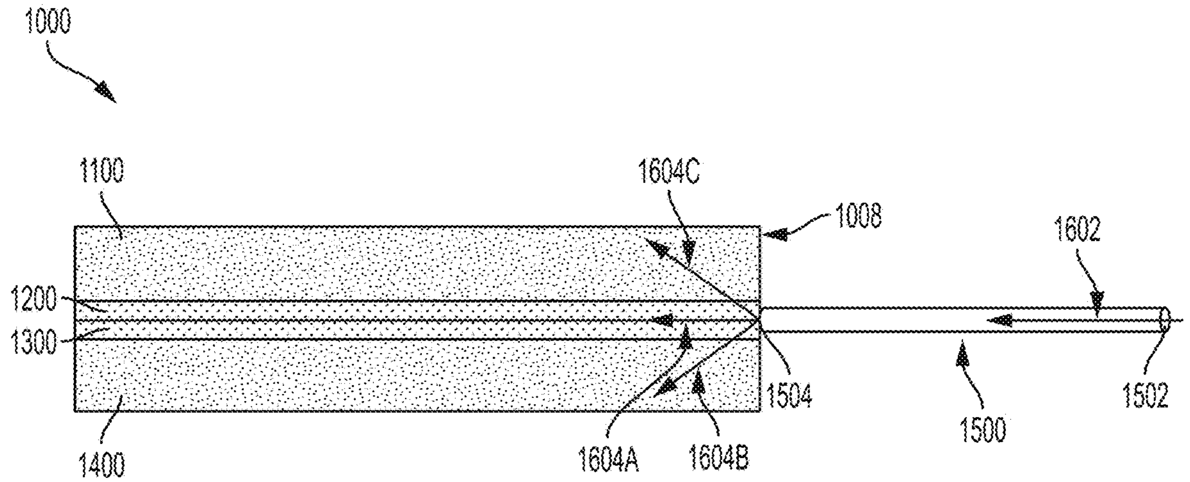
FIG. 6 is an illustration of a glaucoma drainage system consistent with various aspects of the present disclosure.

In some other embodiments, the second end 1504 of the fluid conduit 1500 is coupled to the periphery 1008 of the aqueous humor diffusion member 1002. For example, as shown in FIG. 6, the second end 1504 of the fluid conduit 1500 is coupled to the aqueous humor diffusion member 1002 at its periphery 1008. That is, in some embodiments, the second end 1504 is coupled to the aqueous humor diffusion member 1002 such that evacuated aqueous humor exiting the fluid conduit 1500 at the second end 1504 diffuses or is otherwise injected into the first and second constriction diffusion membranes 1200 and 1300 beginning at or proximate to a periphery 1008 of the aqueous humor diffusion member 1002.

In some such embodiments, as the evacuated aqueous humor percolates through the aqueous humor diffusion member 1002, the aqueous humor may percolate toward an interior of the aqueous humor diffusion member 1002 and/or may percolate toward an exterior of the aqueous humor diffusion member 1002. In some embodiments, as aqueous humor traveling through fluid conduit 1500 exits the second end 1504 of the fluid conduit 1500 between the first and second constriction diffusion membranes 1200 and 1300, as mentioned above. As similarly discussed above, the aqueous humor enters the reservoir 1010 of the aqueous humor diffusion member 1002, which may be defined between the first and second constriction diffusion membranes 1200 and 1300, or which may additionally or alternatively correspond with the pore space of the first and second constriction diffusion membranes 1200 and 1300. As mentioned above, the glaucoma drainage system 1000 is configured to allow the evacuated aqueous humor to percolate from the interior of the aqueous humor diffusion member 1002 toward an exterior of the aqueous humor diffusion member 1002.

Arrows 1604A-1604C of FIG. 6 are representative of aqueous humor generally percolating through the aqueous humor diffusion member 1002. As shown, arrow 1604A represents aqueous humor percolating through the aqueous humor diffusion member 1002 generally toward an interior region of the aqueous humor diffusion member 1002, while arrows 1604B and 1604C represent aqueous humor percolating through the aqueous humor diffusion member 1002 generally toward an exterior of the aqueous humor diffusion member 1002. As mentioned above, it should be appreciated that arrows 1604A-1604C are not intended to represent actual paths of aqueous humor, but are instead intended to represent that aqueous humor is intended to percolate at least away from the second end 1504 of the fluid conduit 1500. Moreover, though not shown separated from one another in FIG. 6, it will be appreciated that the first and second constriction diffusion membranes 1200 and 1300 are operable to separate from one another to define the reservoir 1010 therebetween.

In various embodiments, the second end 1504 of the fluid conduit 1500 may be coupled to the periphery 1008 of the aqueous humor diffusion member 1002 by way of an adhesive, a weld, stitching, or one or more mechanical fastening mechanisms. In some embodiments, the second end 1504 of the fluid conduit 1500 may be coupled to the periphery 1008 via one or more of the above-discussed thermal bonding methods to create an adhesive or cohesive bond between the material or the layers of material.

In various embodiments, the fluid conduit 1500 is coupled to the aqueous humor diffusion member 1002 such that evacuated aqueous humor exiting the fluid conduit 1500 at the second end 1504 diffuses into a constriction diffusion membrane prior to diffusing into a proliferation diffusion membrane. For example, as illustrated in FIGS. 5 and 6, the second end 1504 of the fluid conduit 1500 is coupled to the aqueous humor diffusion member 1002 such that evacuated aqueous humor exiting the fluid conduit 1500 at the second end 1504 diffuses into one or more of first and second constriction diffusion membranes 1200 and 1300 prior to diffusing into first and second proliferation diffusion membranes 1100 and 1400.

Unlike conventional designs, the glaucoma drainage system 1000 is soft and compliant, and does not require the preservation of a hollow aqueous humor reservoir internal to its aqueous humor diffusion member 1002. Conventional permeable hollow aqueous humor reservoirs must therefore be sufficiently rigid to preserve their volumes. Accordingly, in comparison to the glaucoma drainage system 1000, conventional designs are relatively rigid and susceptible to causing relative movement between the tissue and the device and thus tissue irritation which may lead to excessive scar formation and erosion of conventional devices.

As discussed above, in various embodiments, the aqueous humor diffusion member 1002 includes one or more adjacently situated diffusion membranes having adjacently facing interface surfaces that can slide or otherwise move relative to one another. In some embodiments, aqueous humor evacuated from the anterior chamber and introduced to the aqueous humor diffusion member 1002 operates as a lubricant that reduces friction between such interface surfaces and further facilitates sliding or relative movement between the uncoupled portions or regions. Specifically, as aqueous humor enters the aqueous humor diffusion member 1002, the aqueous humor percolates and diffuses across the various diffusion membranes. As the aqueous humor percolates and diffuses across the diffusion membranes, some aqueous humor diffuses across the boundaries separating adjacently situated diffusion membranes. In some embodiments, as the aqueous humor diffuses across the boundaries, it operates as a lubricant that reduces friction between the interface surfaces of the boundary which further adds to flexibility of the aqueous humor diffusion member 1002.

As discussed above, in some embodiments, the fluid conduit 1500 is soft and compliant and generally lacks a sufficient amount of structural integrity (e.g., hoop strength) to avoid collapsing under its own weight. In some embodiments, this lack of structural integrity results in a deformation of the fluid conduit 1500 to the extent that the lumen extending therethrough loses a significant portion of its cross-sectional area. In some embodiments, this lack of structural integrity results in a deformation of the fluid conduit 1500 to the extent that the aqueous humor in the anterior chamber is significantly restricted from even entering the lumen of the fluid conduit 1500. In some embodiments, to avoid these potential risks, the fluid conduit 1500 may be configured such one or more of its ends are sufficiently structurally sound in that they can be operable to maintain lumen integrity and avoid collapse or otherwise significant deformation of the lumen. In such embodiments, an intermediate portion of the fluid conduit 1500 situated between the first and/or second ends 1502 and 1504 is generally not structurally sound in that it cannot support its own weight. For example, the end (or an end portion) of the fluid conduit 1500 that is positioned within the anterior chamber is configured such that it is operable to maintain lumen integrity and avoid collapse or otherwise significant deformation of the lumen. In this example, the above discussed risks associated with relative movement and tissue irritation due to rigidity are generally avoided because the structurally sound end of the fluid conduit 1500 is suspended within the aqueous humor of the anterior chamber and thus does not interact with tissue in a manner that could lead to tissue irritation.

In various embodiments, the fluid conduit 1500 material may be subjected to one or more material conditioning processes to achieve structurally sound first and/or second ends. In some embodiments, one or more structural members, such as one or more stents or struts or reinforcing rings may be incorporated, integrated, or otherwise coupled to the first and/or second ends 1502 and 1504 to achieve the above-discussed structural integrity. These stents, struts, and/or reinforcing rings may be formed of any suitable biocompatible metallic or polymeric material discussed herein (e.g., FEP). In some embodiments, a localized densification to the first and/or second ends 1502 and 1504 of the fluid conduit 1500 can increase a structural integrity thereof to an extent sufficient to resist closure forces exerted on the ends by the body tissue.

It should be appreciated that while the aqueous humor diffusion members illustrated and described herein are generally thin, flat, and circular (or ovular), the aqueous humor diffusion member may be of any suitable shape without departing from the spirit or scope of the disclosure. For instance, the aqueous humor diffusion member may be square, rectangular, trapezoidal, or some other polygonal shape, and may include chamfered or rounded edges between sides, and the sides may be linear or generally curved in nature. Alternatively, the aqueous humor diffusion member may have a generally continuous curved edge in that it is circular or ovular, or of another suitable shape (e.g., bean-shaped). Accordingly, the embodiments, and illustrations included herein should not be interpreted as limiting and those of skill in the art will appreciate that the aqueous humor diffusion member may be of any desired shape provided that the aqueous humor diffusion member is operable to accommodate a sufficient degree of evacuated aqueous humor and to help facilitate the reabsorption of aqueous humor to constitute an effective treatment for the patient.

As mentioned above, glaucoma is a condition that occurs as a result of increased intraocular pressure. In some cases, although the intraocular pressure is generally lowered after surgical implantation of an aqueous humor drainage system, the intraocular pressure may stabilize only temporarily. For instance, natural aqueous humor reabsorption may continue to decrease and/or aqueous humor generation may increase, each of which could lead to a subsequent increase in intraocular pressure. Therefore, it may be necessary to increase the aqueous humor transmission rate through the implanted glaucoma drainage system after the implantation procedure has been completed (e.g., post-operatively). Similarly, in some cases, the anatomy may produce less aqueous humor over time. Accordingly, there exist instances where an implanted device initially configured to evacuate aqueous humor at a first rate must be calibrated to evacuate aqueous humor at a second, slower rate to account for the decrease in aqueous humor production by the anatomy.

Additionally, while the glaucoma drainage systems discussed herein include aqueous humor diffusion members and are described as including one or more diffusion membranes that are permeable to biological fluids (e.g., aqueous humor) and configured to permit tissue ingrowth, as well as one or more diffusion membranes that are permeable to biological fluids (e.g., aqueous humor) and configured to resist tissue ingrowth, it is to be appreciated that the fluid conduits and resistive elements discussed herein may be utilized with any glaucoma drainage systems. That is, while the resistive elements disclosed herein may be configured for use with any of the various glaucoma drainage systems disclosed herein, it is to be appreciated that the fluid conduits and resistive elements disclosed herein are not limited to systems having aqueous humor diffusion members that include one or more diffusion membranes that are permeable to biological fluids (e.g., aqueous humor) and configured to permit tissue ingrowth and one or more diffusion membranes that are permeable to biological fluids (e.g., aqueous humor) and configured to resist tissue ingrowth.

According to the Hagen-Poiseuille law for laminar flowing fluids, flow resistance is inversely proportional to the 4th power of the tube radius through which the flow is traveling. Accordingly, those of skill will appreciate that the flow resistance of the fluid conduit 1500 is extremely sensitive to modifications of the effective diameter of the fluid conduit 1500. Accordingly, small changes to the effective diameter of the fluid conduit 1500 can have large effects on fluid flow. Moreover, as the pressure drop across the fluid conduit 1500 is a function of the flow rate through the fluid conduit 1500, the pressure differential is also extremely sensitive to changes in the effective diameter of the fluid conduit 1500.

On the other hand, according to the Hagen-Poiseuille law for laminar flowing fluids, flow resistance is directly proportional to the length of the tube through which the flow is traveling. Accordingly, those of skill will appreciate that the flow resistance of the fluid conduit 1500 (and thus a pressure differential across the fluid conduit 1500) is less sensitive to modifications to the effective length of the fluid conduit 1500 in contrast to modifications to the effective diameter of the fluid conduit 1500. Accordingly, in some embodiments, the fluid conduit 1500 may be additionally or alternatively configured such that an effective length of the fluid conduit 1500 can be modified to cause a resulting change in the fluid flow rate through (and thus a pressure differential across) the fluid conduit 1500.

Figure 7A:
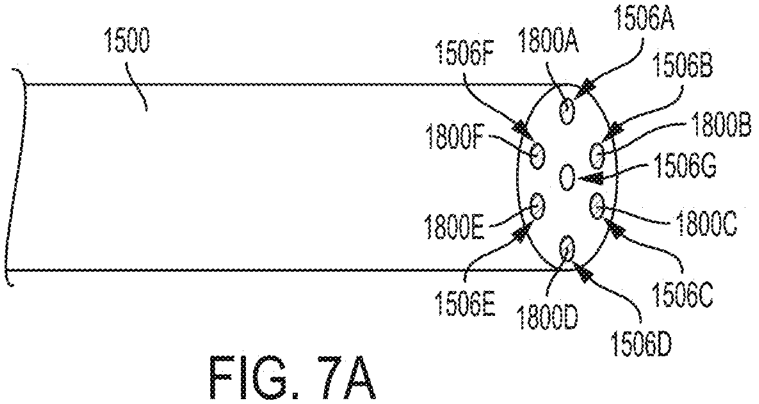
FIG. 7A is an illustration of a fluid conduit consistent with various aspects of the present disclosure.
Figure 7B:
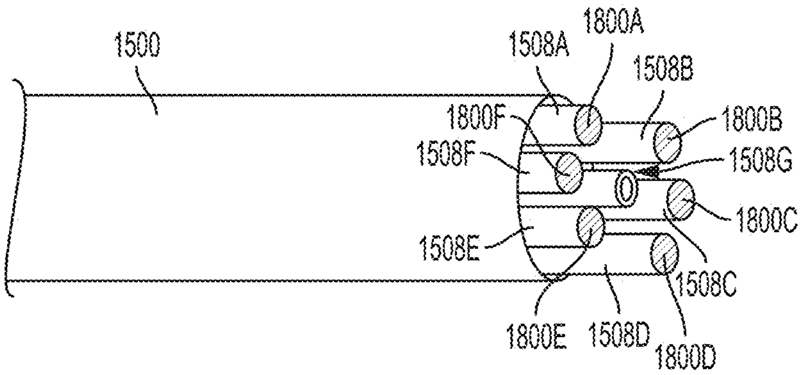
FIG. 7B is an illustration of a fluid conduit consistent with various aspects of the present disclosure.

With reference now to FIGS. 7A-7D, in various embodiments, a fluid conduit 1500 may be configured to include a plurality of lumens. The fluid conduit 1500 shown in FIG. 7A includes a singular fluid conduit construct having a plurality of lumens, while the fluid conduit 1500 shown in FIG. 7B is comprised of a plurality of individual tubular elements 1508A-1508G bound together in a bundle, where each tubular element defines a lumen. In some embodiments, an outer sheath houses the bundle. That is, in some embodiments, the bundle of tubular elements may be encased in a lumen of another fluid conduit. In some embodiments, voids between tubular elements may be filled with a filler material that is impermeable to aqueous humor so as to avoid or reduce the evacuation of aqueous humor through a channel other than a designate tubular element.

In various embodiments, one or more resistive elements (1800A-1800F, FIGS. 7A and &B) may be positioned with in one or more lumens of a fluid conduit. The resistive elements are plugs or other components that operate to obstruct the flow of fluid through the lumen within which the resistive element is positioned. In some embodiments, the resistive elements are configured to completely obstruct flow through the lumen, while in other embodiments the resistive elements are configured to partially obstruct flow through the lumen. For example, one or more of the resistive elements may be porous, as discussed further below. In various embodiments, one or more of the resistive element is configured for removal from the lumen within which it is positioned. In some embodiments, the resistive element can be removed by a physician, such as by a physician accessing the fluid conduit a physically removing the resistive element. In some embodiments, the resistive element can alternatively be removed without physical intervention, such as by way of ablation by a high energy source (e.g., a laser), or the resistive element may be configured such that it is bioabsorbable and dissolves over time. That is, in some embodiments, the resistive elements can be configured to naturally resist flow through the lumen less and less over time.

In various embodiments, removal of a resistive element operates to increase the aqueous humor transmission rate through the fluid conduit, and thus through the glaucoma drainage system. Specifically, as the resistive elements are removed, a higher volume of aqueous humor can be transferred through the fluid conduit per unit of time.

Figure 7C:
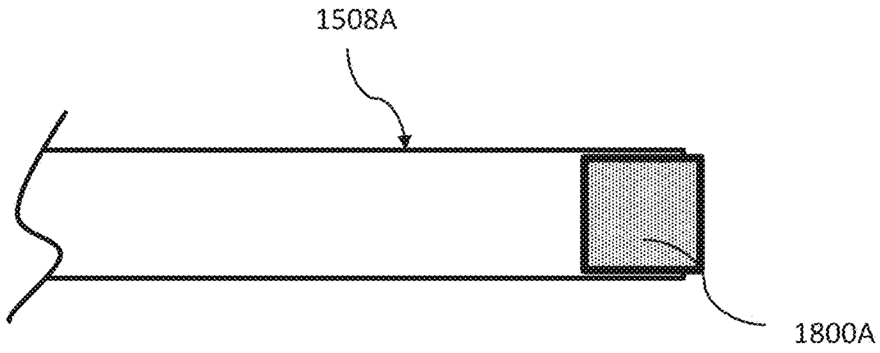
FIG. 7C is an illustration of a resistive element positioned within a fluid conduit consistent with various aspects of the present disclosure.

FIG. 7C shows a cross section of the tubular element 1508A of FIG. 7B. As shown, a resistive element 1800A is positioned within the lumen on the tubular element 1508A and is configured to obstruct a flow of fluid through the lumen of the tubular element 1508A. It is to be appreciated that while the resistive elements shown in FIGS. 7A to 7C are configured to be received within or are otherwise positionable within a lumen of the fluid conduit 1500, in some embodiments, one or more resistive elements may be disposed about or are otherwise positionable exterior to one or more of the individual tubular elements (individually or collectively) of a fluid conduit 1500.

Figure 7D:
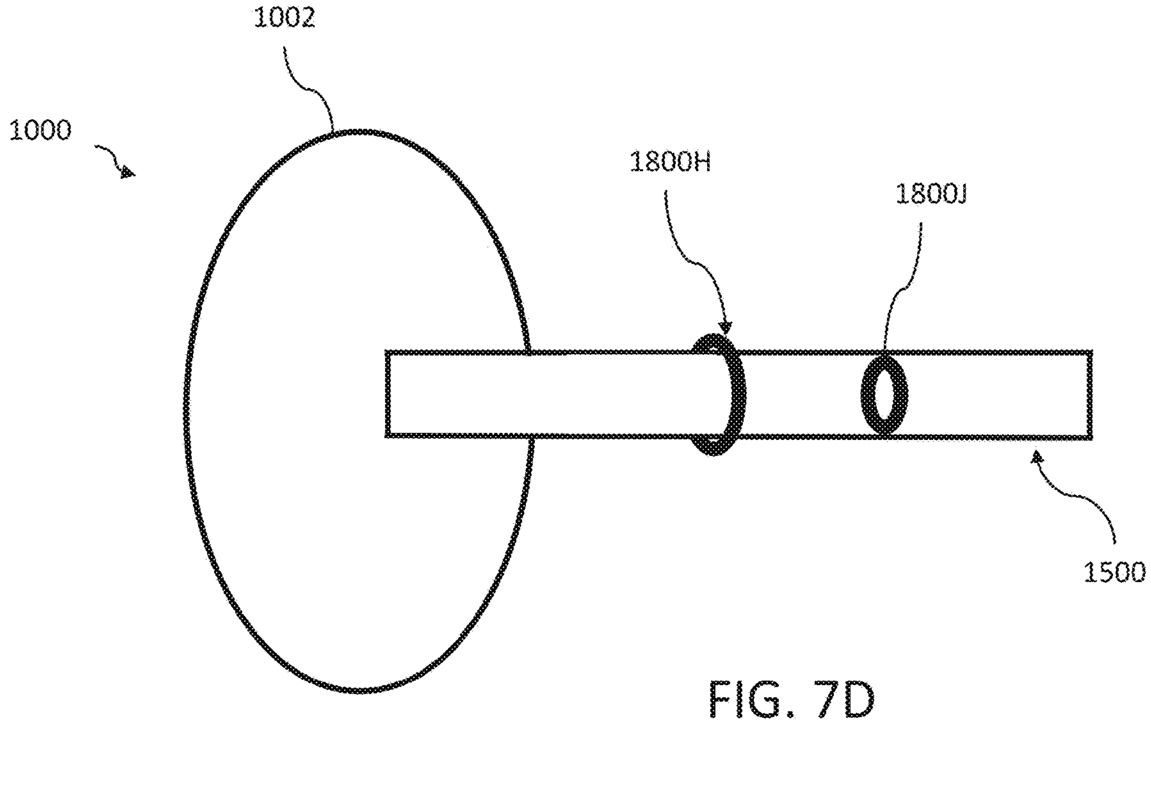
FIG. 7D is an illustration of a fluid conduit and a plurality of resistive elements consistent with various aspects of the present disclosure.

For example, as shown in FIG. 7D, resistive element 1800H is positioned exterior to the fluid conduit 1500 and is configured to obstruct a flow of fluid through the fluid conduit 1500. As shown, the resistive element 1800H may be in the form of an O-ring or a cuff. An o-ring or cuff resistive element positioned exterior to the fluid conduit is configured to radially compress the fluid conduit and thereby reduce a cross sectional diameter of one or more lumens of the fluid conduit. Such o-ring or cuff resistive elements may be positioned interior to or exterior to the lumen of the fluid conduit as shown.

Moreover, it is to be appreciated that a plurality of resistive elements may be employed to restrict fluid flow through a given lumen of a fluid conduit, as discussed further below. That is, in some embodiments, a plurality of resistive elements may be disposed about an individual tubular element and collectively operate to restrict flow through that individual tubular element. In some such embodiments, the resistive elements can be post-operatively incrementally (e.g., over the course of weeks, months or years) modified and/or removed from the tubular element. In some embodiments, such modifications may be completed via mechanical intervention by a physician via clear corneal approach, or via laser cutting, or may alternatively be configured to bioabsorb over time.

In some embodiments, one or more of the resistive elements configured to be positioned exterior to the lumen of the fluid conduit can be adhered to the fluid conduit 1500 such that the exterior resistive element remains coupled to the fluid conduit 1500 after modification. For example, an O-ring may be partially adhered (e.g., in one or more locations along the O-ring) to the fluid conduit 1500 such that upon cutting of the O-ring, the O-ring remains coupled to the fluid conduit 1500 despite not providing any subsequent resistance to flow through the fluid conduit.

With continued reference to FIGS. 7A and 7B it is to be appreciated that one or more of the lumens of the fluid conduit 1500 may be initially plugged or otherwise obstructed, such as at one or more of their ends with a material (e.g., a resistive element) that can be removed during the implantation procedure or post-operatively to fine tune the aqueous humor transmission rate of the fluid conduit. As shown in FIGS. 7A and 7B, lumens 1506A-1506F and tubular elements 1508A-1508F are obstructed by resistive elements 1800A-1800F. As mentioned above, the resistive elements 1800A-1800F are configured to obstruct the flow of fluid through the fluid conduit. In some embodiments, the resistive elements are configured to obstruct the flow of aqueous humor through the fluid conduit.

As shown, the lumen plug 1800A situated in lumen 1506A operates to prevent, reduce, or otherwise limit aqueous humor from being evacuated from the anterior chamber through lumen 1506A. However, the lumen plug 1800A in lumen 1506A does not otherwise prevent, reduce, or otherwise limit the evacuation of aqueous humor through any of the other lumens 1506B-1506G of the fluid conduit 1500. In the illustrated embodiment shown in FIG. 7A, lumens 1506A-1506F are plugged with lumen plugs 1800A-1800F, respectively such that fluid is partially or fully obstructed from flowing through lumens 1506A-1506F, while lumen 1506G is unobstructed and thus operable to accommodate a flow of aqueous humor therethrough.

As mentioned above, in various embodiments, the resistive elements 1800A-1800F can be selectively ablated or alternatively removed during the implantation procedure or post-operatively (e.g., weeks, months, or years later). Thus, when the fluid conduit 1500 is implanted within an eye and configured to evacuate aqueous humor from an anterior chamber of the eye, the resistive elements 1800A-1800F can be ablated or alternatively removed during the implantation procedure or post-operatively (e.g., weeks, months, or years later) to fine tune the aqueous humor transmission rate through the fluid conduit 1500 to achieve or otherwise maintain a desired intraocular pressure.

In some embodiments the resistive element may be frictionally retained within or about the lumen. Additionally or alternatively, the resistive element may be retained by way of some other interference between the resistive element and the lumen or fluid conduit 1500, such as a flange or tab. Additionally or alternatively, the resistive element may be retained by a separate retention element, such as a luminal constricting device or other fastener that interfaces with one or both of the removable insert and the fluid conduit 1500. For example, luminal constricting device my include an o-ring disposed about a fluid conduit and a resistive element positioned within a lumen of the fluid conduit. This, it is to be appreciated that a plurality of resistive element may operate collectively to obstruct flow through the fluid conduit.

In various embodiments, the resistive elements can be formed from nylon or other suitable ablatable materials, or may additionally or alternatively be formed of a bioabsorbable material, as discussed herein. In some embodiments, the resistive elements may be porous and permeable to fluid (e.g., aqueous humor). In some such embodiments, different resistive elements may have different porosities, and therefore may exhibit differing degrees of permeability. For instance, in some embodiments, a first porous resistive element may be impermeable to aqueous humor, while a second porous resistive element may be permeable to aqueous humor such that the second porous resistive element provides for a first flow rate through (and thus a first press differential across) a first lumen of the fluid conduit 1500, while a third porous resistive element may be permeable to aqueous humor such that the third porous resistive element provides for a second flow rate greater than the first flow rate through (and thus a first press differential across) the first lumen of the fluid conduit 1500. In some such embodiments, the first porous resistive element may be post-operatively replaced with one of the second and the third porous resistive elements to modify flow through the fluid conduit 1500. Likewise, in some such embodiments, one of the second and the third porous resistive elements may be post-operatively replaced with the other of the second and the third porous resistive elements to modify flow through the fluid conduit 1500.

It should be appreciated that replacing the second resistive element having the first flow rate with the third resistive element having the second flow rate greater than the first flow rate generally increases the effective diameter of the fluid conduit 1500, which increases the flow rate through (and thus the pressure differential across) the lumen and thus the fluid conduit 1500. Conversely, replacing the third resistive element having the second flow rate with the second resistive element having the first flow rate less than the second flow rate generally reduces the effective diameter of the fluid conduit 1500, which reduces the flow rate through (and thus the pressure differential across) the lumen and thus the fluid conduit 1500.

The plurality of lumens (1506A-1506G) extending through the fluid conduit 1500 may each include a luminal diameter of the same size or of different sizes. That is, in some embodiments, the fluid conduit 1500 may include a plurality of lumens, wherein all of the lumens of the plurality of lumens have the same diameter. Alternatively, in some example, the fluid conduit 1500 may include a plurality of lumens, wherein no two lumens of the plurality of lumens have the same diameter. That is, each lumen of the plurality lumens has a diameter that differs from all of the diameters of the other lumens of the plurality of lumens. Alternatively, in some example, the fluid conduit 1500 includes a plurality of lumens, wherein at least two lumens of the plurality of lumens have the same diameter.

Additionally or alternatively, in some embodiments, one or more of the lumens of the plurality of lumens (1506A-1506G) of the fluid conduit 1500 is configured with a diameter that varies along a length of the lumen. In such embodiments, the effective diameter (and thus the resistance to flow of aqueous humor through the lumen) can be modified by varying a length of the fluid conduit 1500, as described in greater detail below.

In various embodiments, one or more of an effective length and effective diameter of the fluid conduit 1500 can be modified in advance of the implantation procedure, during the implantation procedure, or post-operatively after the procedure to modify flow through the fluid conduit. Moreover, it should be appreciated that the above-discussed configurations provide for a fluid conduit 1500 that can be modified post-operatively (e.g., over the course of days, weeks, months, or years) to incrementally and gradually increase a flow rate of fluid flowing through (and thus a pressure differential across) the fluid conduit 1500.

The plurality of individual tubular elements 1508A-1508G shown in FIG. 7B may be consistent in form and structure to the various fluid conduits illustrated and described herein (e.g., soft, thin, and flexible, with a lumen extending therethrough). However, in some embodiments, tubular elements of varying length and/or diameter may be incorporated to provide for additional fine tuning of the aqueous humor transmission rate (e.g., adjustable or titratable). That is, in some embodiments, the bundle may include a first tubular element of a first length and first diameter, and/or a second tube having a second length and a second diameter, and/or a third tube having the first diameter and the second length, and/or a fourth tube having the second diameter and the first length.

In some other embodiments, in lieu of or in addition to an ablatable lumen plug, a lumen of the fluid conduit 1500 can itself be subsequently modified to increase a flow rate (and thus a pressure differential across) the fluid conduit. For instance, in some embodiments, a lumen of the fluid conduit can be subsequently expanded (e.g., through dilation) to increase its diameter and thus the aqueous humor evacuation rate of through the lumen and thus through the fluid conduit. In some embodiments, the lumen of the fluid conduit can be expanded through thermal exposure with a laser. Such a methodology is minimally invasive and allows revision to be performed quickly in a clinic as opposed to an operating room. In some embodiments, the lumen of the fluid conduit can be mechanically dilated with the aid of an expansion accessory, such as dilator. In some embodiments, such a methodology is performed in accordance with forming and opening through an opposing corneal incision.

It will be appreciated that the fluid conduit 1500 may be pre-formed with resistive element present in each of the lumens or alternatively with one or more of the lumens unplugged or unobstructed. Likewise, it should be appreciated that the resistive elements may be positioned in one or more of a first and/or a second end of the lumen. That is, in some embodiments, a resistive element may be positioned in a first end of the lumen, while in some other embodiments, a resistive element is alternatively or additionally positioned in a second end of the lumen.

As mentioned above, in some embodiments, the resistive elements are selectively ablatable via one or more laser ablation processes. That is, in, as mentioned above. In some such embodiments, a physician may utilize optical energy to ablate or eliminate the resistive element. In other embodiments, the resistive element may be mechanically retrieved by the physician and withdrawn from the fluid conduit. In some other embodiments, the resistive elements can be selectively ablated or may be configured to bioabsorb (such as after a designated period of time, or in association with exposure to a designated differential pressure, such as between the intraocular pressure and the aqueous humor diffusion member pressure).

Figure 8:
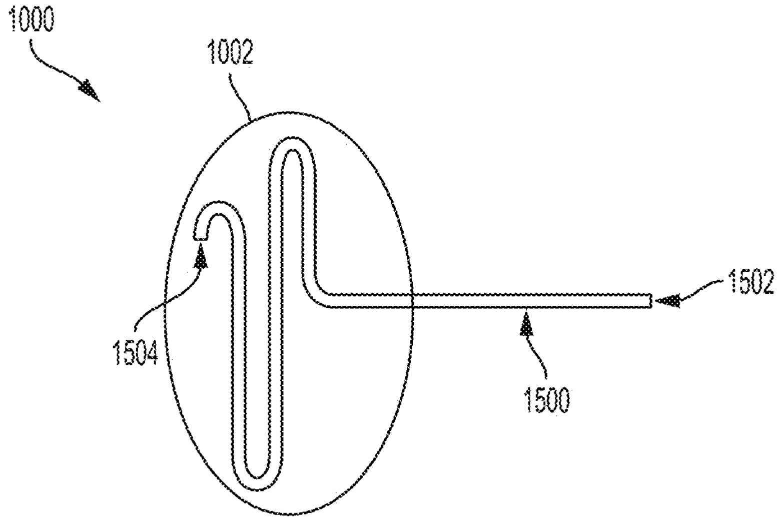
FIG. 8 is an illustration of a glaucoma drainage system consistent with various aspects of the present disclosure.

As discussed above, in various embodiments, in addition to or in lieu of modifying an effective luminal diameter of the fluid conduit 1500, a flow rate through (and thus a pressure differential across) the fluid conduit 1500 may be modified through a modification of the effective length of the fluid conduit 1500. Turning now to FIG. 8, a glaucoma drainage system 1000 is shown. The glaucoma drainage system 1000 includes an aqueous humor diffusion member 1002, and a fluid conduit 1500 fluidly coupled to the aqueous humor diffusion member 1002.

As shown, the fluid conduit 1500 includes an excess length that is stored within an interior of the aqueous humor diffusion member 1002. For example, the excess length of the fluid conduit 1500 may be stored within a reservoir defined within the aqueous humor diffusion reservoir. In some embodiments, the fluid conduit 1500 includes a first section having a first length stored within an interior region of the aqueous humor diffusion member 1002, and a second section having a second length extending exterior to the aqueous humor diffusion member 1002.

It is to be appreciated that the fluid conduit 1500 may be helically coiled, accordioned, randomly coiled, or coiled according to any other suitable manner within the interior of the aqueous humor diffusion member 1002. It is also to be appreciated that the excess length of the fluid conduit 1500 may be subsequently reduced post-operatively to increase a flow rate through (and thus a pressure differential across) the fluid conduit 1500, as discussed in greater detail below.

In some embodiments, the fluid conduit 1500 is configured to slide or otherwise translate relative to the aqueous humor diffusion member 1002 such that the first end 1502 of the fluid conduit 1500 can be tensioned to draw additional length of the fluid conduit 1500 out of the interior region of the aqueous humor diffusion member 1002. By tensioning the fluid conduit 1500 and thereby drawing a portion of the excess length previously stored within the aqueous humor diffusion member 1002 out of the aqueous humor diffusion member 1002, the excess length of the fluid conduit 1500 stored within the aqueous humor diffusion member 1002 is reduced. That is, tensioning the fluid conduit may extend a length of the second section of the fluid conduit 1500 extending exterior to the aqueous humor diffusion member 10002 while decreasing a length of the first section of the fluid conduit 1500 stored within the interior of the aqueous humor diffusion member 1002.

In some embodiments, the glaucoma drainage system 1000 may include a sleeve that is coupled to the aqueous humor diffusion member 1002, and through which the fluid conduit 1500 extends. In some embodiments, the fluid conduit 1500 is slideable relative to the sleeve (not shown).

It should be appreciated that while an excess portion of the fluid conduit 1500 is described as being stored within an interior of the aqueous humor diffusion member 1002, excess portions of the fluid conduit 1500 may additionally or alternatively be stored within the anterior chamber (AC) of the patient's eye.

In some embodiments, after tensioning the fluid conduit 1500 and drawing a portion of the excess fluid conduit 1500 out of the interior of the aqueous humor diffusion member 1002, a portion of the fluid conduit 1500 extending exterior to the aqueous humor diffusion member 1002 can be trimmed away. In some embodiments, a length of the fluid conduit 1500 trimmed away may correspond in length to the length of the excess fluid conduit 1500 previously drawn out of the interior of the aqueous humor diffusion member 1002. However, it will be appreciated that the trimmed length may correspond to a length differing from that of the length of the excess fluid conduit 1500 previously drawn out of the interior of the aqueous humor diffusion member 1002.

By trimming a portion of the length of the fluid conduit 1500, the effective length of the fluid conduit 1500 is reduced. In those embodiments where a diameter of the lumen of the fluid conduit 1500 remains constant or increases along the length of the fluid conduit 1500 (such that the average diameter of the portion trimmed away is equal to or less than the average diameter of the remaining portion of the fluid conduit 1500), trimming away a portion of the length of the fluid conduit 1500 has the effect of increasing the flow through (and thus the pressure differential across) the fluid conduit 1500. It will thus be appreciated that in those embodiments where a diameter of the lumen of the fluid conduit 1500 remains decreases along the length of the fluid conduit 1500 (such that the average diameter of the portion trimmed away is greater than the average diameter of the remaining portion of the fluid conduit 1500), trimming away a portion of the length of the fluid conduit 1500 has the effect of decreasing the flow through (and thus the pressure differential across) the fluid conduit 1500.

The novel concepts of this application has been described above both generically and with regard to specific embodiments. It will be apparent to those skilled in the art that various modifications and variations can be made in the embodiments without departing from the scope of the disclosure. Thus, it is intended that the embodiments cover such modifications and variations provided they come within the scope of the appended claims and their equivalents.

In some embodiments, the glaucoma drainage systems discussed herein may be implanted ab-internally (e.g., from inside the eye), such as through a clear-corneal incision, and placed through the sclera and into a dissected subconjunctival space, as those of skill in the art will appreciate. In some other embodiments, the glaucoma drainage systems are implantable ab-externally (e.g., from outside of the eye), such as through a conjunctival incision, as those of skill in the art should appreciate. In some embodiments, a conjunctival radial incision is performed typically near the limbal junction, and blunt dissection of the conjunctiva is performed to expose the sclera and provide a site for placement of aqueous humor diffusion member. In some embodiments, this may require suturing of the aqueous humor diffusion member to the sclera. In some embodiments, a small needle, typically a 22 or 23 gauge needle, is also inserted near the scleral spur to provide a track for subsequent insertion and placement of the fluid conduit into the anterior chamber. Similarly, it will be appreciated that the various fluid conduit modifications discussed above may be performed through one or more of and ab-internal clear-corneal approach and an ab-external approach As discussed above, in various embodiments, the aqueous humor diffusion members discussed herein are formed of a plurality of diffusion membranes including a proliferation diffusion membrane and a constriction diffusion membrane, where the porosity or permeability to aqueous humor of the proliferation diffusion membrane exceeds the porosity of the constriction diffusion membrane. Thus, the disclosed aqueous humor diffusion members comprise a plurality of different membranes having different degrees of porosity (e.g., different quantity of pores and/or pores having different sizes). Generally, different diffusion membranes having different degrees of porosity will be associated with different rates at which aqueous humor diffuses into the associated membrane (also described as flux). For example, the aqueous humor diffusion member may be configured such that an amount of aqueous humor diffuses into the constriction diffusion membranes at a different rate (e.g., a lower flux) than the amount of aqueous humor diffuses into the proliferation diffusion membranes (e.g., higher flux). Thus, the aqueous humor diffusion member may be configured such that aqueous humor diffuses into a first region of the aqueous humor diffusion member at a different rate than the aqueous humor diffuses into a second region of the aqueous humor diffusion member.

As discussed above, in various embodiments, the layers of polymeric material(s) forming the diffusion membranes may be coupled together at one or more discrete locations to form stabilizing structures that extend through the diffusion membrane. In some embodiments, during a lamination process, the various layers forming the diffusion membrane may be laminated together such that one or more discrete pillar or column-like structures extend through the diffusion membrane from a first interface surface of the diffusion membrane to a second interface surface of the diffusion membrane. In various embodiments, these pillar or column-like structures can be formed of adhesives. In some embodiments, one or more of these pillars can effectively hold open or otherwise maintain an effective strainable, shearable, slideable interface such that the glaucoma drainage system is flexible and is operable to accommodate the evacuated aqueous humor. Additionally, in some embodiments, unintended expansion (e.g., ballooning) of the aqueous humor diffusion member beyond a designated amount or beyond a designated profile can be minimized and/or avoided by discretely bonding adjacently facing interface surfaces of adjacently situated diffusion membranes, as mentioned above.

As mentioned above, in various embodiments, the fluid conduit and/or the body of the aqueous humor diffusion member can be formed from soft and compliant materials to create a construct that conforms to the curvature of the eye, which helps minimizes relative movement between the glaucoma drainage systems and the surrounding tissue that can lead to tissue irritations, foreign body tissue response, excessive scar formation, and/or erosion. Another potential problem experienced with conventional designs includes erosion of the fluid conduit through the conjunctiva, generally proximate the region where the fluid conduit passes through the sclera and extends into the anterior chamber of the eye. Conjunctival erosion in this manner can lead to direct exposure of the anterior chamber, providing a pathway for bacteria to enter the eye, a risk of endophthalmitis, and potential loss of vision in the eye.

Though a number of approaches have been attempted to minimize the potential of such erosion through the conjunctiva, none of the known solutions include a singular device or system that combines aqueous humor drainage while protecting against erosion of the fluid conduit.

Figure 9A:
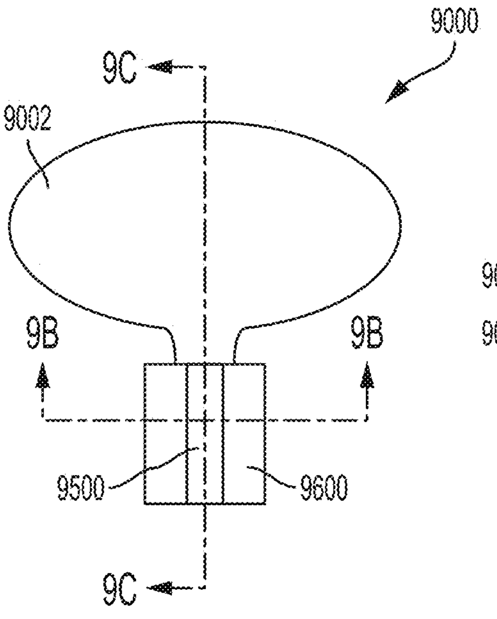
FIG. 9A is an illustration of a glaucoma drainage system consistent with various aspects of the present disclosure.
Figure 9B:
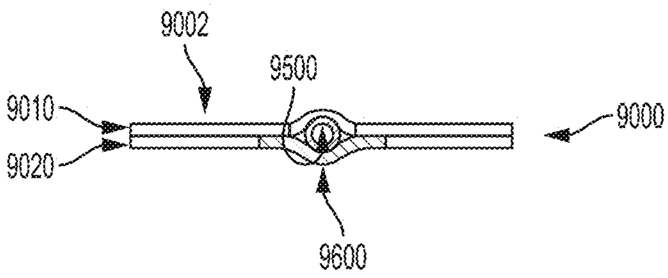
FIG. 9B is cross sectional view of the glaucoma drainage system of FIG. 9A taken along line 9B-9B.
Figure 9C:
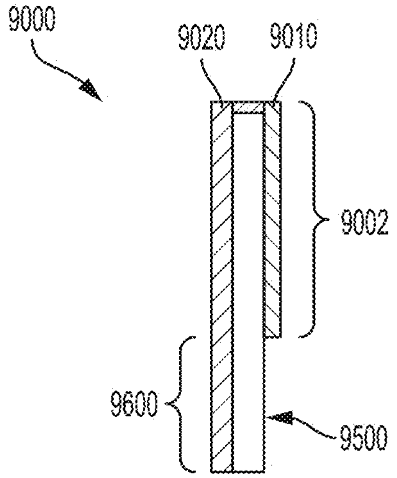
FIG. 9C is cross sectional view of the glaucoma drainage system of FIG. 9A taken along line 9C-9C.
Figure 10:
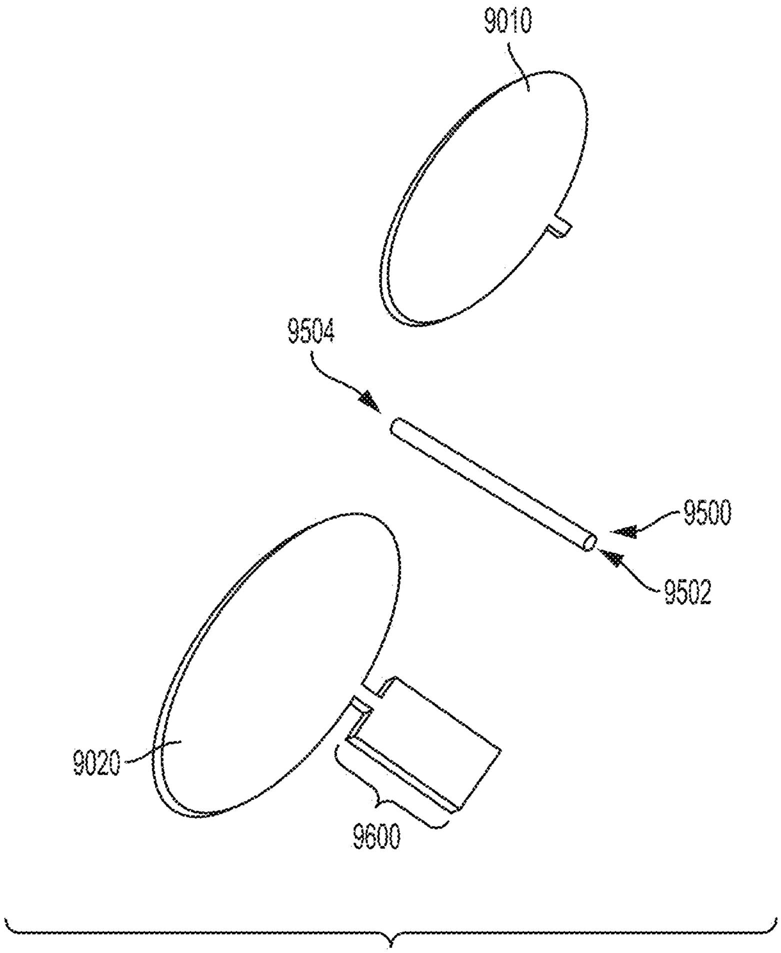
FIG. 10 is an exploded view of a glaucoma drainage system consistent with various aspects of the present disclosure.

Turning now to FIGS. 9A to 10, in various embodiments, a glaucoma drainage system 9000 includes an aqueous humor diffusion member 9002 and a fluid conduit 9500. The fluid conduit 9500 may be consistent in construction, form, makeup, and function to the various fluid conduits (e.g., fluid conduit 1500) discussed above. Similarly, the aqueous humor diffusion member 9002 may be consistent in construction, form, makeup, and function to the various aqueous humor diffusion members (e.g., aqueous humor diffusion member 1002) discussed above, but with the exception that the aqueous humor diffusion member 9002 additionally includes one or more erosion elements 9600.

In various embodiments, an erosion element 9600 is an element, feature, component, or portion of the glaucoma drainage system 9000 that overlays a portion of the fluid conduit 9500 to help minimize erosion of the fluid conduit 9500 through one or more tissues of the eye when the glaucoma drainage system 9000 is implanted. As discussed above, in various embodiments, the glaucoma drainage system 9000 is implantable within a pocket formed between the conjunctiva and the sclera of the eye, as those of skill will appreciate.

In some instances, for example, the erosion element 9600 extends from the body of the glaucoma drainage system 9000 to overlay the fluid conduit 9500. The erosion element 9600 operates as a protective barrier between the fluid conduit 9500 and one or more surrounding tissues of the eye. For example, the glaucoma drainage system 9000 may be configured such that an erosion element 9600 extends along the fluid conduit 9500 between the fluid conduit 9500 and a conjunctiva of the eye when implanted. In some such embodiments, the erosion element 9600 helps minimize or even prevent erosion of the fluid conduit 9500 through the conjunctiva by forming a barrier between the fluid conduit 9500 and the conjunctiva when the glaucoma drainage system 9000 is implanted in the eye, as discussed further below.

In some embodiments, the erosion element 9600 forms an integral, non-separable element, feature, component, or portion of the glaucoma drainage system 9000. In some other embodiments, the erosion element 9600 is formed as a distinct element or component that is coupled with one or more portions of the glaucoma drainage system 9000. In some such embodiments, the erosion element 9600 may be coupled with the one or more portions of the glaucoma drainage system 9000 and thereby become integral to the glaucoma drainage system 9000. Alternatively, in some embodiments, the erosion element 9600 may be coupled with the one or more portions of the glaucoma drainage system 9000 such that the erosion element 9600 can be subsequently separated and removed from the glaucoma drainage system 9000.

As indicated above, the glaucoma drainage system 9000 may include multiple (or a plurality of) erosion elements 9600. In some such embodiments, the fluid conduit 9500 of the glaucoma drainage system 9000 may be isolated from interfacing with the surrounding tissue of the eye (e.g., a sclera or a conjunctiva) by the incorporation of multiple erosion elements 9600. That is, in some embodiments, the glaucoma drainage system 9000 may include one or more erosion elements 9600 that isolate the fluid conduit 9500 of the glaucoma drainage system 9000 from the tissue of the eye. For instance, the glaucoma drainage system 9000 may be configured such that erosion elements 9600 flank the fluid conduit 9500 on either side of a plane bisecting the fluid conduit 9500 along a longitudinal axis thereof. In such a configuration, for example, a first one of the erosion elements 9600 may extend along the fluid conduit 9500 between the fluid conduit 9500 and a sclera of the eye. Similarly, a second one of the erosion elements 9600 may extend along the fluid conduit 9500 between the fluid conduit 9500 and a conjunctiva of the eye. Such a configuration provides erosion protection for both a conjunctiva and a sclera of an eye when the glaucoma drainage system 9000 is implanted in the eye (e.g., when implanted within a pocket formed between the conjunctiva and the sclera), as the fluid conduit 9500 is prevented from directly interfacing with the conjunctiva and the sclera of the eye.

As mentioned above, with the exception of the erosion element 9600, the glaucoma drainage system 9000 is similar in construction, form, and makeup to the other glaucoma drainage systems discussed herein (e.g., glaucoma drainage system 1000). Thus, in various embodiments, the glaucoma drainage system 9000 comprises a multilayered construction and is configured to help drain aqueous humor from the anterior chamber of the eye by facilitating not only the evacuation of aqueous humor from within the anterior chamber of the eye, but also reabsorption of the evacuated aqueous humor by the body, for example. Like the glaucoma drainage system 1000, in various embodiments, the glaucoma drainage system 9000 similarly includes one or more constriction diffusion membranes and one or more proliferation diffusion membranes organized to optimize aqueous humor drainage and reabsorption (see discussion above).

In various embodiments, the erosion element 9600 includes a thin, flexible, porous membrane consistent in construction, form, and makeup with the various other thin, flexible, porous membranes discussed herein (e.g., the diffusion membranes discussed above). For example, the erosion element 9600 may include a microstructure that is configured to resist tissue ingrowth (e.g., a constriction diffusion membrane), or may alternatively include a microstructure that is configured to promote or permit tissue ingrowth (e.g., proliferation diffusion membrane). Alternatively, in some embodiments, the erosion element 9600 may comprise a multilayered construct including a first membrane configured to promote or permit tissue ingrowth (e.g., proliferation diffusion membrane) and a second membrane configured to resist tissue or cellular ingrowth (e.g., a constriction diffusion membrane). The permittive/resistive membranes in such embodiments are oriented to optimize their effect when the glaucoma drainage system 9000 is implanted in the eye. For instance, as discussed in greater detail below, in various embodiments, the erosion element 9600 is configured to promote or permit tissue ingrowth along an interface between the erosion element 9600 and a tissue of the eye (e.g., such as the sclera or the conjunctiva). It will thus be appreciated that the material of the erosion element 9600 may include any material and may be constructed according to any method discussed herein as being suitable for the diffusion membranes discussed above.

Accordingly, in various embodiments, the erosion element 9600 may be coupled with (or alternatively may be an extension of or integral with) any of the various proliferation diffusion membranes or constriction diffusion membranes discussed herein. Thus, in some embodiments, the erosion element 9600 may itself be a constriction diffusion membrane (e.g., configured to minimize, resist, or prevent tissue ingrowth) or a proliferation diffusion membrane (e.g., configured to permit tissue ingrowth). In some such embodiments, the erosion element 9600 is a constriction diffusion membrane coupled to or integral with a constriction diffusion membrane of the aqueous humor diffusion member. Additionally or alternatively, in some embodiments, the erosion element 9600 is a constriction diffusion membrane coupled to a proliferation diffusion membrane of the aqueous humor diffusion member. In some embodiments, the erosion element 9600 is a proliferation diffusion membrane coupled to a constriction diffusion membrane of the aqueous humor diffusion member. In some embodiments, the erosion element 9600 is a proliferation diffusion membrane coupled to or integral with a proliferation diffusion membrane of the aqueous humor diffusion member.

Referring to FIGS. 9A to 9C and 10, a glaucoma drainage system 9000 is shown. FIG. 9A is a top view of the glaucoma drainage system. FIG. 9B is a cross-sectional view of the glaucoma drainage system 9000 taken along line 9B-9B in FIG. 9A. FIG. 9C is a cross-sectional view of the glaucoma drainage system 9000 taken along line 9C-9C in FIG. 9A. FIG. 10 is an exploded view of the glaucoma drainage system 9000.

As shown, the glaucoma drainage system 9000 includes an aqueous humor diffusion member 9002, a fluid conduit 9500 (e.g., a shunt), and an erosion element 9600. The aqueous humor diffusion member 9002 includes a plurality of layers including a first stratum 10010 and a second stratum 10020. The first and second stratum 10010 and 10020 each include one or more diffusion membranes configured to promote or permit tissue ingrowth (e.g., proliferation diffusion membrane) and/or one or more diffusion membranes configured to resist tissue ingrowth (e.g., a constriction diffusion membrane). Thus, it will be appreciated that the first stratum 10010 may be comprised of one or more diffusion membranes configured to promote or permit tissue ingrowth and one or more diffusion membranes configured to minimize, resist, or prevent tissue ingrowth. Similarly, it will be appreciated that the section stratum 10020 may additionally or alternatively be formed of one or more diffusion membranes configured to promote or permit tissue ingrowth and one or more diffusion membranes configured to minimize, resist, or prevent tissue ingrowth. Thus, it will be appreciated that the aqueous humor diffusion member 9002 may be similar in construction, form, and function to the various other aqueous humor diffusion members discussed herein.

As shown in FIGS. 9A-11, the glaucoma drainage system 9000 includes an erosion element 9600. The erosion element 9600 extends away from the aqueous humor diffusion member 9002 of the glaucoma drainage system 9000 as shown. In some embodiments, the erosion element 9600 extends away from the aqueous humor diffusion member 9002 along the fluid conduit 9500 between the fluid conduit 9500 and the aqueous humor diffusion member 9002. In some embodiments, the erosion element 9600 extends between the aqueous humor diffusion member 9002 and an end of the fluid conduit 9500 (e.g., a first end or a second end of the fluid conduit 9500) that is configured to access a biological fluid-filled body cavity, such as an anterior chamber of an eye, among other embodiments as will be appreciated by those of skill in the art.

Though illustrated in FIGS. 9A to 9C and 10 as including a rectangular shape, it will be appreciated that the erosion element 9600 may be of any suitable shape without departing from the spirit or scope of the disclosure. For instance, the erosion element 9600 may be square, rectangular, trapezoidal, or some other polygonal shape, and may include chamfered or rounded edges between sides, and the sides may be linear or generally curved in nature. The erosion element 9600 may have a generally continuous curved edge in that it is circular or ovular, or of another suitable shape (e.g., bean-shaped). It is to be appreciated that one of skill in the art will appreciate that the erosion element 9600 may be of any desired shape provided that the erosion element 9600 helps protect against erosion of the fluid conduit through tissue surrounding the fluid conduit and provided the erosion element 9600 can be placed within a subconjunctival space (such as a pocket formed between the conjunctiva and the sclera) as described herein.

In some embodiments, the erosion element 9600 extends along a length of the fluid conduit, but includes a length that is shorter than a length of the portion of the fluid conduit extending from the aqueous humor diffusion member 9002. In other embodiments, the erosion element 9600 extends along a length of the fluid conduit, and includes a length that is equal to or greater than a length of the portion of the fluid conduit extending from the aqueous humor diffusion member 9002. In some embodiments, the erosion element 9600 has a width that is greater than or equal to a diameter of the fluid conduit 9500. However, in some embodiments, the width of the erosion element 9600 may be less than the diameter of the fluid conduit, provided that the erosion element 9600 is not rendered ineffective against helping protect against erosion of the fluid conduit through surrounding tissue. Consistent with the versatility in suitable sizes and shapes of the erosion element 9600 discussed above, it will be appreciated that the width of the erosion element 9600 may remain constant along the length of the erosion element 9600, or alternatively, the width of the erosion element 9600 may vary along the length of the erosion element 9600. For example, the width may taper (linearly or nonlinearly) along the longitudinal length of the erosion element.

In some embodiments, the erosion element 9600 may be configured such that it is more abrasion resistant in high wear or high abrasion areas (e.g., areas where the fluid conduit 9500 has a potential to move relative to the erosion plate 9600). Resistance to abrasion in such areas may be accomplished according to any known methods, including material compositions and/or material thickness. A thickness of the erosion element 9600 may thus vary along the length of the erosion element 9600, and/or may vary laterally across its width. For example, the thickness may taper (linearly or nonlinearly) along the length of the erosion element 9600 and/or transversely thereacross. For instance, a thickness of the erosion element 9600 along a longitudinally extending centerline may be in excess of a thickness of the erosion element 9600 along one or more of its longitudinally extending edges. Alternatively, it will be appreciated that a thickness of the erosion element 9600 along a longitudinally extending centerline may be less than a thickness of the erosion element 9600 along one or more of its longitudinally extending edges. Additionally or alternatively, a thickness of the erosion element 9600 along a section of its longitudinal length may be in excess of a thickness of the erosion element 9600 along a second section of its longitudinal length. For example, if a region where the fluid conduit 9500 accesses the fluid-filled body cavity corresponds to a high abrasion region, a section of the erosion element 9600 that is more proximate the end of the fluid conduit 9500 that is configured to access the fluid-filled body cavity may be thicker than is a section of the erosion element 9600 that is more proximate the aqueous humor diffusion member 9002. It is to be appreciated that a thickness of the erosion plate 9600 can be optimized in high wear or high abrasion areas to reduce a risk of premature failure of the glaucoma drainage system 9000, due to abrasion of the erosion plate 9600 by the fluid conduit 9500. These variances in thickness may be achieved through selective layering of materials that collectively form the erosion element 9600 or other known methods.

In some embodiments, the erosion element 9600 may be longitudinally spaced apart from the aqueous humor diffusion member 9002, or may include a region of reduced width (e.g., as illustrated in FIG. 10) and/or thickness (not illustrated) extending between the erosion element 9600 and the aqueous humor diffusion member 9002 along those regions of the fluid conduit 9500 that are associated with a low risk of erosion through the surrounding tissue. For example, if the portion of the fluid conduit 9500 adjacent the aqueous humor diffusion member 9002 is associated with a low risk of erosion through the surrounding tissue, a region of reduced width and/or thickness of the erosion element 9600 may be situated adjacent this region of the fluid conduit 9500. Alternatively, the erosion element 9600 may be configured such that the fluid conduit 9500 is exposed to the surrounding tissue in this region of low risk for erosion. Thus, in some examples, the erosion element 9600 may not extend from the aqueous humor diffusion member 9002.

In some embodiments, the erosion element 9600 is coupled to the fluid conduit 9500. The erosion element 9600 may be coupled to the fluid conduit 9500 continuously along a length of the fluid conduit 9500, or alternatively along the fluid conduit 9500 at one or more discrete locations. The erosion element 9600 may be coupled to the fluid conduit 9500 according to any known methods including, but not limited to suturing or stitching of the erosion element along the length of the conduit. In some embodiments, suturing can be a series of interrupted sutures or a continuous running stitch. Additionally or alternatively, the fluid conduit 9500 can be mechanically adhered to the erosion element 9600 by partially melting the fluid conduit 9500 into the microporous structure of the erosion element 9600. In some embodiments, the erosion element 9600 may be coated with an adhesive that is tacky such that the fluid conduit 9500 can releasably stick to the erosion element 9600. In some embodiments, one or more bands of material (e.g., microporous material) can have their ends adhered to the erosion element 9600 such that an eyelet is formed between the band of material and the erosion element 9600 and the fluid conduit 9500 can be threaded through the gap.

Figure 11:
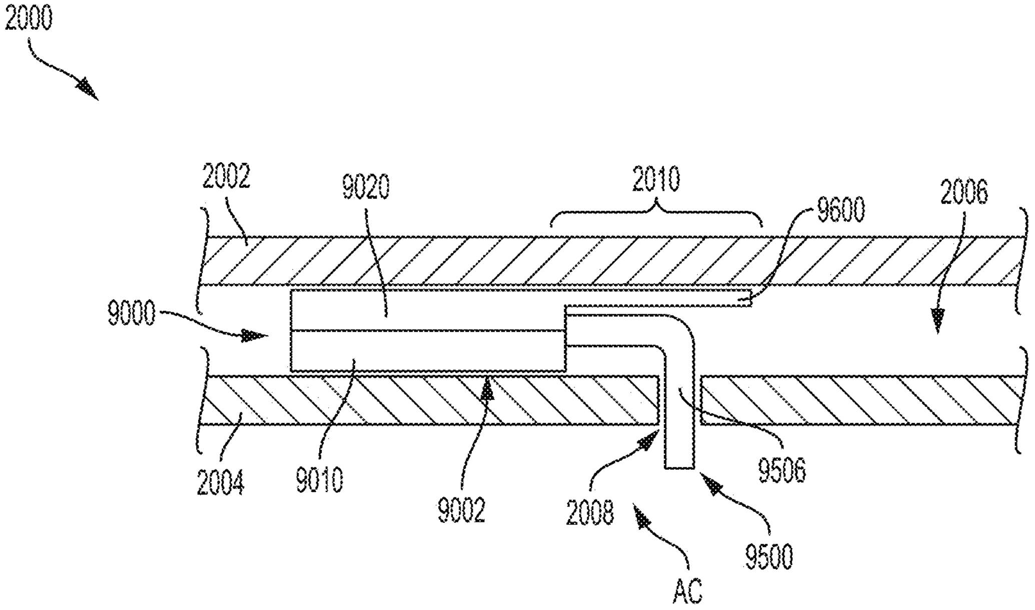
FIG. 11 is an illustration of a glaucoma drainage system implanted within an eye tissue consistent with various aspects of the present disclosure.
Figure 12:
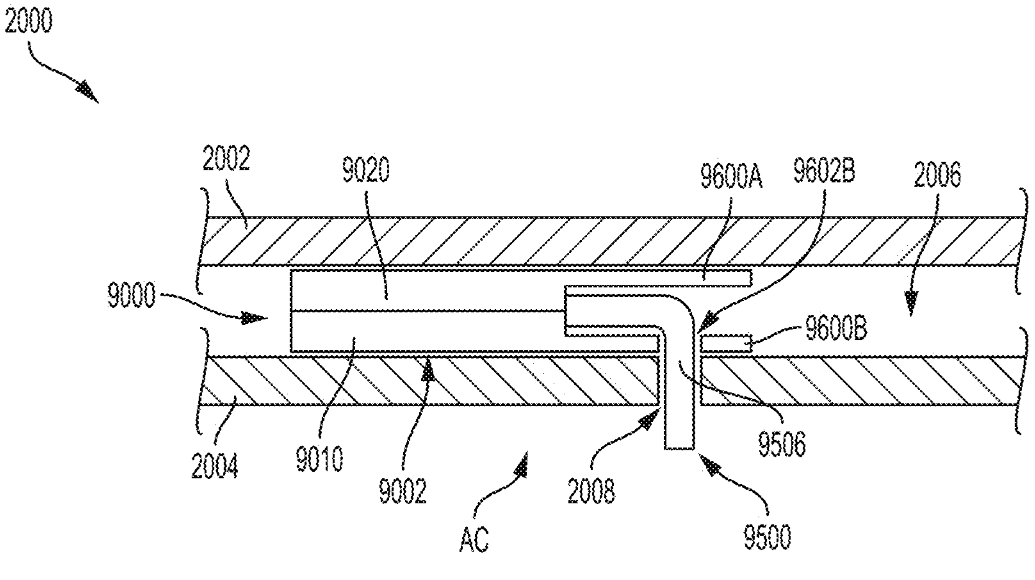
FIG. 12 is an illustration of a glaucoma drainage system consistent with various aspects of the present disclosure.

As discussed above, when used to treat conditions such as glaucoma, the glaucoma drainage system 9000 may be situated within a subconjunctival space (e.g., a pocket formed between the conjunctiva and the sclera of the eye). The glaucoma drainage system 9000 is situated such that it adopts a relatively flat and minimal radial profile within the subconjunctival space, and such that the anterior chamber of the eye can be accessed by the fluid conduit 9500. With reference now to FIGS. 10 and 11, glaucoma drainage systems are illustrated in implanted configurations. FIG. 11 includes a glaucoma drainage system 9000 having an aqueous humor diffusion member 9002, a fluid conduit 9500, and an erosion element 9600. FIG. 12 includes a glaucoma drainage system 9000 having an aqueous humor diffusion member 9002, a fluid conduit 9500, and a plurality of first and second erosion elements 9600A and 9600B.

With reference to FIG. 11, for example, the glaucoma drainage system 9000 is shown disposed in a subconjunctival space 2006 between the conjunctiva 2002 and the sclera 2004 of the eye 2000. The glaucoma drainage system 9000 is shown oriented such that the first stratum 10010 extends along the sclera 2004 and such that the second stratum 10020 extends along the conjunctiva 2002. It will be appreciated that the portion of the second stratum 10020 that interfaces with the conjunctiva 2002 may be configured to promote or permit tissue ingrowth, as discussed above. It will also be appreciated that the portion of the first stratum 10010 that interfaces with the sclera may additionally or alternatively be configured to promote or permit tissue ingrowth, as discussed above. Such configurations help minimize relative movement between the aqueous humor diffusion member 9002 and the surrounding tissue.

Moreover, the fluid conduit 9500 is shown in FIG. 11 as extending from the aqueous humor diffusion member 9002, and extending through a scleral access, perforation, or hole 2008 (e.g., made by a physician during the implantation procedure according to known methods) such that a first end 9502 accesses the anterior chamber (AC). Additionally, as shown the erosion element 9600 extends between the fluid conduit 9500 and the conjunctiva 2002 of the eye 2000. In particular, the erosion element 9600 extends between the fluid conduit 9500 and the conjunctiva 2002 such that a portion of the erosion element 9600 is positioned adjacent or proximate the scleral access 2008 and/or adjacent or proximate the portion 9506 of the fluid conduit extending through the scleral access 2008. Such a configuration provides that the conjunctiva 2002 is not directly exposed to the fluid conduit 9500. Instead, as shown, the erosion element 9600 extends along the conjunctiva 2002. This configuration helps protect against erosion of the fluid conduit 9500 thorough the conjunctiva 2002, as the erosion element 9600 operates as a protective barrier between the conjunctiva 2002 and the fluid conduit 9500. For example, the erosion element 9600 operates as a protective barrier between the fluid conduit and a portion 2010 of the conjunctiva positioned adjacent or proximate the scleral access 2008, as shown.

It will be appreciated that, the portion of the erosion element 9600 that interfaces with the conjunctiva 2002 may be configured to promote or permit tissue ingrowth, as discussed above. Such a configuration helps minimize relative movement between the erosion element 9600 and the conjunctiva, even where relative movement may exist between the fluid conduit 9500 and the erosion element 9600.

Though the erosion element 9600 is shown in FIG. 11 as including a portion that extends beyond the scleral access 2008 (and thus the portion of the fluid conduit 9500 extending through the scleral access), in some embodiments, the erosion element 9600 may extend up to or even short of the scleral access 2008 provided the erosion element 9600 is not rendered ineffective against helping protect against erosion.

In some embodiments, when implanted, aqueous humor enters the first end 9502 of the fluid conduit 9500 and travels to a second end 9504 of the fluid conduit in fluid communication with the aqueous humor diffusion member 9002. In some embodiments the second end 9504 is positioned within the aqueous humor diffusion member 9002 in the same manner discussed above with regard to the second end 1504 of the fluid conduit 1500 and the aqueous humor diffusion member 1002. Accordingly as discussed above, the evacuated aqueous humor enters a reservoir defined within the aqueous humor diffusion member 9002 and percolates through the various diffusion membranes of the aqueous humor diffusion member 9002, where the aqueous humor is then absorbable by the surrounding and/or ingrown tissue.

Turning now to FIG. 12, a glaucoma drainage system 9000 is shown disposed in a subconjunctival space 2006 between the conjunctiva 2002 and the sclera 2004 of the eye 2000. The configuration of the glaucoma drainage system 9000 shown in FIG. 12 is similar to the configuration of the glaucoma drainage system 9000 shown in FIG. 11 with the exception that the glaucoma drainage system 9000 shown in FIG. 12 includes two erosion elements (e.g., a first erosion element 9600A and a second erosion element 9600B). The first erosion element 9600A, corresponds in construction, form, and function to the erosion element 9600 discussed above with regard to FIG. 11. It will be appreciated that while the glaucoma drainage system 9000 shown in FIG. 12 includes second erosion element 9600B in combination with first erosion element 9600A, a glaucoma drainage system may include second erosion element 9600B without also requiring first erosion element 9600A. That is, in some embodiments, the glaucoma drainage system 9000 may be configured to include an erosion element that extends between the fluid conduit 9500 and the sclera 2004 without also requiring an erosion element that extends between the fluid conduit 9500 and the conjunctiva 2002.

Additionally, as shown in FIG. 12, the fluid conduit 9500 extends through an aperture 9602B of the second erosion element 9600B before extending through the scleral access, perforation, or hole 2008 (e.g., made by a physician during the implantation procedure according to known methods) and into the anterior chamber (AC). Thus, it will be appreciated that in various embodiments, an erosion element (such as second erosion element 9600B) may include one or more incisions, perforations, or apertures that are configured to accommodate the fluid conduit 9500. In some embodiments, the second erosion element 9600B is constructed or manufactured with such a preformed aperture. In some other embodiments, an incision, perforation, or aperture may be formed in the erosion element during the implantation procedure or just prior thereto. In some embodiments, the incision, perforation, or aperture is formed by the physician or a physician's assistant.

As shown, the second erosion element 9600B extends between the fluid conduit 9500 and the sclera 2004, while the first erosion element 9600A extends between the fluid conduit 9500 and the conjunctiva 2002. Though the second erosion element 9600B shown in FIG. 12 includes aperture 9602B and thus a portion thereof that extends beyond the scleral access 2008, it will be appreciated that the second erosion element 9600B may not extend up to or beyond the scleral access 2008, and thus may not require an aperture 9602B. In such configurations, the second erosion element 9600B may extend between the sclera 2004 and the fluid conduit 9500 to a position short of the scleral access 2008 (not shown).

Configurations including an erosion element that is positionable between the fluid conduit 9500 and the sclera 2004 provide that the sclera 2004 is not directly exposed to the fluid conduit 9500. Such configurations help protect against erosion of the fluid conduit 9500 thorough the sclera 2004, as such erosion elements operate as a protective barrier between the sclera 2004 and the fluid conduit 9500.

In some embodiments, the portion of the second erosion element 9600B that interfaces with the sclera 2004 may be configured to promote or permit tissue ingrowth, as discussed above. Such a configuration helps minimize relative movement between the second erosion element 9600B and the sclera 2004, even where relative movement may exist between the fluid conduit 9500 and the second erosion element 9600B.

Figure 13:
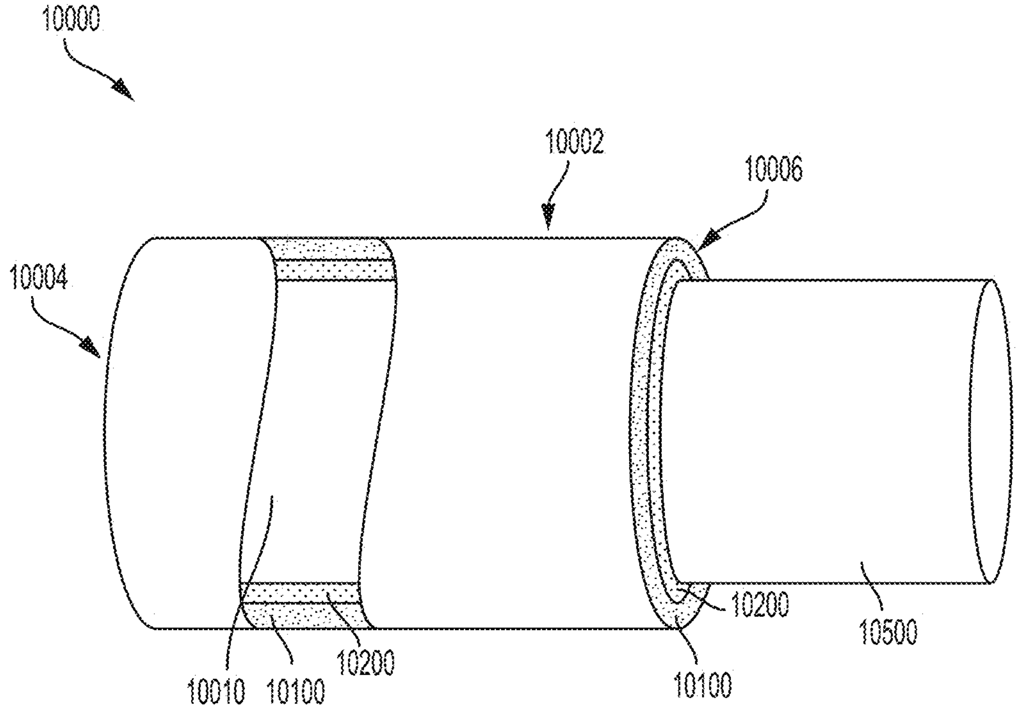
FIG. 13 is an illustration of a glaucoma drainage system consistent with various aspects of the present disclosure.

In some alternative embodiments, an aqueous humor diffusion member may have a tubular or cylindrical profile including a plurality of concentrically situated diffusion membranes. For example, an aqueous humor diffusion member may include a tubular constriction diffusion membrane and a tubular proliferation diffusion membrane, where the tubular constriction diffusion membrane corresponds to an interior diffusion membrane that is concentric with the proliferation diffusion membrane, which defines an exterior of the aqueous humor diffusion member. Turing now to FIG. 13, a glaucoma drainage system 10000 is shown and includes an aqueous humor diffusion member 10002 that is defined by an outer tubular proliferation diffusion membrane 10100 that is concentric with an inner tubular constriction diffusion membrane 10200. A portion of the aqueous humor diffusion member 10002 is shown cut away to expose the interior region of the aqueous humor diffusion member 10002. As shown, a reservoir 10010 is defined within a central lumen of the inner tubular constriction diffusion membrane 10200, and a fluid conduit 10500 is fluidly coupled with the reservoir 10010 at a second end 10006 of the aqueous humor diffusion member 10002. In some embodiments, the concentric diffusion membranes of the aqueous humor diffusion member 10002 shown in FIG. 13 may be uncoupled or partially uncoupled with one another, as discussed herein. In some embodiments, at least one end (e.g., the first end 10004 which is opposite the fluid conduit 10500) of the aqueous humor diffusion member 10002 is sealed to cause evacuated aqueous humor to percolate through the concentric diffusion membranes of the aqueous humor diffusion member 10002.

Figure 14A:
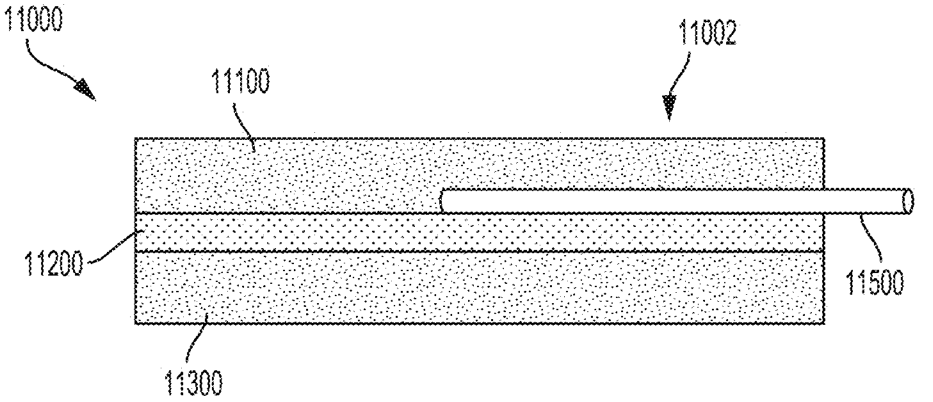
FIG. 14A is an illustration of a glaucoma drainage system in a deflated state consistent with various aspects of the present disclosure.
Figure 14B:
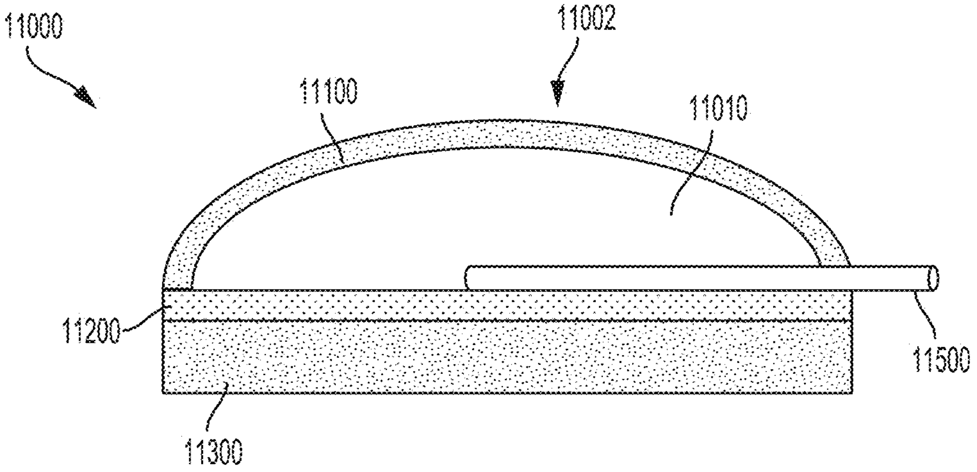
FIG. 14B is an illustration of a glaucoma drainage system in an inflated state consistent with various aspects of the present disclosure.

While the aqueous humor diffusion member 1002 illustrated and described herein includes a body defined by four diffusion membranes, the body of the aqueous humor diffusion member 1002 may alternatively be defined by as little as three diffusion membranes or in excess of four diffusion membranes without departing from the spirit or scope of the present disclosure. For example, while the above-discussed embodiments include an aqueous humor diffusion member 1002 including a plurality of constriction diffusion membranes and a plurality of proliferation diffusion membranes, in some embodiments, a glaucoma drainage system may include an aqueous humor diffusion member having a constriction diffusion membrane that is sandwiched between a plurality of proliferation diffusion membranes. For example, turning now to FIGS. 14A and 14B, a glaucoma drainage system 11000 is shown and includes an aqueous humor diffusion member 11002 defined by a first proliferation diffusion membrane 11100, a first constriction diffusion membrane 11200 and a second proliferation diffusion membrane 11300. As shown, the first constriction diffusion membrane 11200 is situated between the first and second proliferation diffusion membranes 11100 and 11300. The first constriction diffusion membrane 11200 is configured to minimize, resist, or prevent tissue ingrowth and attachment, while the first and second proliferation diffusion membranes 11100 and 11300 are configured to permit tissue ingrowth and attachment. FIG. 14A shows the glaucoma drainage system 11000 in a deflated state. FIG. 14B shows the glaucoma drainage system 11000 in an inflated state, where aqueous humor is present within an inflatable or dilatable reservoir 11010 defined between the first proliferation diffusion membrane 11100 and the first constriction diffusion membrane 11200. While the glaucoma drainage system 11000 is shown in FIG. 14B in an inflated state where the glaucoma drainage system 11000 is not uniformly inflated (e.g., the first proliferation membrane 11100 is shown adopting a generally nonlinear configuration while the second proliferation diffusion membrane 11300 and the constriction diffusion membrane 11200 are shown in a generally linear configuration), it is to be appreciated that the glaucoma drainage system 11000 may deform uniformly (e.g., the second proliferation diffusion membrane 11300 and the constriction diffusion membrane 11200 may deform in a manner that mirrors the deformation of the first proliferation diffusion membrane 11100). The fluid conduit 11500 may be situated between the first constriction diffusion membrane 11200 and one of the first and second proliferation diffusion membranes 11100 and 11300. As shown, the fluid conduit 11500 is situated between the first constriction diffusion membrane 11200 and the first proliferation diffusion membrane 11100. The constriction and proliferation diffusion membranes may be coupled together along an entirety of their adjoining surface areas, or may include one or more unbonded or uncoupled areas or regions, consistent with the discussion above.

As shown in FIG. 14B the first constriction diffusion membrane 11200 and the first proliferation diffusion membrane 11100 are coupled along their peripheral edges, but include an unbonded or uncoupled region interior thereto, which defines the reservoir 11010. Thus, the unbonded or uncoupled regions between the first constriction diffusion membrane 11200 and the first proliferation diffusion membrane 11100 can separate from one another as the reservoir 11010 inflates or dilates as aqueous humor enters the reservoir 11010.

It is to be appreciated that the configuration of the glaucoma drainage system 11000 shown in FIGS. 14A and 14B includes a reservoir 11010 that is defined between a constriction diffusion membrane and a proliferation diffusion membrane. Such a configuration provides that tissue ingrowth is permitted along one side of the reservoir while tissue ingrowth is minimized, resisted, or prevented along another side of the reservoir. Moreover, as the constriction diffusion membrane and the proliferation diffusion membrane are associated with different permeabilities, the evacuated aqueous humor will percolate through the constriction diffusion membrane and the proliferation diffusion membrane at different rates.

In some embodiments, these differential rates at which aqueous humor diffuses into or percolates through different membranes can be utilized to influence, direct, or otherwise "steer" the aqueous humor through the aqueous humor diffusion member. In some embodiments, the aqueous humor diffusion member may be configured such that a higher percentage (or higher volume) of aqueous humor is directed toward a first exterior surface of the aqueous humor diffusion member than toward a second exterior surface of the aqueous humor diffusion member. Likewise, in some embodiments, the aqueous humor diffusion member may be configured such that a percentage of the aqueous humor is directed toward a periphery of the aqueous humor diffusion member. Such configurations provide that the evacuated aqueous humor can be steered toward a designated region of the surrounding tissue, such as a region of the surrounding tissue that is more adapted to absorb the evacuated aqueous humor and that is more adapted to facilitate absorption into the tear film.

For example, with continued reference to FIGS. 14A and 14B, in some embodiments, the first proliferation diffusion membrane 11100 a higher flux than the flux of the first constriction diffusion membrane 11200, and thus a higher percentage (or higher volume) of aqueous humor is steered toward an exterior surface extending along the first proliferation diffusion membrane 11100 relative to a percentage (or volume) of aqueous humor that is steered toward an exterior surface extending along the second proliferation diffusion membrane 11300. It is to be appreciated that, in some embodiments, such a configuration may be additionally or alternatively achieved by forming a first constriction diffusion membrane that has a higher flux than the flux of a second constriction diffusion membrane. In some embodiments, such a configuration is additionally or alternatively achieved by forming first proliferation diffusion membrane such that it has a higher flux than the flux of second proliferation diffusion membrane. In some embodiments, such a configuration may additionally or alternatively be achieved by forming the boundaries between adjacently situated diffusion membranes such that different boundaries are associated with different flux. Differing boundaries associated with different flux may be achieved through the manner in which adjacently situated diffusion membranes are adhered or bonded to one another.

While the glaucoma drainage system 11000 shown in FIGS. 14A and 14B includes a fluid conduit 11500 that is situated between the first proliferation diffusion membrane 11100 and the first constriction diffusion membrane 11200, and a reservoir 11010 that is defined between the first proliferation diffusion membrane 11100 and the first constriction diffusion membrane 11200, it should be appreciated that the first constriction diffusion membrane may be formed of a plurality of laminated layers of polymer material (as discussed above) and the fluid conduit 11500 may be situated between adjacent layers of the polymer material. Additionally or alternatively, in some examples, one or more of the adjacently facing layers of polymer material forming the constriction membrane may include one or more unbonded, uncoupled, or unlaminated areas or regions, consistent with the discussion above, such that the unbonded, uncoupled, or unlaminated areas or regions of the adjacently facing layers of polymer material remain free to separate from, or slide or move relative to one another and may define, at least in part, the reservoir 11010.

In various embodiments, one or more portions of the glaucoma drainage systems discussed herein may include or be coated by one or more therapeutic agents, such as one or more glaucoma medications, as those of skill will appreciate. Additionally or alternatively, in various embodiments, one or more portions of the glaucoma drainage systems discussed herein may include one or more markers for visually or electronically (e.g., radiopaque markers) determining proper placement of the glaucoma drainage system within the anatomy.

It should be appreciated that in various embodiments, the diffusion membrane materials may additionally or alternatively be subjected to one or more processes to remove air trapped within the various voids within the material (e.g., denucleation). These processes may be combined with one or more of the hydrophilic coating processes discussed above. Entrapped air can sometimes interfere with wetting or saturation of the material with aqueous humor which could impair the efficiency of the aqueous humor diffusing into the aqueous humor diffusion member and being reabsorbed by the body. In some embodiments, entrapped air can be removed by soaking the material in a series of baths. In some embodiments, these baths may progress from one or more alcohol baths to one or more sterile water baths.

Example 1

A medical device was constructed according to the following method. A bottom sacrificial compression layer of thick distended PTFE tape was prepared by laser cutting a small coupon of PTFE distended tape. In particular, the shape of the glaucoma drainage device laser cut from the sacrificial PTFE layer corresponded to the shape of the first stratum 9010 illustrated in FIG. 10. All chads were removed and the sacrificial layer was aligned and placed on a jig plate configured to accommodate the small coupon. A first coupon of microporous diffusion material (e.g., multilayered ePTFE) was then placed over the small coupon of sacrificial PTFE material. The shape of the glaucoma drainage device was not laser cut into the first coupon of microporous diffusion material. The first coupon of microporous diffusion material was oriented such that the tissue ingrowth proliferation side of the first coupon of microporous diffusion material was facing downwardly toward the sacrificial PTFE coupon.

A layer of adhesive film (e.g., FEP) was then prepared by laser cutting the shape of the glaucoma drainage device into the adhesive film identical in size and location to that done in the sacrificial PTFE coupon. All chads were then removed, and the adhesive film layer was aligned and placed over the microporous diffusion, ensuring that the adhesive film lies flat with no wrinkles or foldovers. A second coupon of microporous diffusion material (e.g., multilayered ePTFE) was then placed over the adhesive film. The shape of the glaucoma drainage device was not laser cut into the second coupon of microporous diffusion material. The second coupon of microporous diffusion material was oriented such that the tissue ingrowth proliferation side of the second coupon of microporous diffusion material was facing upwardly away from the adhesive film. A top sacrificial compression layer of thick distended PTFE tape was then placed over the second coupon of microporous diffusion material. The shape of the glaucoma drainage device was not laser cut into the top sacrificial compression layer of thick distended PTFE tape. With this lamination stack setup, the jig was compressed such that the first and second coupons of microporous diffusion material were uniformly compressed with the exception of laser cut areas corresponding to the size and shape of the glaucoma drainage device. That is, with the cut out of the glaucoma drainage device shape performed in the first bottom sacrificial later layer, only minimal force insufficient to create a bond between the first and second coupons of microporous diffusion material is applied to the area corresponding in size and shape to the glaucoma drainage device. Similarly, because a chad corresponding to the size and shape of the glaucoma drainage device was removed from the adhesive layer during the layup process, no adhesive film is applied to the corresponding areas of the first and second coupons of microporous diffusion material.

The jig and layup was then placed onto a heated press platen, such as that of a desktop hot press, preheated to about 280 C, and sufficiently compressed for designated period of at least 5 minutes for a bond to occur between the first and second coupons of microporous diffusion material and adhesive film, while avoiding any significant bonding of the laminate to the sacrificial layers. The laminate was then removed from the press and allowed to cool to room temperature.

The resulting laminate was then lasercut to final size. In particular, the cut line followed the trace of the glaucoma drainage device shape formed in the sacrificial first layer of PTFE, offset a short distance (~1 mm) outward so that the perimeter of the device shape included the portion of first and second coupons of microporous diffusion material that were bonded together.

A fluid conduit formed of a silicone tube was inserted between the uncompressed layers leading into the interior of glaucoma drainage device by separating uncompressed layers slightly and inserting the tube up to an interior perimeter defined by where the first and second coupons of microporous diffusion material were bonded together. To tube was then secured to the glaucoma drainage device according to known methods.

Example 2

A medical device was constructed according to the following method. A bottom sacrificial compression layer of thick distended PTFE tape was prepared by laser cutting a small coupon of PTFE distended tape. The shape of a glaucoma drainage device consistent with the above was laser cut from the small coupon, and included approximately an 8 mm circular dimension. In particular, the shape of the glaucoma drainage device laser cut from the small coupon corresponded to the shape of the second stratum 9020 illustrated in FIG. 10. That is, the shape of the glaucoma drainage device laser cut from the small coupon included an ovular aqueous humor diffusion region and a rectangular erosion element consistent with the disclosure above. All chads were removed and the sacrificial layer was aligned and placed on a jig plate configured to accommodate the small coupon. A first coupon of microporous diffusion material (e.g., multilayered ePTFE) was then placed over the small coupon of sacrificial PTFE material. The shape of the glaucoma drainage device was not laser cut into the first coupon of microporous diffusion material. The first coupon of microporous diffusion material was oriented such that the tissue ingrowth proliferation side of the first coupon of microporous diffusion material was facing downwardly toward the sacrificial PTFE coupon.

A layer of adhesive file (e.g., FEP) was then prepared by laser cutting the shape of the glaucoma drainage device, less the rectangular erosion element feature, into the adhesive film identical in size and location (but with the exception of the rectangular erosion element feature) to that done in the sacrificial PTFE coupon. In particular, the shape of the glaucoma drainage device laser cut from the adhesive film corresponded to the shape of the first stratum 9010 illustrated in FIG. 10. All chads were then removed, and the adhesive film layer was aligned and placed over the microporous diffusion, ensuring that the adhesive film lies flat with no wrinkles or foldovers. A second coupon of microporous diffusion material (e.g., multilayered ePTFE) was then placed over the adhesive film. The shape of the rectangular erosion element was laser cut into the second coupon of microporous diffusion material, identical in size and location to that done in the sacrificial PTFE coupon. All chads were then removed, and the second coupon of microporous diffusion material was oriented such that the tissue ingrowth proliferation side of the second coupon of microporous diffusion material was facing upwardly away from the adhesive film.

A top sacrificial compression layer of thick distended PTFE tape was then placed over the second coupon of microporous diffusion material. The shape of the glaucoma drainage device was not laser cut into the top sacrificial compression layer of thick distended PTFE tape. With this lamination stack setup, the jig was compressed such that the first and second coupons of microporous diffusion material were uniformly compressed with the exception of laser cut areas corresponding to the size and shape of the glaucoma drainage device cut into the first sacrificial layer.

The jig and layup was then placed onto a heated press platen, such as that of a desktop hot press, preheated to about 280 C, and sufficiently compressed for designated period of at least 5 minutes for a bond to occur between the first and second coupons of microporous diffusion material and adhesive film, while avoiding any significant bonding of the laminate to the sacrificial layers. The laminate was then removed from the press and allowed to cool to room temperature.

The resulting laminate was then laser cut to final size consistent with the laser cutting process of Example 1, with the exception that no offset was cut around the rectangular portion defining the erosion element. The resulting laminate included a bottom microporous diffusion material layer consistent in size and shape with the shape of the second stratum 9020 illustrated in FIG. 10, and a top microporous diffusion material layer consistent in size and shape with the shape of the first stratum 9010 illustrated in FIG. 10.

A fluid conduit formed of a silicone tube was inserted between the uncompressed layers leading into the interior of glaucoma drainage device by separating uncompressed layers slightly and inserting the tube up to an interior perimeter defined by where the first and second coupons of microporous diffusion material were bonded together. To tube was then secured to the glaucoma drainage device according to known methods.

Example 3

The hydrophobic ePTFE device assembly from Example 1 or 2 was hydrophilically coated in the following manner. The ePTFE was wet out by directly delivering about 1 ml of 100% isopropyl alcohol through device's fluid conduit (e.g., silicone tubing) and flushed through the ePTFE reservoir. The excess alcohol was then flushed out of device with about 1 ml deionized water (nominal resistance ~10^6 ohm) directed through the fluid conduit and ePTFE reservoir. Approximately 1 ml of 0.2 wt % polyvinylalcohol aqueous solution was then directly flushed through the fluid conduit and ePTFE reservoir, and allowed to equilibrate for approximately 10 minutes. Approximately 1 ml of distilled water was them flushed through the fluid conduit and ePTFE reservoir. Approximately 1 ml of crosslinking aqueous solution (2 vol % glutaraldehyde in approximately 0.3 Molar hydrochloric acid was raised in temperature to about 40 C and directly flushed through the device, and allowed to equilibrate for approximately 15 minutes. Approximately 2.5 ml of deionized water was flushed directly through the fluid conduit and ePTFE reservoir. The material was then equilibrated in a beaker of approximately 40 ml of fresh deionized water. The resulting assembly was then dried in an air oven at 115 C for approximately 10 minutes.

Example 4

A device from Example 3 was implanted in the superotemporal quadrant in the subconjunctival plane of a New Zealand White Rabbit and evaluated for an in-life period of 14 days. During implantation, a tunnel was made at the limbus using a 25 gauge needle, in which the fluid conduit was passed into the anterior chamber. To visualize the reservoir of aqueous fluid, an aqueous solution of 0.01% sodium fluorescein was used. Infused fluorescein is excited by ultraviolet light and strongly fluoresces, easily visible in a darkened environment. Prior to sacrifice, a 0.01% sodium fluorescein aqueous solution was injected into the anterior chamber of the implanted eye through a 30 gauge needle at a nominal flowrate of approximately 10 μl/m in for a period of about 10 minutes. At the 14 day timepoint, a strongly fluorescent reservoir was observed as well as fluorescent vessels emanating from the implant reservoir area.

Example 5

A device from Example 1 was combined with constricting O-rings by inserting an end of tweezers through an ID of an individual O-ring. The O-ring is manually slid distally along the tweezer legs to dilate the O-ring inner diameter. The legs of the tweezers are separated to further dilate the O-ring to near the outer diameter of the fluid conduit of the device of Example. The fluid conduit is then inserted through the tweezer legs to at least 5 mm distal an end thereof. The tweezer legs are then retracted and the tweezers are removed such that the O-ring retracts and partially constricts the fluid conduit of the device of Example 1.

The second of the fluid conduit including the O-rings was then coated with uncured silicone sufficiently to envelop the O-rings. The coating was done around a portion of less than all of the circumference of the fluid conduit and subsequently heat cured. This configuration provided that a small section of O-ring remained bare and exposed. To titrate, the physician can manually cut or laser the O-rings where accessible at the uncoated section.

The inventive scope of this application has been described above both generically and with regard to specific examples. It will be apparent to those skilled in the art that various modifications and variations can be made in the examples without departing from the scope of the disclosure. Likewise, the various components discussed in the examples discussed herein are combinable. Thus, it is intended that the examples cover the modifications and variations of the inventive scope.

What is claimed is:

1. A fluid drainage system for controlling fluid pressure in an eye of a patient, the system comprising:
- a compliant fluid conduit suitable for implantation in the eye of the patient, the compliant fluid conduit configured to permit fluid evacuation from a fluid reservoir of the eye of the patient,
- a flow adjuster associated with the compliant fluid conduit, the flow adjuster being modifiable to increase and decrease a fluid flow rate through the compliant fluid conduit.

2. The system of claim 1, wherein the flow adjuster is selectively modifiable between at least three flow restriction configurations including a first restriction configuration restricting flow through the fluid conduit to a first flow rate, a second restriction configuration restricting flow through the fluid conduit to a second flow rate that is greater than the first flow rate, and a third restriction configuration restricting flow through the fluid conduit to a third flow rate that is less than the first flow rate.

3. The system of the claim 1, wherein the flow adjuster includes a plurality of resistive elements, the flow adjuster being modifiable by replacing a first one of the plurality of resistive elements with a second one of the plurality of resistive elements or a third one of the plurality of resistive elements, wherein the second resistive element operates to increase fluid flow through the fluid conduit relative to the first resistive element, and wherein the third resistive element operates to decrease fluid flow through the fluid conduit relative to the first resistive element.

4. The system of claim 3, wherein the second resistive element is a porous resistive element that is permeable to fluid.

5. The system of claim 3, wherein the third resistive element is a non-porous resistive element that is impermeable to fluid.

6. The system of claim 3, wherein the first resistive element is removable or ablatable.

7. The system of claim 3 wherein at least one of the first, second, and third resistive elements is positionable interior to a lumen of the fluid conduit.

8. The system of claim 3, wherein at least one of the first, second, and third resistive elements is positionable exterior to a lumen of the fluid conduit.

9. The system of claim 1, further comprising a microporous body coupled to the fluid conduit.

10. The system of claim 1, wherein the fluid reservoir is an anterior chamber of the eye and the fluid is aqueous humor, and wherein the fluid drainage system operates to regulate an intraocular pressure of the eye of the patient.

11. The system of claim 1, wherein the fluid conduit comprises a fluoropolymer.

12. The system of claim 11, wherein the fluoropolymer is expanded polytetrafluoroethylene.

13. The system of claim 1, wherein the fluid flow rate through the fluid conduit is post operatively modifiable through a clear corneal approach.

14. The system of claim 1, wherein the flow adjuster is modifiable by removing at least a portion of the flow adjuster and replacing the portion of the flow adjuster with a different flow adjuster.

15. The system of claim 1, wherein the compliant fluid conduit defines one or more lumens, and the flow adjuster obstructs fluid flow through at least one of the lumens in the one or more lumens to define the fluid flow rate.

16. The system of claim 15, wherein the flow adjuster includes one or more resistive elements, and the one or more resistive elements are releasably positioned within the one or more lumens.

17. The system of claim 16, wherein at least one of the one or more resistive elements is bioabsorbable.

18. A method comprising:

providing a compliant fluid conduit suitable for implantation in an eye of a patient, the compliant fluid conduit including a first flow adjuster associated with the fluid conduit and configured to permit fluid evacuation from a fluid reservoir of the eye of the patient at a first flow rate;

removing the first flow adjuster; and replacing the first flow adjuster with a second flow adjuster configured to permit fluid evacuation from the fluid reservoir of the eye of the patient at second flow rate.

19. The method of claim 18, wherein the second flow rate is higher than the first flow rate.

20. The method of claim 18, wherein the second flow rate is less than the first flow rate.

21. A method of treating glaucoma comprising:

implanting a fluid drainage system in an eye of a patient to control an intraocular pressure of the eye of the patient, the fluid drainage system including, a compliant fluid conduit configured to permit fluid evacuation from a fluid reservoir of a biological tissue to a region exterior to the fluid reservoir of the biological tissue, and a flow adjuster associated with the fluid conduit and configured to permit fluid evacuation from the fluid reservoir of the biological tissue of the patient at a first flow rate; and post-operatively modifying the flow adjuster to permit fluid evacuation from the fluid reservoir of the biological tissue of the patient to increase and decrease the first flow rate through the compliant fluid conduit to a second flow rate different from the first flow rate.

22. The method of claim 21, further comprising removing the flow adjuster.

23. The method of claim 21, further comprising replacing the flow adjuster with a different flow adjuster.

24. The method of claim 21, further comprising varying a length of the flow adjuster from a first length to a second length that is shorter than the first length.

* * * * *